(12) United States Patent
Talley et al.

(10) Patent No.: US 6,436,967 B1
(45) Date of Patent: Aug. 20, 2002

(54) PROCESS FOR PREPARING PRODRUGS OF BENZENESULFONAMIDE-CONTAINING COX-2 INHIBITORS

(75) Inventors: John J Talley, St. Louis, MO (US); James W Malecha, Libertyville, IL (US); Stephen Bertenshaw, Cheshire, CT (US); Matthew J Graneto; Jeffery Carter, both of Chesterfield, MO (US); Jinglin Li, Hopewell, NJ (US); Srinivasan Nagarajan, Chesterfield, MO (US); David L Brown, Chesterfield, MO (US); Donald J Rogier, Jr., Chesterfield, MO (US); Thomas D Penning, Elmhurst, IL (US); Ish K Khanna, Vernon Hills, IL (US); Xiangdong Xu, Gurnee, IL (US); Richard M Weier, Lake Bluff, IL (US)

(73) Assignee: Pharmacia Corporation, St. Louis, MO (US)

( * ) Notice: Subject to any disclaimer, the term of this patent is extended or adjusted under 35 U.S.C. 154(b) by 0 days.

(21) Appl. No.: 09/661,859

(22) Filed: Sep. 14, 2000

Related U.S. Application Data

(63) Continuation of application No. 09/142,993, filed as application No. PCT/US97/05497 on Apr. 11, 1997, now abandoned, and a continuation-in-part of application No. 08/631,514, filed on Apr. 12, 1996, now abandoned.

(51) Int. Cl.$^7$ ............... A61K 31/44; A61K 31/415; C07D 263/04; C07D 403/02; C07C 303/08
(52) U.S. Cl. .............. 514/341; 514/377; 514/399; 514/400; 514/403; 514/406; 514/602; 546/274.1; 546/290; 548/225; 548/228; 548/229; 548/235; 548/314.7; 548/315.1; 548/315.4; 548/335.5; 548/338.5; 548/359.5; 548/375.1; 548/376.1; 548/377.1; 548/549; 548/556; 564/84; 564/91
(58) Field of Search ................. 514/341, 374, 514/602; 546/274.1, 290; 548/225, 228, 229, 235, 347, 315.1, 315.4, 335.5, 338.5, 359.5, 375.1, 376.1, 556; 564/84, 91

(56) References Cited

U.S. PATENT DOCUMENTS

| | | | |
|---|---|---|---|
| 5,338,749 A | 8/1994 | Wuest et al. | 514/364 |
| 5,344,991 A | 9/1994 | Reitz et al. | 568/34 |
| 5,380,738 A | 1/1995 | Norman et al. | 514/374 |
| 5,387,592 A | 2/1995 | Bradbury et al. | 514/312 |
| 5,389,635 A | 2/1995 | Olson | 514/255 |
| 5,393,790 A | 2/1995 | Reitz et al. | 514/709 |
| 5,616,601 A | 4/1997 | Khanna et al. | 514/399 |
| 5,633,272 A * | 5/1997 | Talley et al. | 514/378 |

FOREIGN PATENT DOCUMENTS

| | | | |
|---|---|---|---|
| JP | 1045374 | 2/1989 | 514/255 |
| JP | 4277724 | 10/1992 | 514/400 |
| JP | 5323522 | 12/1993 | 514/400 |
| WO | WO94/13635 | 6/1994 | 514/400 |
| WO | WO94/15932 | 7/1994 | 514/400 |
| WO | WO94/20480 | 9/1994 | 514/400 |
| WO | WO94/26731 | 11/1994 | 514/709 |
| WO | WO94/27980 | 12/1994 | 514/400 |
| WO | WO95/00501 | 1/1995 | 514/400 |
| WO | WO95/15316 | 6/1995 | 514/400 |

OTHER PUBLICATIONS

H. Faid–Allah and H. Mokhtar, *Ind. J. Chem*, 27, 245–249 (1988).
D Murkerjee et al, *Acta. Pharma. Jugosl.*, 31, 151–158 (1981).
G. Dorofeenko et al, *Khim. Farm. Zh.*, 16, 920–923, (1982).
T. Ivanov, *Mh. Chem.*, 97, 1499–1509 (1966).
J. Larsen and H. Bundagaard, Int. J. Pharmaceutics, 37, 87–95 (1987).
J. Larsen et al, Int. J. Pharmaceutics, 47, 103–110 (1988).
Y. LeBlanc et al, Bio & Med. Chem. Letters 5(18), 2123–2128 (1995).

* cited by examiner

*Primary Examiner*—Floyd D. Higel
*Assistant Examiner*—Ebenezer Sackey
(74) *Attorney, Agent, or Firm*—Senniger, Powers, Leavitt & Roedel

(57) ABSTRACT

This invention is in the field of antiinflammatory pharmaceutical agents and specifically relates to prodrugs of compounds which selectively inhibit cyclooxygenase-2.

The use of non-steroidal antiinflammatory drugs (NSAIDs) in treating pain and the swelling associated with inflammation also produce severe side effects, including life threatening ulcers. The recent discovery of an inducible enzyme associated with inflammation ("prostaglandin G/H synthase II" or "cyclooxygenase-2 (COX-2)") provides a viable target of inhibition which more effectively reduces inflammation and produces fewer and less drastic side effects.

32 Claims, No Drawings

PROCESS FOR PREPARING PRODRUGS OF BENZENESULFONAMIDE-CONTAINING COX-2 INHIBITORS

REFERENCE TO RELATED APPLICATIONS

This application is a continuation of U.S. Ser. No. 09/142,993, filed Mar. 18, 1999, now abandoned, which is a 371 of PCT/US97/05497, filed Apr. 11, 1997, and a Continuation-In-Part of U.S. Ser. No. 08/631,514, filed Apr. 12, 1996, now abandoned.

FIELD OF THE INVENTION

This invention is in the field of antiinflammatory pharmaceutical agents and specifically relates to prodrugs of compounds which selectively inhibit cyclooxygenase-2.

BACKGROUND OF THE INVENTION

The use of non-steroidal antiinflammatory drugs (NSAIDs) in treating pain and the swelling associated with inflammation also produce severe side effects, including life threatening ulcers. The recent discovery of an inducible enzyme associated with inflammation ("prostaglandin G/H synthase II" or "cyclooxygenase-2 (COX-2)") provides a viable target of inhibition which more effectively reduces inflammation and produces fewer and less drastic side effects.

Compounds which selectively inhibit cyclooxygenase-2 have been described. U.S. Pat. No. 5,380,738 describes oxazoles which selectively inhibit cyclooxygenase-2. U.S. Pat. No. 5,344,991 describes cyclopentenes which selectively inhibit cyclooxygenase-2. U.S. Pat. No. 5,393,790 describes spiro compounds which selectively inhibit cyclooxygenase-2. WO94/15932 describes thiophene and furan derivatives which selectively inhibit cyclooxygenase-2. WO94/27980 describes oxazoles which selectively inhibit cyclooxygenase-2. WO94/13635 describes compounds which selectively inhibit cyclooxygenase-2. WO94/20480 describes compounds which selectively inhibit cyclooxygenase-2. WO95/15316 describes pyrazolyl sulfonamide derivatives which selectively inhibit cyclooxygenase-2. However, in some circumstances, prodrugs of antiinflammatory compounds are advantageous, especially where the prodrugs have increased water solubility or delayed onset of action.

Substituted sulfonamides have been described. Pyrazolylsulfonylureas have been described as having possible hypoglycemic activity [H. Faid-Allah and H. Mokhtar, *Ind. J. Chem*, 27, 245 (1988)]. JP 1,045,374 describes water soluble tetrazolium compounds useful in assays for determining reducing substances. D. Mukerjee et al [*Acta. Pharma. Jugosl.*, 31, 151 (1981)] describe tetrazolium sulfonamides as antiviral agents. JP 4,277,724 describes triphenyl pyrazolines as nonlinear optical material. JP 5,323,522 describes the use of heterocyclic compounds in black and white photographic material. U.S. Pat. No. 5,389,635 describes substituted imidazoles as angiotensin II antagonists. U.S. Pat. No. 5,387,592 describes substituted benzimidazole derivatives as angiotensin II antagonists. G. Dorofeenko et al [*Khim. Farm. Zh.*, 16, 920 (1982)] describe pyridinium salts as antiviral agents. U.S. Pat. No. 5,338,749 describes diaryl-substituted heterocyclyl compounds as anti-arthritis agents. WO94/26731 describes thiophene compounds which selectively inhibit cyclooxygenase-2. WO95/00501 describes compounds which selectively inhibit cyclooxygenase-2, and specifically, 3-(4-(trifluoroacetylaminosulfonyl)phenyl)-2-(4-fluorophenyl)thiophene is described. T. Ivanov [*Mh. Chem.*, 97, 1499 (1966)] describes the preparation of diarylindone derivatives as possible indicators, and 2-(4-(N-methylaminosulfonyl)phenyl)-3-phenylindone is specifically described.

J. Larsen and H. Bundgaard [*Int. J. Pharmaceutics*, 37, 87 (1987)] describe the evaluation of N-acylsulfonamides as potential prodrug derivatives. J. Larsen et al [*Int. J. Pharmaceutics*, 47, 103 (1988)] describe the evaluation of N-methylsulfonamides as potential prodrug derivatives.

There currently exists a need for compounds suitable for injectable antiinflammatory compositions. The compounds of the present invention are found to show usefulness as prodrugs.

DESCRIPTION OF THE INVENTION

A class of substituted sulfonamide compounds useful as prodrugs is defined by Formula I:

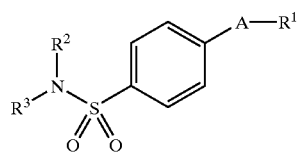

wherein A is a ring substituent selected from partially unsaturated heterocyclyl, heteroaryl, cycloalkenyl and aryl, wherein A is optionally substituted at a substitutable position with one or more radicals selected from alkylcarbonyl, formyl, halo, alkyl, haloalkyl, oxo, cyano, nitro, carboxyl, alkoxy, aminocarbonyl, alkoxycarbonyl, carboxyalkyl, cyanoalkyl, hydroxyalkyl, haloalkylsulfonyloxy, alkoxyalkyloxyalkyl, carboxyalkoxyalkyl, cycloalkylalkyl, alkenyl, alkynyl, heterocyclyloxy, alkylthio, cycloalkyl, aryl, heterocyclyl, cycloalkenyl, aralkyl, heterocyclylalkyl, alkylthioalkyl, arylcarbonyl, aralkylcarbonyl, aralkenyl, alkoxyalkyl, arylthioalkyl, aryloxyalkyl, aralkylthioalkyl, aralkoxyalkyl, alkoxycarbonylalkyl, aminocarbonylalkyl, alkylaminocarbonyl, N-arylaminocarbonyl, N-alkyl-N-arylaminocarbonyl, alkylaminocarbonylalkyl, alkylamino, N-arylamino, N-aralkylamino, N-alkyl-N-aralkylamino, N-alkyl-N-arylamino, aminoalkyl, alkylaminoalkyl, N-arylaminoalkyl, N-aralkylaminoalkyl, N-alkyl-N-aralkylaminoalkyl, N-alkyl-N-arylaminoalkyl, aryloxy, aralkoxy, arylthio, aralkylthio, alkylsulfinyl, alkylsulfonyl, aminosulfonyl, alkylaminosulfonyl, N-arylaminosulfonyl, arylsulfonyl, and N-alkyl-N-arylaminosulfonyl;

wherein $R^1$ is selected from heterocyclyl, cycloalkyl, cycloalkenyl and aryl, wherein $R^1$ is optionally substituted at a substitutable position with one or more radicals selected from alkyl, haloalkyl, cyano, carboxyl, alkoxycarbonyl, hydroxyl, hydroxyalkyl, haloalkoxy, amino, alkylamino, arylamino, nitro, alkoxyalkyl, alkylsulfinyl, halo, alkoxy and alkylthio;

wherein $R^2$ is selected from hydrido and alkoxycarbonylalkyl; and wherein $R^3$ is selected from alkyl, carboxyalkyl, acyl, alkoxycarbonyl, heteroarylcarbonyl, alkoxycarbonylalkylcarbonyl, alkoxycarbonylcarbonyl, amino acid residue, and alkylcarbonylaminoalkylcarbonyl;

provided A is not tetrazolium, or pyridinium; and further provided A is not indanone when $R^3$ is alkyl or carboxyalkyl;

or a pharmaceutically-acceptable salt thereof.

Compounds of Formula I would be useful for, but not limited to, the treatment of inflammation in a subject, and for treatment of other cyclooxygenase-2 mediated disorders, such as, as an analgesic in the treatment of pain and headaches, or as an antipyretic for the treatment of fever. For example, compounds of the invention would be useful to treat arthritis, including but not limited to rheumatoid arthritis, spondyloarthropathies, gouty arthritis, osteoarthritis, systemic lupus erythematosus and juvenile arthritis. Such compounds of the invention would be useful in the treatment of asthma, bronchitis, menstrual cramps, premature labor, tendinitis, bursitis, skin-related conditions such as psoriasis, eczema, burns and dermatitis, and from post-operative inflammation including from ophthalmic surgery such as cataract surgery and refractive surgery. Compounds of the invention also would be useful to treat gastrointestinal conditions such as inflammatory bowel disease, Crohn's disease, gastritis, irritable bowel syndrome and ulcerative colitis. Compounds of the invention would be useful for the prevention or treatment of cancer, such as colorectal cancer, and cancer of the breast, lung, prostate, bladder, cervix and skin. Compounds of the invention would be useful in treating inflammation in such diseases as vascular diseases, migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury, myocardial ischemia, and the like. The compounds would also be useful in the treatment of ophthalmic diseases, such as retinitis, retinopathies, uveitis, ocular photophobia, and of acute injury to the eye tissue. The compounds would also be useful in the treatment of pulmonary inflammation, such as that associated with viral infections and cystic fibrosis. The compounds would also be useful for the treatment of certain central nervous system disorders, such as cortical dementias including Alzheimer's disease, and central nervous system damage resulting from stroke, ischemia and trauma. The compounds of the invention are useful as anti-inflammatory agents, such as for the treatment of arthritis, with the additional benefit of having significantly less harmful side effects. These compounds would also be useful in the treatment of allergic rhinitis, respiratory distress syndrome, endotoxin shock syndrome, and atherosclerosis. The compounds would also be useful in the treatment of pain, but not limited to postoperative pain, dental pain, muscular pain, and pain resulting from cancer. The compounds would be useful for the prevention of dementias, such as Alzheimer's disease.

Besides being useful for human treatment, these compounds are also useful for veterinary treatment of companion animals, exotic animals and farm animals, including mammals, rodents, and the like. More preferred animals include horses, dogs, and cats.

The present compounds may also be used in co-therapies, partially or completely, in place of other conventional antiinflammatories, such as together with steroids, NSAIDs, 5-lipoxygenase inhibitors, $LTB_4$ antagonists and $LTA_4$ hydrolase inhibitors.

Suitable $LTB_4$ inhibitors include, among others, ebselen, Bayer Bay-x-1005, Ciba Geigy compound CGS-25019C, Leo Denmark compound ETH-615, Lilly compound LY-293111, Ono compound ONO-4057, Terumo compound TMK-688, Lilly compounds LY-213024, 264086 and 292728, ONO compound ONO-LB457, Searle compound SC-53228, calcitrol, Lilly compounds LY-210073, LY223982, LY233469, and LY255283, ONO compound ONO-LB-448, Searle compounds SC-41930, SC-50605 and SC-51146, and SK&F compound SKF-104493. Preferably, the $LTB_4$ inhibitors are selected from ebselen, Bayer Bay-x-1005, Ciba Geigy compound CGS-25019C, Leo Denmark compound ETH-615, Lilly compound LY-293111, Ono compound ONO-4057, and Terumo compound TMK-688.

Suitable 5-LO inhibitors include, among others, masoprocol, tenidap, zileuton, pranlukast, tepoxalin, rilopirox, flezelastine hydrochloride, enazadrem phosphate, and bunaprolast.

The present compounds may also be used in combination therapies with opioids and other analgesics, such as morphine, meperidine or codeine.

The term "cyclooxygenase-2 inhibitor" embraces compounds which selectively inhibit cyclooxygenase-2 over cyclooxygenase-1. Preferably, the compounds have a cyclooxygenase-2 $IC_{50}$ of less than about 0.5 $\mu$M, and also have a selectivity ratio of cyclooxygenase-2 inhibition over cyclooxygenase-1 inhibition of at least 50, and more preferably of at least 100. Even more preferably, the compounds have a cyclooxygenase-1 $IC_{50}$ of greater than about 1 $\mu$M, and more preferably of greater than 20 $\mu$M. Such preferred selectivity may indicate an ability to reduce the incidence of common NSAID-induced side effects.

The phrase "therapeutically-effective" is intended to qualify the amount of each agent for use in the combination therapy which will achieve the goal of improvement in severity and the frequency of incidence over treatment of each agent by itself, while avoiding adverse side effects typically associated with alternative therapies.

The phrase "combination therapy" (or "co-therapy"), in defining use of a cyclooxygenase-2 inhibitor agent and another agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

The term "prodrug" refers to compounds which are drug precursors which, following administration to a subject and subsequent absorption, is converted to an active species in vivo via some process, such as a metabolic process. Other products from the conversion process are easily disposed of by the body. More preferred prodrugs produce products from the conversion process which are generally accepted as safe.

A preferred class of compounds which inhibit cyclooxygenase-2 consists of compounds of Formula I wherein A is selected from partially unsaturated heterocyclyl, 5- or 6-membered heteroaryl, lower cycloalkenyl and phenyl, wherein A is optionally substituted at a substitutable position with one or more radicals selected from formyl, lower alkylcarbonyl, halo, lower alkyl, lower haloalkyl, oxo, cyano, nitro, carboxyl, lower alkoxy, aminocarbonyl, lower alkoxycarbonyl, lower carboxyalkyl, lower cyanoalkyl, lower hydroxyalkyl, lower haloalkylsulfonyloxy, lower alkoxyalkyloxyalkyl, lower carboxyalkoxyalkyl, lower cycloalkylalkyl, lower alkenyl, lower alkynyl, heterocyclyloxy, lower alkylthio, lower cycloalkyl, phenyl, 5-6 membered heterocyclyl, lower cycloalkenyl, lower phenylalkyl, 5-6 membered heterocyclylalkyl, lower alkylthioalkyl, phenylcarbonyl, lower phenylalkylcarbonyl, lower phenylalkenyl, lower alkoxyalkyl, lower phenylthioalkyl, lower phenyloxyalkyl, lower phenylalkylthioalkyl, lower phenylalkoxyalkyl, lower alkoxycarbonylalkyl, lower aminocarbonylalkyl, lower alkylaminocarbonyl, N-phenylaminocarbonyl, lower N-alkyl-N-phenylaminocarbonyl, lower alkylaminocarbonylalkyl, lower alkylamino, N-phenylamino, lower N-phenylalkylamino, lower N-alkyl-N-phenalkylamino, lower N-alkyl -N-phenylamino, lower aminoalkyl, lower alkylaminoalkyl, lower N-phenylaminoalkyl, lower N-phenalkylaminoalkyl, lower N-alkyl-N-phenalkylaminoalkyl, lower N-alkyl-N-phenylaminoalkyl, phenyloxy, lower phenylalkoxy, lower phenylthio, lower phenalkylthio, lower alkylsulfinyl, lower alkylsulfonyl, aminosulfonyl, lower alkylaminosulfonyl, N-phenylaminosulfonyl, phenylsulfonyl, and lower N-alkyl-N-phenylaminosulfonyl; wherein $R^1$ is selected from 5- or 6-membered heterocyclyl, lower cycloalkyl, lower cycloalkenyl and phenyl, where $R^1$ is optionally substituted at a substitutable position with one or more radicals selected from lower alkyl, lower haloalkyl, cyano, carboxyl, lower alkoxycarbonyl, hydroxyl, lower hydroxyalkyl, lower haloalkoxy, amino, lower alkylamino, phenylamino, nitro, lower alkoxyalkyl, lower alkylsulfinyl, halo, lower alkoxy and lower alkylthio; wherein $R^2$ is selected from hydrido, and lower alkoxycarbonylalkyl; and wherein $R^3$ is selected from lower alkyl, lower carboxyalkyl, alkanoyl, aroyl, amino acid residue, lower alkoxycarbonyl, lower alkoxyalkylcarbonyl, (5-6-membered heteroaryl)carbonyl, lower alkoxycarbonylalkylcarbonyl, lower alkoxycarbonylcarbonyl, and lower alkylcarbonylaminoalkylcarbonyl; or a pharmaceutically-acceptable salt thereof.

A more preferred class of compounds which inhibit cyclooxygenase-2 consists of compounds of Formula I wherein A is a radical selected from thienyl, oxazolyl, furyl, pyrrolyl, thiazolyl, imidazolyl, benzofuryl, indenyl, benzothienyl, isoxazolyl, pyrazolyl, cyclopentenyl, cyclopentadienyl, benzindazolyl, benzopyranopyrazolyl, phenyl, and pyridyl, wherein A is optionally substituted at a substitutable position with one or more radicals selected from formyl, methylcarbonyl, fluoro, chloro, bromo, methyl, trifluoromethyl, difluoromethyl, oxo, cyano, carboxyl, methoxy, aminocarbonyl, methoxycarbonyl, ethoxycarbonyl, carboxypropyl, hydroxymethyl, cyanomethyl, phenyl, phenylmethyl, methoxycarbonyl, phenylcarbonyl, methoxymethyl, phenyloxymethyl, aminocarbonylmethyl, carboxymethyl, and phenyloxy; wherein $R^1$ is selected from thienyl, oxazolyl, isoxazolyl, furyl, thiazolyl, pyridyl, and phenyl, where $R^1$ is optionally substituted at a substitutable position with one or more radicals selected from methyl, trifluoromethyl, hydroxyl, hydroxymethyl, trifluoromethoxy, nitro, methoxymethyl, fluoro, chloro, bromo, methoxy and methylthio; wherein $R^2$ is hydrido, or ethoxycarbonylmethyl; and wherein $R^3$ is selected from methyl, carboxymethyl, formyl, methylcarbonyl, ethylcarbonyl, propylcarbonyl, isopropylcarbonyl, butylcarbonyl, tert-butylcarbonyl, pentylcarbonyl, hydroxyethylcarbonyl, benzylcarbonyl, phenyl(hydroxyl)methylcarbonyl, methoxycarbonyl, tert-butoxycarbonyl, methoxyethylcarbonyl, phenylcarbonyl, ethoxymethylcarbonyl, methoxymethylcarbonyl, carboxyethylcarbonyl, carboxymethylcarbonyl, carboxy(1,2-bis(hydroxy)ethyl))carbonyl, methoxycarbonylmethylcarbonyl, aminomethylcarbonyl, methoxycarbonylethylcarbonyl, methoxycarbonyl, tert-butoxycarbonylaminomethylcarbonyl, and methylcarbonylaminomethylcarbonyl; or a pharmaceutically-acceptable salt thereof.

Within Formula I there is a subclass of compounds of high interest represented by Formula II:

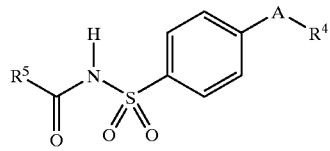

wherein A is a ring substituent selected from partially unsaturated heterocyclyl, 5- or 6-membered heteroaryl, lower cycloalkenyl and phenyl; wherein A is optionally substituted at a substitutable position with one or more radicals selected from acyl, halo, hydroxy, lower alkyl, lower haloalkyl, oxo, cyano, nitro, carboxyl, lower alkoxy, aminocarbonyl, lower alkoxycarbonyl, lower carboxyalkyl, lower cyanoalkyl, lower hydroxyalkyl, lower alkylcarbonyloxyalkyl, and phenyl;

wherein $R^4$ is selected from heterocyclyl, cycloalkyl, cycloalkenyl and phenyl, wherein $R^4$ is optionally substituted at a substitutable position with one or more radicals selected from lower alkyl, lower haloalkyl, cyano, carboxyl, lower alkoxycarbonyl, hydroxyl, lower hydroxyalkyl, lower haloalkoxy, amino, lower alkylamino, phenylamino, nitro, lower alkoxyalkyl, lower alkylsulfinyl, halo, lower alkoxy and lower alkylthio; and wherein $R^5$ is selected from hydrido, lower alkyl, lower alkoxy, lower alkoxyalkyl, phenyl, lower carboxyalkyl, lower alkoxycarbonylalkyl, lower alkoxycarbonyl, lower aminoalkyl, lower alkoxycarbonylaminoalkyl, and lower alkylcarbonylaminoalkyl;

or a pharmaceutically-acceptable salt thereof.

A preferred class of compounds consists of those compounds of Formula II wherein A is a ring substituent selected from thienyl, oxazolyl, furyl, pyrrolyl, thiazolyl, imidazolyl, benzofuryl, indenyl, benzothienyl, isoxazolyl, pyrazolyl, cyclopentenyl, cyclopentadienyl, benzindazolyl, benzopyranopyrazolyl, phenyl, and pyridyl, wherein A is optionally substituted at a substitutable position with one or more radicals selected from acyl, halo, hydroxy, lower alkyl, lower haloalkyl, oxo, cyano, nitro, carboxyl, lower alkoxy, aminocarbonyl, lower alkoxycarbonyl, lower carboxyalkyl, lower cyanoalkyl, lower alkylcarbonyloxyalkyl, phenyl and lower hydroxyalkyl; wherein $R^4$ is selected from 5–6 membered heteroaryl and phenyl, wherein $R^4$ is optionally substituted at a substitutable position with one or more radicals selected from lower alkyl, lower haloalkyl, cyano, carboxyl, lower alkoxycarbonyl, hydroxyl, lower hydroxyalkyl, lower haloalkoxy, amino, lower alkylamino, phenylamino, nitro, lower alkoxyalkyl, lower alkylsulfinyl, halo, lower alkoxy and lower alkylthio; and wherein $R^5$ is selected from hydrido, lower alkyl, lower alkoxy, lower alkoxyalkyl, phenyl, lower alkoxycarbonylalkyl, lower alkoxycarbonyl, lower aminoalkyl, lower alkoxycarbonylaminoalkyl, and lower alkylcarbonylaminoalkyl; or a pharmaceutically-acceptable salt thereof.

A class of compounds of particular interest consists of those compounds of Formula II wherein A is a ring substituent selected from thienyl, oxazolyl, furyl, pyrrolyl, thiazolyl, imidazolyl, isothiazolyl, isoxazolyl, pyrazolyl, cyclopentenyl, cyclopentadienyl, benzindazolyl, benzopyranopyrazolyl, phenyl, and pyridyl; wherein A is optionally substituted at a substitutable position with one or more radicals selected from formyl, fluoro, chloro, bromo, methyl, trifluoromethyl, oxo, cyano, carboxyl, methoxy, aminocarbonyl, methoxycarbonyl, ethoxycarbonyl, carboxymethyl, carboxypropyl, methylcarbonyloxymethyl, and hydroxymethyl; wherein $R^4$ is selected from thienyl, pyridyl and phenyl, wherein $R^4$ is optionally substituted at a substitutable position with one or more radicals selected from methyl, trifluoromethyl, hydroxyl, hydroxymethyl, trifluoromethoxy, nitro, methoxymethyl, fluoro, chloro, bromo, methoxy and methylthio; and wherein $R^5$ is selected from hydrido, methyl, ethyl, isopropyl, propyl, tert-butyl, butyl, pentyl, methoxy, tert-butoxy, methoxyethyl, ethoxymethyl, methoxymethyl, phenyl, carboxyethyl, methoxycarbonylmethyl, methoxycarbonylethyl, tert-butoxycarbonylaminomethyl, methoxycarbonyl, aminomethyl, and methylcarbonylaminomethyl; or a pharmaceutically-acceptable salt thereof.

Within Formula I there is a subclass of compounds of high interest represented by Formula III:

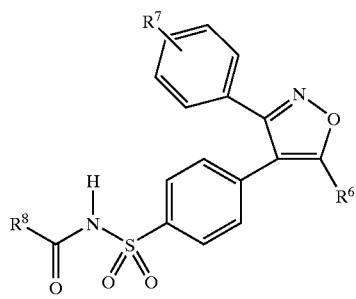

III wherein $R^6$ is selected from hydroxyl, lower alkyl, carboxyl, halo, lower carboxyalkyl, lower alkoxycarbonylalkyl, lower aralkyl, lower aralkoxyalkyl, lower haloalkyl, lower hydroxylalkyl, lower aryl(hydroxylalkyl), lower haloalkylsulfonyloxy, lower alkoxyalkyloxyalkyl, lower carboxyalkoxyalkyl, lower cycloalkylalkyl and lower cycloalkyl;

wherein $R^7$ is one or more radicals selected from hydrido, lower alkyl, lower haloalkyl, cyano, carboxyl, lower alkoxycarbonyl, hydroxyl, lower hydroxyalkyl, lower haloalkoxy, amino, lower alkylamino, phenylamino, nitro, lower alkoxyalkyl, lower alkylsulfinyl, halo, lower alkoxy and lower alkylthio; and wherein $R^8$ is selected from hydrido, lower alkyl, lower alkoxy, lower alkoxyalkyl, phenyl, lower carboxyalkyl, lower alkoxycarbonylalkyl, lower alkoxycarbonyl, lower aminoalkyl, lower alkoxycarbonylaminoalkyl, and lower alkylcarbonylaminoalkyl;

or a pharmaceutically-acceptable salt thereof.

A preferred class of compounds consists of those compounds of Formula III wherein $R^6$ is selected from lower alkyl, lower haloalkyl, and lower hydroxylalkyl; wherein $R^7$ is one or more radicals selected from hydrido, lower alkyl, halo, and lower alkoxy; and wherein $R^8$ is selected from lower alkyl, phenyl, and lower aminoalkyl; or a pharmaceutically-acceptable salt thereof.

A more preferred class of compounds consists of those compounds of Formula III wherein $R^6$ is selected from methyl, difluoromethyl and hydroxymethyl; wherein $R^7$ is one or more radicals selected from hydrido, methyl, fluoro, chloro, bromo, and methoxy; and wherein $R^8$ is selected from methyl, ethyl, isopropyl, propyl, tert-butyl, butyl, pentyl, phenyl, and aminomethyl; or a pharmaceutically-acceptable salt thereof.

A family of specific compounds of particular interest within Formulas I–III consists of compounds and pharmaceutically-acceptable salts thereof as follows:

N-[[4-[2-(2-methylpyridin-6-yl)-4-(trifluoromethyl)-1H-imidazol-1-yl]phenyl]sulfonyl]acetamide;

N-[[4-[2-(2-methylpyridin-6-yl)-4-(trifluoromethyl)-1H-imidazol-1-yl]phenyl]sulfonyl]propanamide;

N-[[4-[2-(2-methylthiazol-4-yl)-4-(trifluoromethyl)-1H-imidazol-1-yl]phenyl]sulfonyl]acetamide;

N-[[4-[2-(2-methylthiazol-4-yl)-4-(trifluoromethyl)-1H-imidazol-1-yl]phenyl]sulfonyl]propanamide;

N-[[4-[2-(4-methylthiazol-2-yl)-4-(trifluoromethyl)-1H-imidazol-1-yl]phenyl]sulfonyl]acetamide;

N-[[4-[2-(4-methylthiazol-2-yl)-4-(trifluoromethyl)-1H-imidazol-1-yl]phenyl]sulfonyl]propanamide;

N-[[4-[2-(2-methylpyridin-3-yl)-4-(trifluoromethyl)-1H-imidazol-1-yl]phenyl]sulfonyl]acetamide;

N-[[4-[2-(2-methylpyridin-3-yl)-4-(trifluoromethyl)-1H-imidazol-1-yl]phenyl]sulfonyl]acetamide;

N-[[4-[2-(3-pyridinyl)-4-(trifluoromethyl)-1H-imidazol-1-yl]phenyl]sulfonyl]acetamide;

N-[[4-[2-(5-methylpyridin-3-yl)-4-(trifluoromethyl)-1H-imidazol-1-yl]phenyl]sulfonyl]acetamide;

N-[[4-[2-(2-methylpyridin-3-yl)-4-(trifluoromethyl)-1H-imidazol-1-yl]phenyl]sulfonyl]acetamide;

N-[[4-[2-(5-methylpyridin-3-yl)-4-(trifluoromethyl)-1H-imidazol-1-yl]phenyl]sulfonyl]butanamide;

N-[[4-[2-(2-methylpyridin-3-yl)-4-(trifluoromethyl)-1H-imidazol-1-yl]phenyl]sulfonyl]butanamide;

N-[[4-[2-(3-chloro-5-methylphenyl)-4-(trifluoromethyl)-1H-imidazol-1-yl]phenyl]sulfonyl]acetamide;

N-[[4-[3-(difluoromethyl)-5-(3-fluoro-4-methoxyphenyl)-1H-pyrazol-1-yl]phenyl]sulfonyl]propanamide;

N-[[4-[3-(difluoromethyl)-5-(3-fluoro-4-methoxyphenyl)-1H-pyrazol-1-yl]phenyl]sulfonyl]butanamide;

N-[[4-[1,5-dimethyl)-3-phenyl-1H-pyrazol-4-yl]phenyl]sulfonyl]acetamide;

2-hydroxy-3-[[[4-(5-methyl-3-phenylisoxazol-4-yl)phenyl]sulfonyl]amino]-3-oxopropanoic acid;

2-hydroxy-N-[[4-(5-methyl-3-phenylisoxazol-4-yl)phenyl]sulfonyl]propanamide

α-hydroxy-N-[[4-(5-methyl-3-phenylisoxazol-4-yl)phenyl]sulfonyl]benzeneethanamide;

N-[[4-(5-methyl-3-phenylisoxazol-4-yl)phenyl]sulfonyl]benzeneethanamide;

N-[[4-[3-(3-fluorophenyl)-5-methylisoxazol-4-yl]phenyl]sulfonyl]acetamide;

2-methyl-N-[[4-(5-methyl-3-phenylisoxazol-4-yl)phenyl]sulfonyl]propanamide;

N-[[4-(5-methyl-3-phenylisoxazol-4-yl)phenyl]sulfonyl]propanamide;

N-[[4-(5-methyl-3-phenylisoxazol-4-yl)phenyl]sulfonyl]benzamide;

2,2-dimethyl-N-[[4-(5-methyl-3-phenylisoxazol-4-yl)phenyl]sulfonyl]propanamide;

N-[[4-(5-methyl-3-phenylisoxazol-4-yl)phenyl]sulfonyl]butanamide;

N-[[4-(5-methyl-3-phenylisoxazol-4-yl)phenyl]sulfonyl]pentanamide;

N-[[4-(5-methyl-3-phenylisoxazol-4-yl)phenyl]sulfonyl]hexanamide;

3-methoxy-N-[[4-(5-methyl-3-phenylisoxazol-4-yl)phenyl]sulfonyl]propanamide;

2-ethoxy-N-[[4-(5-methyl-3-phenylisoxazol-4-yl)phenyl]sulfonyl]acetamide;

N-[[4-[5-methyl-3-phenylisoxazol-4-yl]phenyl]sulfonyl]acetamide;

N-[[4-[5-(4-chlorophenyl)-3-(trifluoromethyl)-1H-pyrazol-1-yl]phenyl]sulfonyl]propanamide;

N-[[4-[5-(4-chlorophenyl)-3-(trifluoromethyl)-1H-pyrazol-1-yl]phenyl]sulfonyl]butanamide;

N-[[4-[5-(4-chlorophenyl)-3-(trifluoromethyl)-1H-pyrazol-1-yl]phenyl]sulfonyl]acetamide;

N-[[4-[3-(difluoromethyl)-6-fluoro-1,5-dihydro-7-methoxy-[2]benzothiopyrano[4,3-c]pyrazol-1-yl]phenyl]sulfonyl]acetamide;

N-[[4-[6-fluoro-1,5-dihydro-7-methoxy-3-(trifluoromethyl)-[2]benzothiopyrano[4,3-c]pyrazol-1-yl]phenyl]sulfonyl]acetamide;

N-[[4-[3-(difluoromethyl)-5-(3-fluoro-4-methoxyphenyl)-1H-pyrazol-1-yl]phenyl]sulfonyl]acetamide;

N-[[4-(2-methyl-4-phenyloxazol-5-yl)phenyl]sulfonyl]acetamide;

methyl [[[4-(5-methyl-3-phenylisoxazol-4-yl)phenyl]sulfonyl]amino]oxoacetate;

2-methoxy-N-[[4-(5-methyl-3-phenylisoxazol-4-yl)phenyl]sulfonyl]acetamide;

N-[[4-[5-(difluoromethyl)-3-phenylisoxazol-4-yl]phenyl]sulfonyl]propanamide;

N-[[4-[5-(difluoromethyl)-3-phenylisoxazol-4-yl]phenyl]sulfonyl]butanamide;

4-[[[4-(5-methyl-3-phenylisoxazol-4-yl)phenyl]sulfonyl]amino]-4-oxobutanoic acid;

N-[[4-(5-methyl-3-phenylisoxazol-4-yl)phenyl]sulfonyl]formamide;

1,1-dimethylethyl N-[[4-(5-methyl-3-phenylisoxazol-4-yl)phenyl]sulfonyl]carbamate;

N-[[4-(5-methyl-3-phenylisoxazol-4-yl)phenyl]sulfonyl]glycine;

2-amino-N-[[4-(5-methyl-3-phenylisoxazol-4-yl)phenyl]sulfonyl]acetamide;

2-(acetylamino)-N-[[4-(5-methyl-3-phenylisoxazol-4-yl)phenyl]sulfonyl]acetamide;

methyl 4-[[[4-(5-methyl-3-phenylisoxazol-4-yl)phenyl]sulfonyl]amino]-4-oxobutanoate;

N-[[4-(5-methyl-3-phenylisoxazol-4-yl)phenyl]sulfonyl]carbamate;

N-acetyl-N-[[4-(5-methyl-3-phenylisoxazol-4-yl)phenyl]sulfonyl]glycine, ethyl ester;

4-[[[4-(5-methyl-3-phenylisoxazol-4-yl)phenyl]sulfonyl]amino]-4-oxobutanoic acid;

N-[[4-[5-(4-methylphenyl)-3-(trifluoromethyl)-1H-pyrazol-1-yl]phenyl]sulfonyl]acetamide;

methyl 3-[[[4-(5-methyl-3-phenylisoxazol-4-yl)phenyl]sulfonyl]amino]-3-oxopropanoate;

4-[5-(3-bromo-5-fluoro-4-methoxyphenyl)-2-(trifluoromethyl)oxazol-4-yl]-N-methylbenzenesulfonamide;

N-(1,1-dimethylethyl)-4-(5-methyl-3-phenylisoxazol-4-yl)benzenesulfonamide;

4-[5-(4-fluorophenyl)-3-(trifluoromethyl)-1H-pyrazol-1-yl]-N-methylbenzenesulfonamide;

N-methyl-4-(5-methyl-3-phenylisoxazol-4-yl)benzenesulfonamide;

N-[[4-[5-(hydroxymethyl)-3-phenylisoxazol-4-yl]phenyl]sulfonyl]acetamide;

N-[[4-[5-(acetoxymethyl)-3-phenylisoxazol-4-yl]phenyl]sulfonyl]acetamide;

1,1-dimethylethyl-N-[2-[[[4-(5-methyl-3-phenylisoxazol-4-yl)phenyl]sulfonyl]amino]-2-oxoethyl]carbamate;

N-[[4-[2-(3-chloro-4-fluorophenyl)cyclopenten-1-yl]phenyl]sulfonyl]acetamide;

4-[2-(4-fluorophenyl)-1H-pyrrol-1-yl]-N-methylbenzenesulfonamide;

4-[2-(4-fluorophenyl)cyclopenten-1-yl]-N-methylbenzenesulfonamide;

N-[[4-[3-(4-fluorophenyl)-2,3-dihydro-2-oxofuran-4-yl]pheny]sulfonyl]acetamide;

N-[[4-(3-phenyl-2,3-dihydro-2-oxofuran-4-yl)pheny]sulfonyl]acetamide;

N-[[4-[3,4-dimethyl-1-phenyl-1H-pyrazol-5-yl]phenyl]sulfonyl]propanamide;

N-[[4-[2-(2-methylpyridin-3-yl)-4-trifluoromethylimidazol-1-yl]phenyl]sulfonyl]propanamide;

N-[[4-[3-(4-fluorophenyl)-2,3-dihydro-2-oxofuran-4-yl]pheny]sulfonyl]propanamide; and N-[[4-(3-phenyl-2,3-dihydro-2-oxofuran-4-yl)pheny]sulfonyl]propanamide.

A preferred family of specific compounds of particular interest within Formulas I–III consists of compounds as follows:

N-[[4-[2-(2-methylpyridin-6-yl)-4-(trifluoromethyl)-1H-imidazol-1-yl]phenyl]sulfonyl]acetamide, sodium salt;

N-[[4-[2-(2-methylpyridin-6-yl)-4-(trifluoromethyl)-1H-imidazol-1-yl]phenyl]sulfonyl]propanamide, sodium salt;

N-[[4-[2-(2-methylthiazol-4-yl)-4-(trifluoromethyl)-1H-imidazol-1-yl]phenyl]sulfonyl]acetamide, sodium salt;

N-[[4-[2-(2-methylthiazol-4-yl)-4-(trifluoromethyl)-1H-imidazol-1-yl]phenyl]sulfonyl]propanamide, sodium salt;

N-[[4-[2-(4-methylthiazol-2-yl)-4-(trifluoromethyl)-1H-imidazol-1-yl]phenyl]sulfonyl]acetamide, sodium salt;

N-[[4-[2-(4-methylthiazol-2-yl)-4-(trifluoromethyl)-1H-imidazol-1-yl]phenyl]sulfonyl]propanamide, sodium salt;

N-[[4-[2-(3-pyridinyl)-4-(trifluoromethyl)-1H-imidazol-1-yl]phenyl]sulfonyl]acetamide, sodium salt;

N-[[4-[2-(5-methylpyridin-3-yl)-4-(trifluoromethyl)-1H-imidazol-1-yl]phenyl]sulfonyl]acetamide, sodium salt;

N-[[4-[2-(2-methylpyridin-3-yl)-4-(trifluoromethyl)-1H-imidazol-1-yl]phenyl]sulfonyl]acetamide, sodium salt;

N-[[4-[2-(5-methylpyridin-3-yl)-4-(trifluoromethyl)-1H-imidazol-1-yl]phenyl]sulfonyl]butanamide, sodium salt;

N-[[4-[2-(2-methylpyridin-3-yl)-4-(trifluoromethyl)-1H-imidazol-1-yl]phenyl]sulfonyl]butanamide, sodium salt;

N-[[4-[2-(3-chloro-5-methylphenyl)-4-(trifluoromethyl)-1H-imidazol-1-yl]phenyl]sulfonyl]acetamide, sodium salt;

N-[[4-[3-(difluoromethyl)-5-(3-fluoro-4-methoxyphenyl)-1H-pyrazol-1-yl]phenyl]sulfonyl]propanamide, sodium salt;

N-[[4-[3-(difluoromethyl)-5-(3-fluoro-4-methoxyphenyl)-1H-pyrazol-1-yl]phenyl]sulfonyl]butanamide, sodium salt;

N-[[4-[1,5-dimethyl)-3-phenyl-1H-pyrazol-4-yl]phenyl]sulfonyl]acetamide, sodium salt;

2-hydroxy-3-[[[4-(5-methyl-3-phenylisoxazol-4-yl)phenyl]sulfonyl]amino]-3-oxopropanoate, sodium salt;

2-hydroxy-N-[[4-(5-methyl-3-phenylisoxazol-4-yl)phenyl]sulfonyl]propanamide, sodium salt;

α-hydroxy-N-[[4-(5-methyl-3-phenylisoxazol-4-yl)phenyl]sulfonyl]benzeneethanamide, sodium salt;

N-[[4-(5-methyl-3-phenylisoxazol-4-yl)phenyl]sulfonyl]benzeneethanamide, sodium salt;

N-[[4-[3-(3-fluorophenyl)-5-methylisoxazol-4-yl]phenyl]sulfonyl]acetamide, sodium salt;

2-methyl-N-[[4-(5-methyl-3-phenylisoxazol-4-yl)phenyl]sulfonyl]propanamide, sodium salt;

N-[[4-(5-methyl-3-phenylisoxazol-4-yl)phenyl]sulfonyl]propanamide, sodium salt;

N-[[4-(5-methyl-3-phenylisoxazol-4-yl)phenyl]sulfonyl]benzamide, sodium salt;

2,2-dimethyl-N-[[4-(5-methyl-3-phenylisoxazol-4-yl)phenyl]sulfonyl]propanamide, sodium salt;

N-[[4-(5-methyl-3-phenylisoxazol-4-yl)phenyl]sulfonyl]butanamide, sodium salt;

N-[[4-(5-methyl-3-phenylisoxazol-4-yl)phenyl]sulfonyl]pentanamide, sodium salt;

N-[[4-(5-methyl-3-phenylisoxazol-4-yl)phenyl]sulfonyl]hexanamide, sodium salt;

3-methoxy-N-[[4-(5-methyl-3-phenylisoxazol-4-yl)phenyl]sulfonyl]propanamide, sodium salt;

2-ethoxy-N-[[4-(5-methyl-3-phenylisoxazol-4-yl)phenyl]sulfonyl]acetamide, sodium salt;

N-[[4-[5-methyl-3-phenylisoxazol-4-yl]phenyl]sulfonyl]acetamide, potassium salt;

N-[[4-[5-(4-chlorophenyl)-3-(trifluoromethyl)-1H-pyrazol-1-yl]phenyl]sulfonyl]propanamide, sodium salt;

N-[[4-[5-(4-chlorophenyl)-3-(trifluoromethyl)-1H-pyrazol-1-yl]phenyl]sulfonyl]butanamide, sodium salt;

N-[[4-[5-(4-chlorophenyl)-3-(trifluoromethyl)-1H-pyrazol-1-yl]phenyl]sulfonyl]acetamide, sodium salt;

N-[[4-[3-(difluoromethyl)-6-fluoro-1,5-dihydro-7-methoxy-[2]benzothiopyrano[4,3-c]pyrazol-1-yl]phenyl]sulfonyl]acetamide, sodium salt;

N-[[4-[6-fluoro-1,5-dihydro-7-methoxy-3-(trifluoromethyl)-[2]benzothiopyrano[4,3-c]pyrazol-1-yl]phenyl]sulfonyl]acetamide, sodium salt;

N-[[4-[3-(difluoromethyl)-5-(3-fluoro-4-methoxyphenyl)-1H-pyrazol-1-yl]phenyl]sulfonyl]acetamide, sodium salt;

N-[[4-(2-methyl-4-phenyloxazol-5-yl)phenyl]sulfonyl]acetamide, sodium salt;

methyl [[[4-(5-methyl-3-phenylisoxazol-4-yl)phenyl]sulfonyl]amino]oxoacetate, sodium salt;

2-methoxy-N-[[4-(5-methyl-3-phenylisoxazol-4-yl)phenyl]sulfonyl]acetamide, sodium salt;

N-[[4-[5-(difluoromethyl)-3-phenylisoxazol-4-yl]phenyl]sulfonyl]propanamide, sodium salt;

N-[[4-[5-(difluoromethyl)-3-phenylisoxazol-4-yl]phenyl]sulfonyl]butanamide, sodium salt;

4-[[[4-(5-methyl-3-phenylisoxazol-4-yl)phenyl]sulfonyl]amino]-4-oxobutanoic acid, sodium salt;

N-[[4-(5-methyl-3-phenylisoxazol-4-yl)phenyl]sulfonyl]formamide, sodium salt;

1,1-dimethylethyl N-[[4-(5-methyl-3-phenylisoxazol-4-yl)phenyl]sulfonyl]carbamate, sodium salt;

N-[[4-(5-methyl-3-phenylisoxazol-4-yl)phenyl]sulfonyl]glycine, sodium salt;

2-amino-N-[[4-(5-methyl-3-phenylisoxazol-4-yl)phenyl]sulfonyl]acetamide, sodium salt;

2-(acetylamino)-N-[[4-(5-methyl-3-phenylisoxazol-4-yl)phenyl]sulfonyl]acetamide, sodium salt;

methyl 4-[[[4-(5-methyl-3-phenylisoxazol-4-yl)phenyl]sulfonyl]amino]-4-oxobutanoate, sodium salt;

N-[[4-(5-methyl-3-phenylisoxazol-4-yl)phenyl]sulfonyl]carbamate, sodium salt;

4-[[[4-(5-methyl-3-phenylisoxazol-4-yl)phenyl]sulfonyl]amino]-4-oxobutanoic acid, sodium salt;

N-[[4-[5-(4-methylphenyl)-3-(trifluoromethyl)-1H-pyrazol-1-yl]phenyl]sulfonyl]acetamide, sodium salt;

methyl 3-[[[4-(5-methyl-3-phenylisoxazol-4-yl)phenyl]sulfonyl]amino]-3-oxopropanoate, sodium salt;

N-[[4-[5-(hydroxymethyl)-3-phenylisoxazol-4-yl]phenyl]sulfonyl]acetamide, sodium salt;

N-[[4-[5-(acetoxymethyl)-3-phenylisoxazol-4-yl]phenyl]sulfonyl]acetamide, sodium salt;

1,1-dimethylethyl-N-[2-[[[4-(5-methyl-3-phenylisoxazol-4-yl)phenyl]sulfonyl]amino]-2-oxoethyl]carbamate, sodium salt;

N-[[4-[2-(3-chloro-4-fluorophenyl) cyclopenten-1-yl]phenyl]sulfonyl]acetamide, sodium salt; and N-[[4-[3-(4-fluorophenyl)-2,3-dihydro-2-oxofuran-4-yl]pheny]sulfonyl]acetamide, sodium salt;

N-[[4-(3-phenyl-2,3-dihydro-2-oxofuran-4-yl)pheny]sulfonyl]acetamide, sodium salt;

N-[[4-[3,4-dimethyl-1-phenyl-1H-pyrazol-5-yl]phenyl]sulfonyl]propanamide, sodium salt;

N-[[4-[2-(2-methylpyridin-3-yl)-4-trifluoromethylimidazol-1-yl]phenyl]sulfonyl]propanamide, sodium salt;

N-[[4-[3-(4-fluorophenyl)-2,3-dihydro-2-oxofuran-4-yl]pheny]sulfonyl]propanamide, sodium salt; and N-[[4-(3-phenyl-2,3-dihydro-2-oxofuran-4-yl)pheny]sulfonyl]propanamide, sodium salt.

The term "hydrido" denotes a single hydrogen atom (H). This hydrido radical may be attached, for example, to an oxygen atom to form a hydroxyl radical or two hydrido radicals may be attached to a carbon atom to form a methylene (—CH$_2$—) radical. Where used, either alone or within other terms such as "haloalkyl", "alkylsulfonyl", "alkoxyalkyl" and "hydroxyalkyl", the term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about six carbon atoms. Examples of such radicals include methyl, ethyl, n-propyl, isopropyl, n-butyl, isobutyl, sec-butyl, tert-butyl, pentyl, iso-amyl, hexyl and the like. The term "alkenyl" embraces linear or branched radicals having at least one carbon-carbon double bond of two to about twenty carbon atoms or, preferably, two to about twelve carbon atoms. More preferred alkenyl radicals are "lower alkenyl" radicals having two to about six carbon atoms. Examples of alkenyl radicals include ethenyl, propenyl, allyl, propenyl, butenyl and 4-methylbutenyl. The term "alkynyl" denotes linear or branched radicals having at least one carbon-carbon triple bond, and having two to about twenty carbon atoms or, preferably, two to about twelve carbon atoms. More preferred alkynyl radicals are "lower alkynyl" radicals having two to about ten carbon atoms. Most preferred are lower alkynyl radicals having two to about six carbon atoms. Examples of such radicals include propargyl, butynyl, and the like. The terms "alkenyl" and "lower alkenyl", embrace radicals having "cis" and "trans" orientations, or alternatively, "E" and "Z" orientations. The term "cycloalkyl" embraces saturated carbocyclic radicals having three to about twelve carbon atoms. More preferred cycloalkyl radicals are "lower cycloalkyl" radicals having three to about eight carbon atoms. Examples of such radicals include cyclopropyl, cyclobutyl, cyclopentyl and cyclohexyl. The term "cycloalkenyl" embraces partially unsaturated carbocyclic radicals having three to twelve carbon atoms. More preferred cycloalkenyl radicals are "lower cycloalkenyl" radicals having four to about eight carbon atoms. Examples of such radicals include cyclobutenyl, cyclopentenyl and cyclohexenyl. The term "halo" means halogens such as fluorine, chlorine, bromine or iodine. The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having one to six carbon atoms. Examples of haloalkyl radicals include fluoromethyl, difluoromethyl, trifluoromethyl, chloromethyl, dichloromethyl, trichloromethyl, trichloromethyl, pentafluoroethyl, heptafluoropropyl, difluorochloromethyl, dichlorofluoromethyl, difluoroethyl, difluoropropyl, dichloroethyl and dichloropropyl. The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. The terms "alkoxy" and "alkyloxy" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. The term "alkoxyalkyl" embraces alkyl radicals having one or more alkoxy radicals attached to the alkyl radical, that is, to form monoalkoxyalkyl and dialkoxyalkyl radicals. The "alkoxy" radicals may be further substituted with one or more halo atoms, such as fluoro, chloro or bromo, to provide haloalkoxy radicals. More preferred haloalkoxy radicals are "lower haloalkoxy" radicals having one to six carbon atoms and one or more halo radicals. Examples of such radicals include fluoromethoxy, chloromethoxy, trifluoromethoxy, trifluoroethoxy, fluoroethoxy and fluoropropoxy. The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl. Aryl moieties may also be substituted at a substitutable position with one or more substituents selected independently from alkyl, alkoxyalkyl, alkylaminoalkyl, carboxyalkyl, alkoxycarbonylalkyl, aminocarbonylalkyl, alkoxy, aralkoxy, hydroxyl, amino, halo, nitro, alkylamino, acyl, cyano, carboxy, aminocarbonyl, alkoxycarbonyl and aralkoxycarbonyl. The term "heterocyclyl" embraces saturated, partially unsaturated and unsaturated heteroatom-containing ring-shaped radicals, where the heteroatoms may be selected from nitrogen, sulfur and oxygen. Examples of saturated heterocyclyl radicals include saturated 3 to 6-membered heteromonocylic group containing 1 to 4 nitrogen atoms (e.g. pyrrolidinyl, imidazolidinyl, piperidino, piperazinyl, etc.); saturated 3 to 6-membered heteromonocyclic group containing 1 to 2 oxygen atoms and 1 to 3 nitrogen atoms (e.g. morpholinyl, etc.); saturated 3 to 6-membered heteromonocyclic group containing 1 to 2 sulfur atoms and 1 to 3 nitrogen atoms (e.g., thiazolidinyl, etc.). Examples of partially unsaturated heterocyclyl radicals include dihydrothiophene, dihydropyran, dihydrofuran and dihydrothiazole. Heterocyclyl radiclas may include a pentavalent nitrogen, such as in tetrazolium and pyridinium radicals. The term "heteroaryl" embraces unsaturated heterocyclyl radicals. Examples of heteroaryl radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g. 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl group containing 1 to 2 oxygen atoms and 1 to 3 nitrogen atoms (e.g. benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like. The term "heteroaryl" also embraces radicals where heterocyclyl radicals are fused with aryl radicals. Examples of such fused bicyclic radicals include benzofuran, benzothiophene, and the like. Said "heterocyclyl group" may have 1 to 3 substituents such as alkyl, hydroxyl, halo, alkoxy, oxo, amino and alkylamino. The term "alkylthio" embraces radicals containing a linear or branched alkyl radical, of one to about ten carbon atoms attached to a divalent sulfur atom. More preferred alkylthio radicals are "lower alkylthio" radicals having alkyl radicals of one to six carbon atoms. Examples of such lower alkylthio radicals are methylthio, ethylthio, propylthio, butylthio and hexylthio. The term "alkylthioalkyl" embraces radicals containing an alkylthio radical attached through the divalent sulfur atom to an alkyl radical of one to about ten carbon atoms. More preferred alkylthioalkyl radicals are "lower alkylthioalkyl" radicals having alkyl radicals of one to six carbon atoms. Examples of such lower alkylthioalkyl radicals include methylthiomethyl. The term "alkylsulfinyl" embraces radicals containing a linear or branched alkyl radical, of one to about ten carbon atoms, attached to a divalent —S(=O)— radical. More preferred alkylsulfinyl radicals are "lower alkylsulfinyl" radicals having alkyl radicals of one to six carbon atoms. Examples of such lower alkylsulfinyl radicals include methylsulfinyl, ethylsulfinyl, butylsulfinyl and hexylsulfinyl. The term "sulfonyl", whether used alone or linked to other terms such as "alkylsulfonyl", denotes a divalent radical, —SO$_2$—. "Alkylsulfonyl" embraces alkyl radicals attached to a sulfonyl radical, where alkyl is defined as above. More preferred alkylsulfonyl radicals are "lower alkylsulfonyl" radicals having one to six carbon atoms. Examples of such lower alkylsulfonyl radicals include methylsulfonyl, ethylsulfonyl and propylsulfonyl. The "alkylsulfonyl" radicals may be further substituted with one or more halo atoms, such as fluoro, chloro or bromo, to provide haloalkylsulfonyl radicals. The terms "sulfamyl", "aminosulfonyl" and "sulfonamidyl" denote NH$_2$O$_2$S—. The term "acyl" denotes a radical provided by the residue after removal of hydroxyl from an organic acid. Examples of such acyl radicals include alkanoyl and aroyl radicals. Examples of such alkanoyl radicals include formyl, acetyl, propionyl, butyryl, isobutyryl, valeryl, isovaleryl, pivaloyl, hexanoyl, and radicals formed from succinic, glycolic, gluconic, lactic, malic, tartaric, citric, ascorbic, glucuronic, maleic, fumaric, pyruvic, mandelic, pantothenic, β-hydroxybutyric, galactaric and galacturonic acids. The term "aroyl" embraces aryl radicals with a carbonyl radical as defined below. Examples of aroyl include benzoyl, naphthoyl, phenylacetyl, and the like, and the aryl in said aroyl may be additionally substituted, such as in p-hydroxybenzoyl, and salicylyl. The term "carbonyl", whether used alone or with other terms, such as "alkoxycarbonyl", denotes —(C=O)—. The terms "carboxy" or "carboxyl", whether used alone or with other terms, such as "carboxyalkyl", denotes—CO$_2$H. The term "carboxyalkyl" embraces alkyl radicals substituted with a carboxy radical. More preferred are "lower carboxyalkyl" which embrace lower alkyl radicals as defined above, and may be additionally substituted on the alkyl radical with halo. Examples of such lower carboxyalkyl radicals include carboxymethyl, carboxyethyl and carboxypropyl. The term "alkoxycarbonyl" means a radical containing an alkoxy radical, as defined above, attached via an oxygen atom to a carbonyl radical. More preferred are "lower alkoxycarbonyl", radicals with alkyl portions having one to six carbons. Examples of such lower alkoxycarbonyl (ester) radicals include substituted or unsubstituted methoxycarbonyl, ethoxycarbonyl, propoxycarbonyl, butoxycarbonyl and hexyloxycarbonyl. The terms "alkylcarbonyl", "arylcarbonyl" and "aralkylcarbonyl" include radicals having alkyl, hydroxylalkyl, aryl, arylalkyl and aryl-hydroxylalkyl radicals, as defined herein, attached to a carbonyl radical. Examples of such radicals include substituted or unsubstituted methylcarbonyl, ethylcarbonyl, propylcarbonyl, butylcarbonyl, pentylcarbonyl, hydroxymethylcarbonyl, hydroxyethylcarbonyl, phenylcarbonyl, benzylcarbonyl, and phenyl(hydroxymethyl)carbonyl. The term "carboxyalkylcarbonyl" embraces alkylcarbonyl radicals substituted with a carboxy radical. More preferred are "lower carboxyalkylcarbonyl" which embrace lower alkyl radicals as defined above, and may be additionally substituted on the alkyl radical with hydroxyl. Examples of such lower carboxyalkylcarbonyl radicals include carboxymethylcarbonyl, carboxyethylcarbonyl, carboxypropylcarbonyl, HO$_2$C(CHOH)$_4$C(O)—, HO$_2$C(CHOH)$_2$C(O)—, HO$_2$C(CH$_2$)(CHOH)C(O)—, and HO$_2$CCH$_2$C(OH)(CO$_2$H)C(O)—. The term "carboxyalkenylcarbonyl" embraces derivatives of maleic and fumaric acids. Examples of such carboxyalkenylcarbonyl radicals include (Z)-carboxyethenylcarbonyl and (E)-carboxyethenylcarbonyl. The term "aralkyl" embraces aryl-substituted alkyl radicals such as benzyl, diphenylmethyl, triphenylmethyl, phenylethyl, and diphenylethyl. The aryl in said aralkyl may be additionally substituted with halo, alkyl, alkoxy, halkoalkyl and haloalkoxy. The terms benzyl and phenylmethyl are interchangeable. The term "heterocyclylalkyl" embraces saturated and partially unsaturated heterocyclyl-substituted alkyl radicals, such as pyrrolidinylmethyl, and heteroaryl-substituted alkyl radicals, such as pyridylmethyl, quinolylmethyl, thienylmethyl, furylethyl, and quinolylethyl. The heteroaryl in said heteroaralkyl may be additionally substituted with halo, alkyl, alkoxy, halkoalkyl and haloalkoxy. The term "aryloxy" embraces aryl radicals attached through an oxygen atom to other radicals. The term "arylthio" embraces aryl radicals attached to a sulfur atom. The term "aralkoxy" embraces aralkyl radicals attached through an oxygen atom to other radicals. The term "heterocyclyloxy" embraces heterocyclyl radicals attached through an oxygen atom to other radicals. The term "aralkoxyalkyl" embraces aralkoxy radicals attached through an oxygen atom to an alkyl radical. The term "aralkylthio" embraces aralkyl radicals attached to a sulfur atom. The term "aralkylthioalkyl" embraces aralkylthio radicals attached through a sulfur atom to an alkyl radical. The term "aminoalkyl" embraces alkyl radicals substituted with amino radicals. More preferred are "lower aminoalkyl" radicals. Examples of such radicals include aminomethyl, aminoethyl, and the like. The term "alkylamino" denotes amino groups which are substituted with one or two alkyl radicals. Preferred are "lower alkylamino" radicals having alkyl porions having one to six carbon atoms. Suitable lower alkylamino may be monosubstituted N-alkylamino or disubstituted N,N-alkylamino, such as N-methylamino, N-ethylamino, N,N-dimethylamino, N,N-diethylamino or the like. The term "arylamino" denotes amino groups which are substituted with one or two aryl radicals, such as N-phenylamino. The "arylamino" radicals may be further substituted on the aryl ring portion of the radical. The term "aralkylamino" embraces amino groups which are substituted with one or two aralkyl radicals. The terms "N-arylaminoalkyl" and "N-aryl-N-alkyl-aminoalkyl" denote aminoalkyl groups which are substituted with one aryl radical or one aryl and one alkyl radical, respectively. Examples of such radicals include N-phenylaminomethyl and N-phenyl-N-methylaminomethyl. The term "aminocarbonyl" denotes an amide group of the formula —C(=O)NH$_2$. The term "alkylaminocarbonyl" denotes an aminocarbonyl group which has been substituted with one or two alkyl radicals on the amino nitrogen atom. Preferred are "N-alkylaminocarbonyl" and "N,N-dialkylaminocarbonyl" radicals. More preferred are "lower N-alkylaminocarbonyl" and "lower N,N-dialkylaminocarbonyl" radicals with lower alkyl portions as defined above. The term "alkylaminoalkyl" embraces radicals having one or more alkyl radicals attached to an aminoalkyl radical. The term "aryloxyalkyl" embraces radicals having an aryl radicals attached to an alkyl radical through a divalent oxygen atom. The term "arylthioalkyl" embraces radicals having an aryl radicals attached to an alkyl radical through a divalent sulfur atom. "Amino acid residue" means any of the naturally occurring alpha-, beta- and gamma-amino carboxylic acids, including their D and L optical isomers and racemic mixtures thereof, synthetic amino acids, and derivatives of these natural and synthetic amino acids. The amino acid residue is bonded either through an amino or an acid functional group of the amino acid. The naturally occurring amino acids which can be incorporated in the present invention include, but are not limited to, alanine, arginine, asparagine, aspartic acid, cysteine, glutamic acid, glutamine, glycine, histidine, isoleucine, leucine, lysine, methionine, ornithine, phenylalanine, proline, serine, threonine, cyclohexylalanine, tryptophan, tyrosine, valine, β-alanine, and γ-aminobutyric acid. Derivatives of amino acids which can be incorporated in the present invention include, but are not limited to amino acids having protected and modified carboxylic acids, including acid esters and amides, protected amines, and substituted phenyl rings, including but not limited to alkyl, alkoxy and halo substituted tyrosine and phenylalanine.

The present invention comprises a pharmaceutical composition comprising a therapeutically-effective amount of a compound of Formula I in association with at least one pharmaceutically-acceptable carrier, adjuvant or diluent.

The present invention also comprises a method of treating inflammation or inflammation-related disorder in a subject, the method comprising treating the subject having or susceptible to such inflammation or inflammation-related disorder with a compound of Formula I':

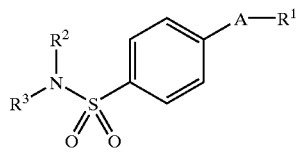

I' wherein A is a ring substituent selected from partially unsaturated heterocyclyl, heteroaryl, cycloalkenyl and aryl, wherein A is optionally substituted at a substitutable position with one or more radicals selected from alkylcarbonyl, formyl, halo, alkyl, haloalkyl, oxo, cyano, nitro, carboxyl, alkoxy, aminocarbonyl, alkoxycarbonyl, carboxyalkyl, cyanoalkyl, hydroxyalkyl, haloalkylsulfonyloxy, alkoxyalkyloxyalkyl, carboxyalkoxyalkyl, cycloalkylalkyl, alkenyl, alkynyl, heterocyclyloxy, alkylthio, cycloalkyl, aryl, heterocyclyl, cycloalkenyl, aralkyl, heterocyclylalkyl, alkylthioalkyl, arylcarbonyl, aralkylcarbonyl, aralkenyl, alkoxyalkyl, arylthioalkyl, aryloxyalkyl, aralkylthioalkyl, aralkoxyalkyl, alkoxycarbonylalkyl, aminocarbonylalkyl, alkylaminocarbonyl, N-arylaminocarbonyl, N-alkyl-N-arylaminocarbonyl, alkylaminocarbonylalkyl, alkylamino, N-arylamino, N-aralkylamino, N-alkyl-N-aralkylamino, N-alkyl-N-arylamino, aminoalkyl, alkylaminoalkyl, N-arylaminoalkyl, N-aralkylaminoalkyl, N-alkyl-N-aralkylaminoalkyl, N-alkyl-N-arylaminoalkyl, aryloxy, aralkoxy, arylthio, aralkylthio, alkylsulfinyl, alkylsulfonyl, aminosulfonyl, alkylaminosulfonyl, N-arylaminosulfonyl, arylsulfonyl, and N-alkyl-N-arylaminosulfonyl; wherein $R^1$ is selected from heterocyclyl, cycloalkyl, cycloalkenyl and aryl, wherein $R^1$ is optionally substituted at a substitutable position with one or more radicals selected from alkyl, haloalkyl, cyano, carboxyl, alkoxycarbonyl, hydroxyl, hydroxyalkyl, haloalkoxy, amino, alkylamino, arylamino, nitro, alkoxyalkyl, alkylsulfinyl, halo, alkoxy and alkylthio; wherein $R^2$ is selected from hydrido and alkoxycarbonylalkyl; and wherein $R^3$ is selected from alkyl, carboxyalkyl, acyl, alkoxycarbonyl, heteroarylcarbonyl, alkoxycarbonylalkylcarbonyl, alkoxycarbonylcarbonyl, amino acid residue, and alkylcarbonylaminoalkylcarbonyl; or a pharmaceutically-acceptable salt thereof.

The method of the present invention also includes prophylactic treatment. A preferred method of the invention is the administration of water soluble compounds of Formulas I–III via injection.

Also included in the family of compounds of Formula I are the stereoisomers thereof. Compounds of the present invention can possess one or more asymmetric carbon atoms and are thus capable of existing in the form of optical isomers as well as in the form of racemic or nonracemic mixtures thereof. Accordingly, some of the compounds of this invention may be present in racemic mixtures which are also included in this invention. The optical isomers can be obtained by resolution of the racemic mixtures according to conventional processes, for example by formation of diastereoisomeric salts by treatment with an optically active acid or base. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting an amine functionality of precursors to compounds of Formula I with an optically pure acid in an activated form or an optically pure isocyanate. Alternatively, diastereomeric derivatives can be prepared by reacting a carboxyl functionality of precursors to compounds of Formula I with an optically pure amine base. The synthesized diastereoisomers can be separated by conventional means such as chromatography, distillation, crystallization or sublimation, and then hydrolyzed to deliver the enantiomerically pure compound. The optically active compounds of Formula I can likewise be obtained by utilizing optically active starting materials. These isomers may be in the form of a free acid, a free base, an ester or a salt.

Also included in the family of compounds of Formula I are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclyl, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, β-hydroxybutyric, galactaric and galacturonic acid. Suitable pharmaceutically-acceptable base addition salts of compounds of Formula I include metallic salts and organic salts. More preferrred metallic salts include, but are not limited to appropriate alkali metal (group Ia) salts, alkaline earth metal (group IIa) salts and other physiological acceptable metals. Such salts can be made from aluminum, calcium, lithium, magnesium, potassium, sodium and zinc. Preferred organic salts can be made from tertiary amines and quanternary ammonium salts, including in part, trometamine, diethylamine, N,N'-dibenzylethylenediamine, chloroprocaine, choline, diethanolamine, ethylenediamine, meglumine (N-methylglucamine) and procaine. All of these salts may be prepared by conventional means from the corresponding compound of Formulas I–III by reacting, for example, the appropriate acid or base with the compound of Formulas I–III.

GENERAL SYNTHETIC PROCEDURES

The cyclooxygenase-2 inhibitor prodrugs of the invention can be synthesized according to the following procedures of Schemes I–XVII, wherein the $R^1$–$R^8$ substituents are as defined for Formulas I–III, above, except where further noted.

Scheme I

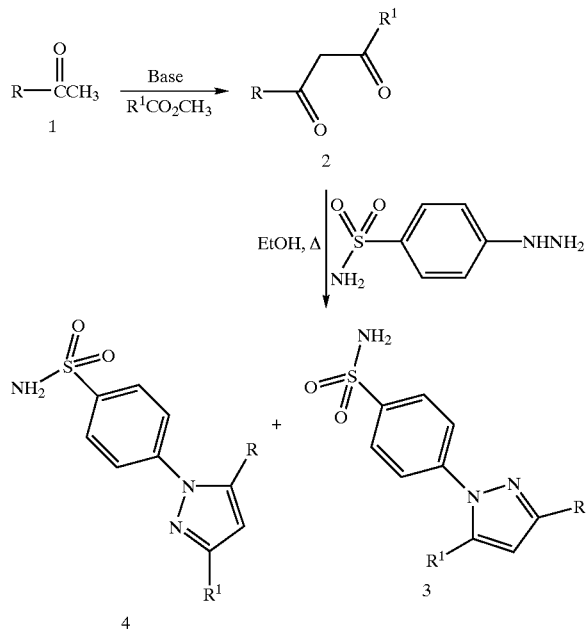

Synthetic Scheme I shows the preparation of cyclooxygenase-2 inhibitor compounds, as described in WO95/15316, which is incorporated by reference. In step 1, ketone 1 is treated with a base, preferably NaOMe or NaH, and an ester, or ester equivalent, to form the intermediate diketone 2 (in the enol form) which is used without further purification. In step 2, diketone 2 in an anhydrous protic solvent, such as absolute ethanol or acetic acid, is treated with the hydrochloride salt or the free base of a substituted hydrazine at reflux to afford a mixture of pyrazoles 3 and 4. Recrystallization or chromatography affords 3 usually as a solid. Similar pyrazoles can be prepared by methods described in U.S. Pat. Nos. 5,401,765, 5,434,178, 4,146,721, 5,051,518, 5,134,142 and 4,914,121 which also are incorporated by reference.

Scheme II

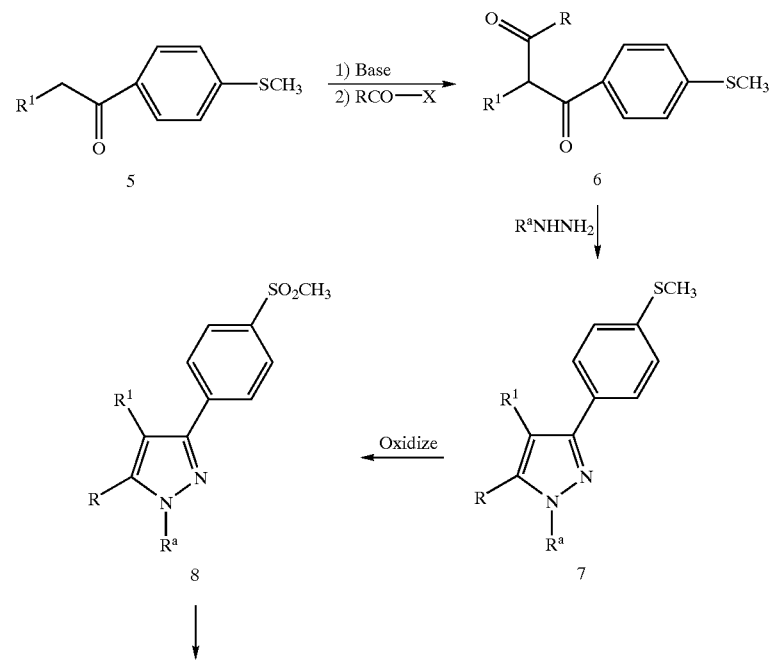

-continued

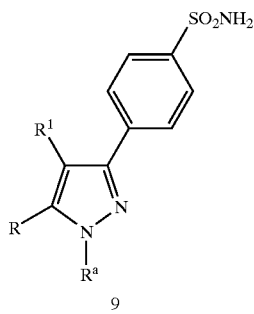
9

Scheme II shows the four step procedure for forming cyclooxygenase-2 inhibitor pyrazoles 8 as described in U.S. Pat. No. 5,486,534 (where $R_a$ is hydrido or alkyl) from ketones 5. In step 1, ketone 5 is reacted with a base, such as lithium bis(trimethylsilyl)amide or lithium diisopropylamide (LDA) to form the anion. In step 2, the anion is reacted with an acetylating reagent to provide diketone 6. In step 3, the reaction of diketone 6 with hydrazine or a substituted hydrazine, gives pyrazole 7. In step 4, the pyrazole 7 is oxidized with an oxidizing reagent, such as Oxone® (potassium peroxymonosulfate), 3-chloroperbenzoic acid (MCPBA) or hydrogen peroxide, to give a mixture of the desired 3-(alkylsulfonyl)phenyl-pyrazole 8 and the 5-(alkylsulfonyl)phenyl-pyrazole isomer. Sulfonamides 9 can be prepared such as by the Huang method [*Tet. Lett.*, 35, 7201–04 (1994)].

Alternatively, diketone 6 can be formed from ketone 5 by treatment with a base, such as sodium hydride, in a solvent, such as dimethylformamide, and further reacting with a nitrile to form an aminoketone. Treatment of the aminoketone with acid forms the diketone 6. Similar pyrazoles can be prepared by methods described in U.S. Pat. No. 3,984,431 which is incorporated by reference.

Scheme III

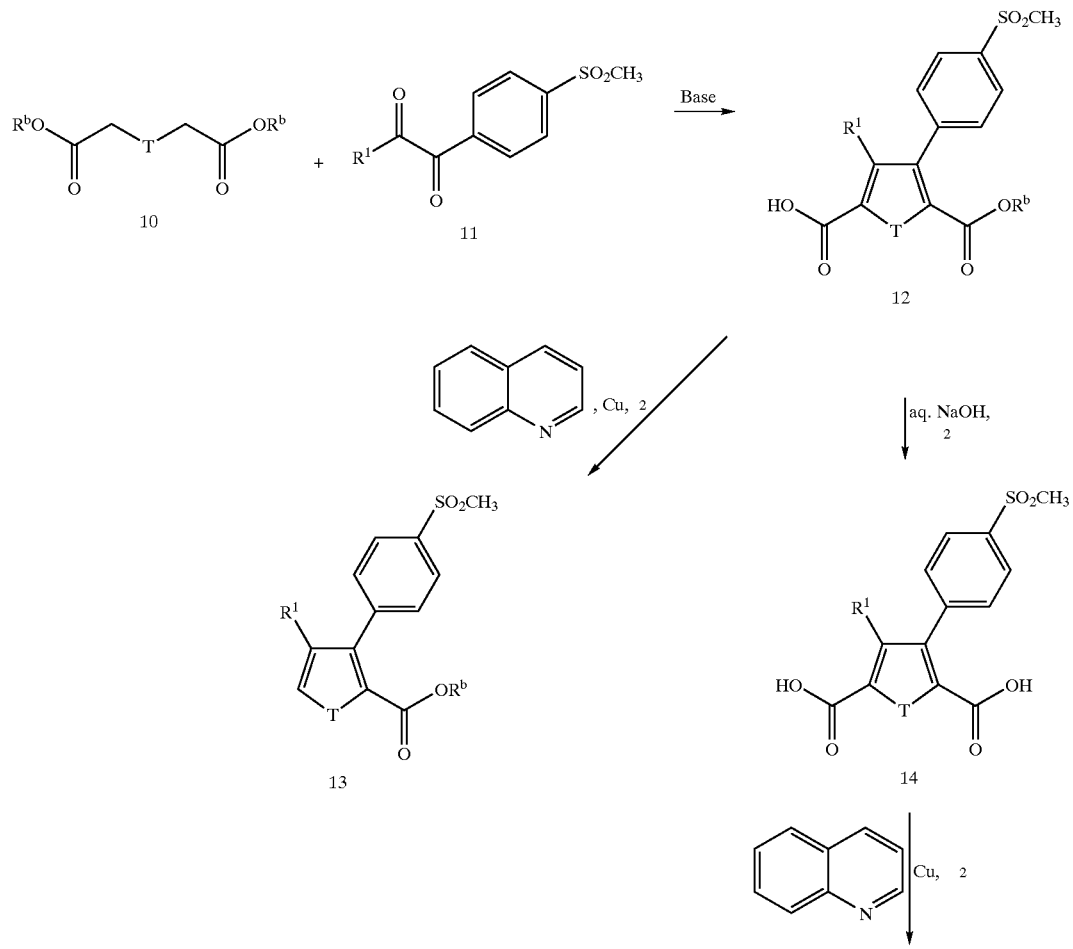

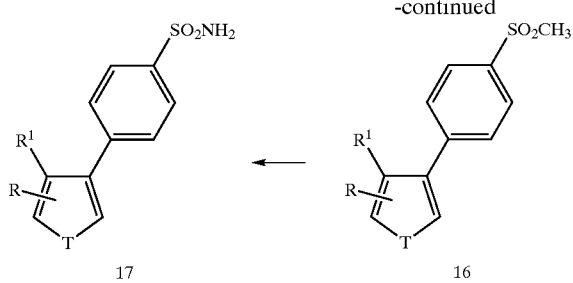
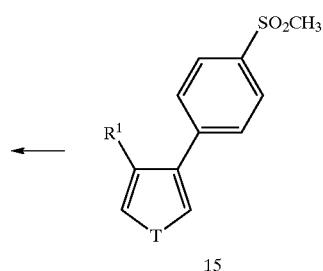

Cyclooxygenase-2 inhibitor diaryl/heteroaryl thiophenes (where T is S, and $R^b$ is alkyl) can be prepared by the methods described in U.S. Pat. Nos. 4,427,693, 4,302,461, 4,381,311, 4,590,205, and 4,820,827, and PCT documents WO 95/00501 and WO94/15932, which are incorporated by reference. Similar pyrroles (where T is N), furanones and furans (where T is O) can be prepared by methods described in PCT documents WO 95/00501 and WO94/15932.

Cyclooxygenase-2 inhibitor diaryl/heteroaryl oxazoles can be prepared by the methods described in U.S. Pat. Nos. 5,380,738, 3,743,656, 3,644,499 and 3,647,858, and PCT documents WO 95/00501 and WO94/27980, which are incorporated by reference.

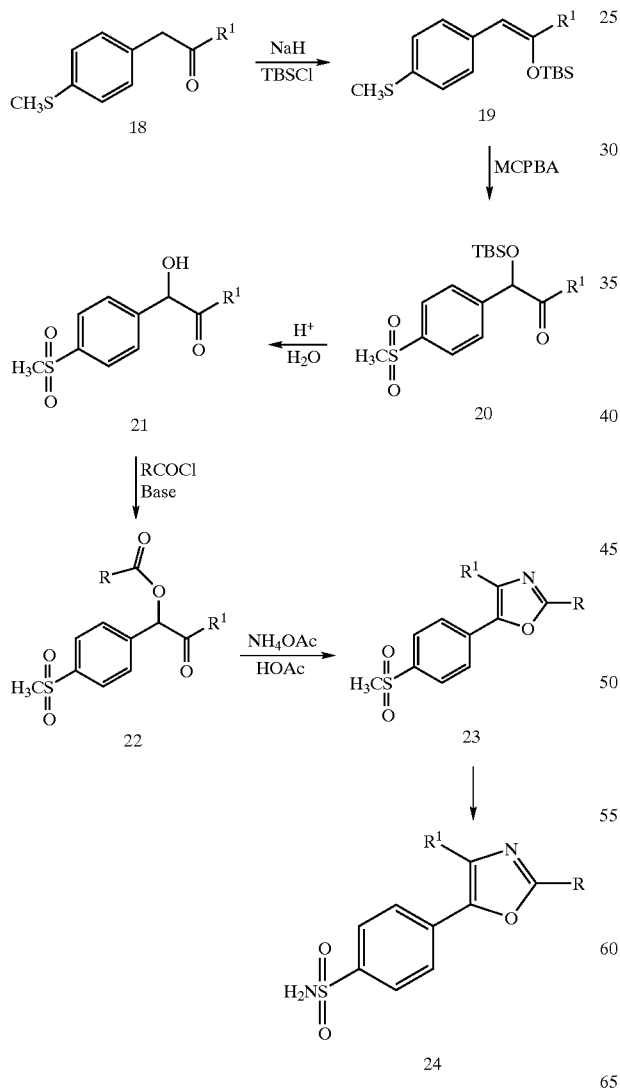

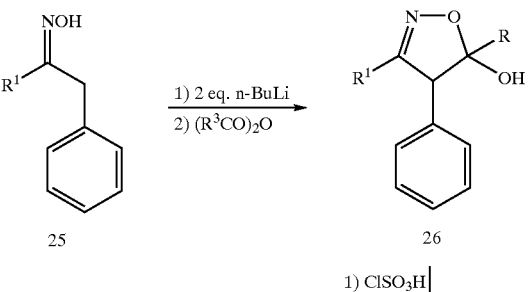

Cyclooxygenase-2 inhibitor diaryl/heteroaryl isoxazoles can be prepared by the methods described in PCT application Ser. No. US96/01869, PCT documents WO92/05162, and WO92/19604, and European Publication EP 26928, which are incorporated by reference. Sulfonamides 27 can be formed from the hydrated isoxazole 26 in a two step procedure. First, hydrated isoxazole 26 is treated at about 0° C. with two or three equivalents of chlorosulfonic acid to form the corresponding sulfonyl chloride. In step two, the sulfonyl chloride thus formed is treated with concentrated ammonia to provide the sulfonamide derivative 27.

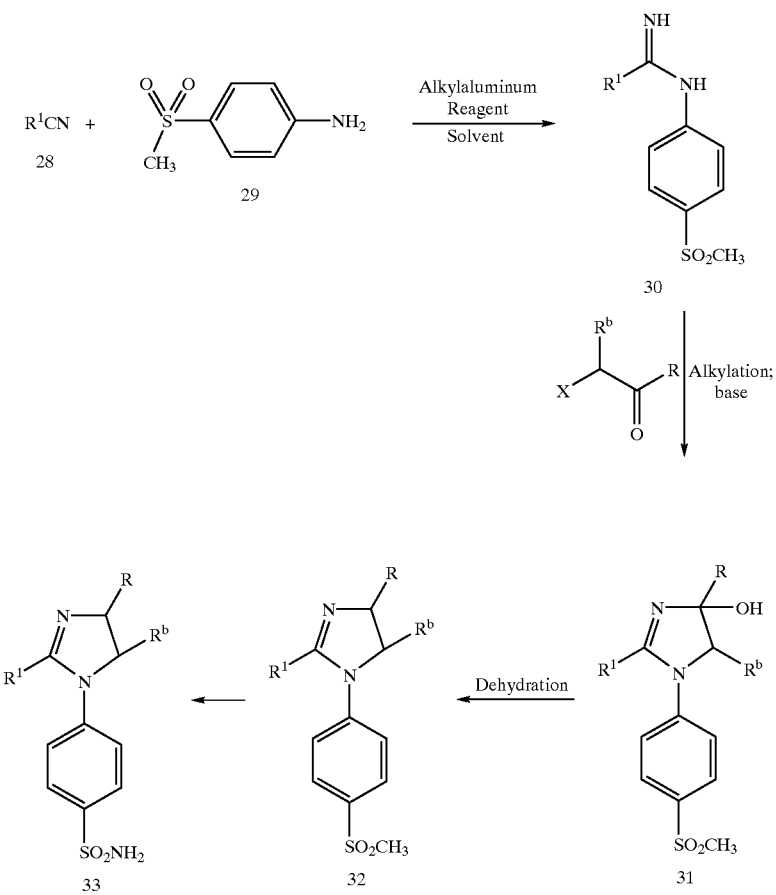

Scheme VI shows a three step preparation of the cyclooxygenase-2 inhibitor imidazoles 33. In step 1, the reaction of substituted nitriles ($R^1CN$) 28 with primary phenylamines 29 in the presence of alkylaluminum reagents such as trimethylaluminum, triethylaluminum, dimethylaluminum chloride, diethylaluminum chloride in the presence of inert solvents such as toluene, benzene, and xylene, gives amidines 30. In step 2, the reaction of amidine 30 with 2-haloketones (where X is Br or Cl) in the presence of bases, such as sodium bicarbonate, potassium carbonate, sodium carbonate, potassium bicarbonate or hindered tertiary amines such as N,N'-diisopropylethylamine, gives the 4,5-dihydroimidazoles 31 (where $R^b$ is alkyl). Some of the suitable solvents for this reaction are isopropanol, acetone and dimethylformamide. The reaction may be carried out at temperatures of about 20° C. to about 90° C. In step 3, the 4,5-dihydroimidazoles 31 may be dehydrated in the presence of an acid catalyst such as 4-toluenesulfonic acid or mineral acids to form the 1,2-disubstituted imidazoles 32 of the invention. Suitable solvents for this dehydration step are e.g., toluene, xylene and benzene. Trifluoroacetic acid can be used as solvent and catalyst for this dehydration step. Sulfonamides 33 can be prepared such as by the Huang method [*Tet. Lett.*, 35, 7201–04 (1994)].

In some cases (e.g., where R=methyl or phenyl) the intermediate 31 may not be readily isolable. The reaction, under the conditions described above, proceeds to give the targeted imidazoles directly.

Similarly, imidazoles can be prepared having the sulfonylphenyl moiety attached at position 2 and $R^1$ attached at the nitrogen atom at position 1. Diaryl/heteroaryl imidazoles can be prepared by the methods described in U.S. Pat. Nos. 4,822,805 and PCT documents WO 93/14082 and WO96/03388, which are incorporated by reference.

Scheme VII

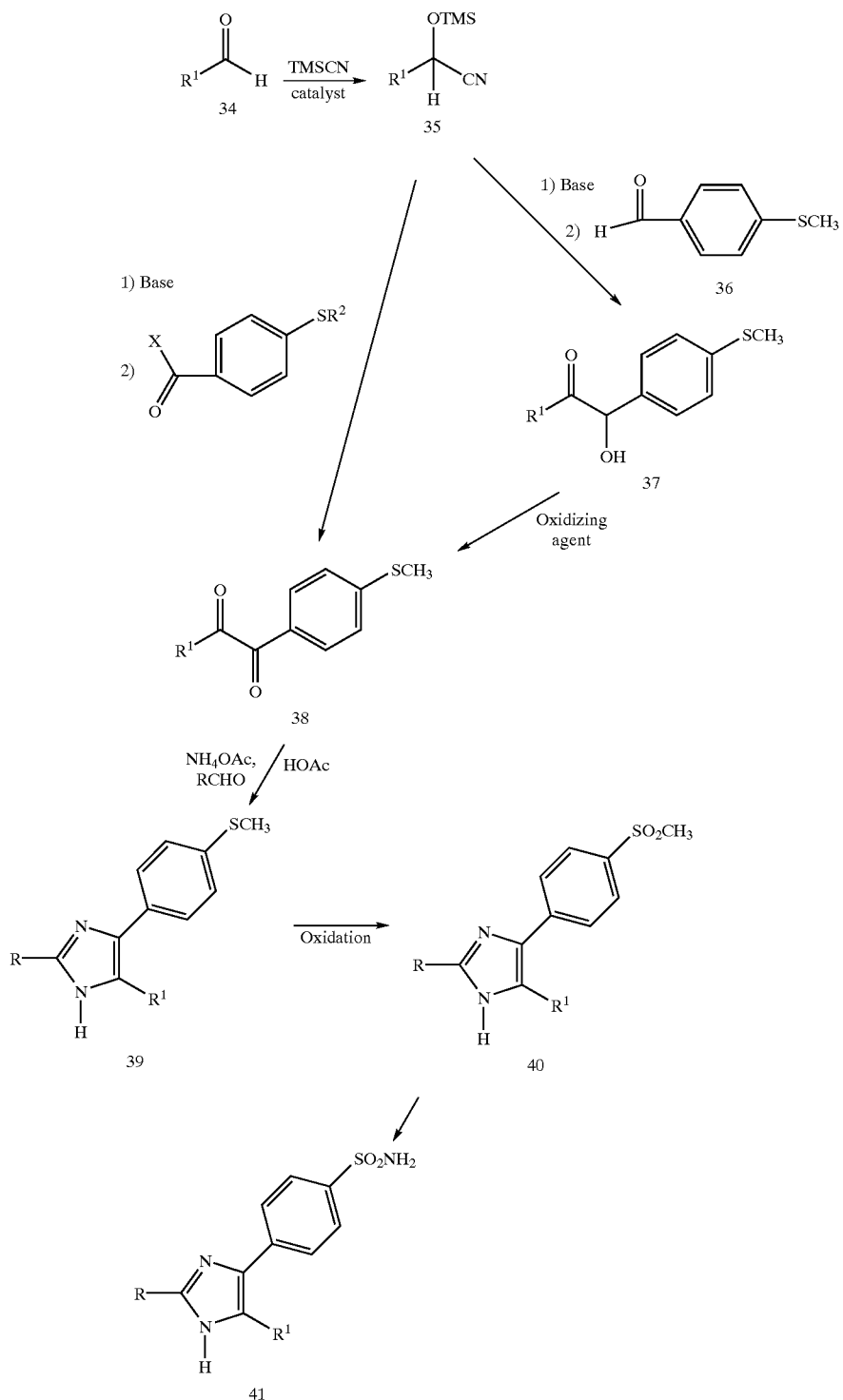

Imidazole cyclooxygenase-2 inhibitor compounds 41 may be synthesized according to the sequence outlined in Scheme VII. Aldehyde 34 may be converted to the protected cyanohydrin 35 by reaction with a trialkylsilyl cyanide, such as trimethylsilyl cyanide (TMSCN) in the presence of a catalyst such as zinc iodide ($ZnI_2$) or potassium cyanide (KCN). Reaction of cyanohydrin 35 with a strong base followed by treatment with benzaldehyde 36 and using both acid and base treatments, in that order, on workup gives benzoin 37. Examples of strong bases suitable for this reaction are lithium diisopropylamide (LDA) and lithium hexamethyldisilazane. Benzoin 37 may be converted to benzil 38 by reaction with a suitable oxidizing agent, such as bismuth oxide or manganese dioxide, or by a Swern oxidation using dimethyl sulfoxide (DMSO) and trifluoroacetic anhydride. Benzil 38 may be obtained directly by reaction of the anion of cyanohydrin 35 with a substituted benzoic acid halide. Any of compounds 37 and 38 may be used as intermediates for conversion to imidazoles 39 according to chemical procedures known by those skilled in the art and described by M. R. Grimmett, "Advances in Imidazole Chemistry" in Advances in Heterocyclic Chemistry, 12, 104 (1970). The conversion of 38 to imidazoles 39 is carried out by reaction with ammonium acetate and an appropriate aldehyde (RCHO) in acetic acid. Benzoin 37 may be converted to imidazoles 39 by reaction with formamide. In addition, benzoin 37 may be converted to imidazoles by first acylating with an appropriate acyl group (RCO—) and then treating with ammonium hydroxide. Those skilled in the art will recognize that the oxidation of the sulfide to the sulfone may be carried out at any point along the way beginning with compounds 36, and including oxidation of imidazoles 39, using, for examples, reagents such as hydrogen peroxide in acetic acid, m-chloroperoxybenzoic acid (MCPBA) and potassium peroxymonosulfate (OXONE®). Sulfonamides 41 can be prepared such as by the Huang method [*Tet. Lett.*, 35, 7201–04 (1994)].

Diaryl/heteroaryl imidazoles can be prepared by the methods described in U.S. Pat. Nos. 3,707,475, 4,686,231, 4,503,065, 4,472,422, 4,372,964, 4,576,958, 3,901,908, PCT application Ser. No. US95/09505, European publication EP 372,445, and PCT document WO 95/00501, which are incorporated by reference.

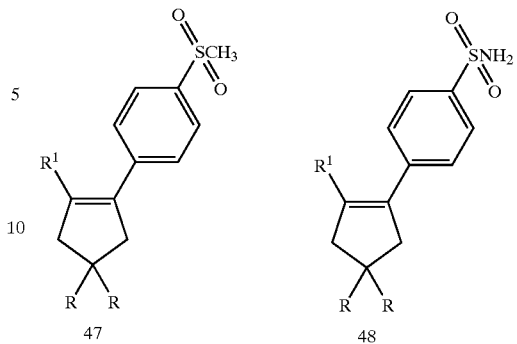

Diaryl/heteroaryl cyclopentene cyclooxygenase-2 inhibitors can be prepared by the methods described in U.S. Pat. No. 5,344,991, and PCT document WO 95/00501, which are incorporated by reference.

Scheme IX

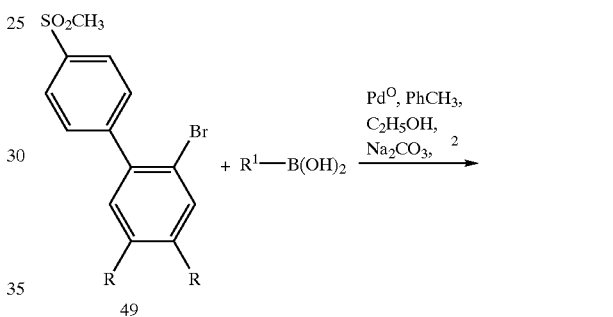

Scheme VIII

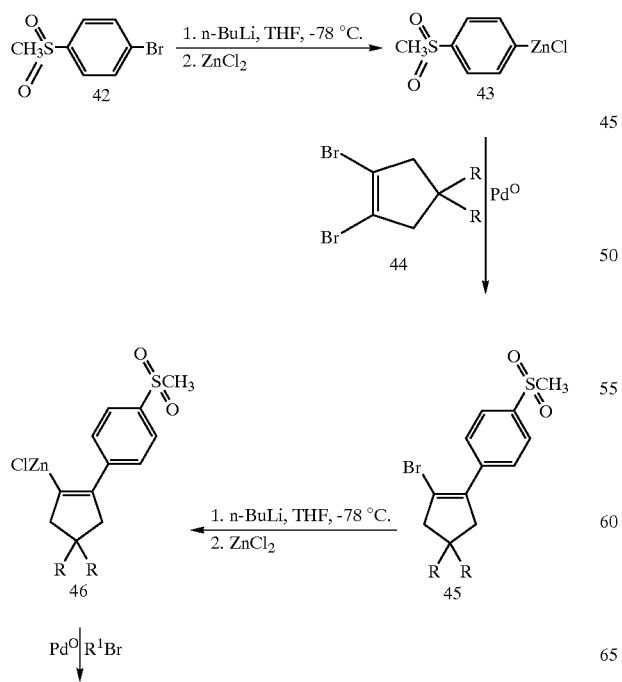

Similarly, Synthetic Scheme IX shows the procedure for the preparation of 1,2-diarylbenzene cyclooxygenase-2 inhibitor agents 51 from 2-bromo-biphenyl intermediates 49 (prepared similar to that described in Synthetic Scheme VIII) and the appropriate substituted phenylboronic acids. Using a coupling procedure similar to the one developed by Suzuki et al. [*Synth. Commun.*, 11, 513 (1981)], intermediates 49 are reacted with the boronic acids in toluene/ethanol at reflux in the presence of a Pd° catalyst, e.g., tetrakis (triphenylphosphine)palladium(0), and 2M sodium carbonate to give the corresponding 1,2-diarylbenzene antiinflammatory agents 50 of this invention. Sulfonamides 51 can be prepared such as by the Huang method [*Tet. Lett.*, 35, 7201–04 (1994)]. Such terphenyl compounds can be prepared by the methods described in U.S. application Ser. No. 08/346,433, which is incorporated by reference.

Scheme X

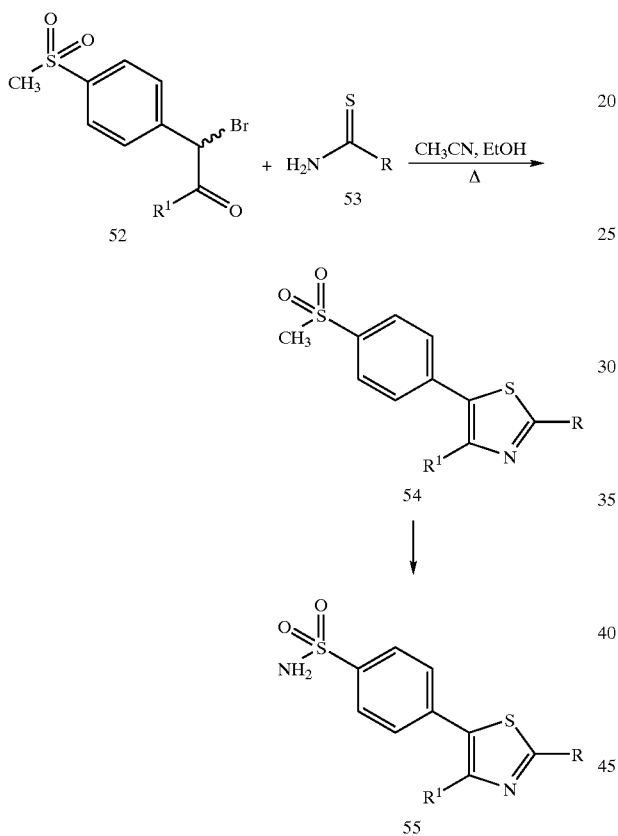

Diaryl/heteroaryl thiazole cyclooxygenase-2 inhibitors can be prepared by the methods described in U.S. Pat. Nos. 4,051,250, 4,632,930, European document EP 592,664, and PCT documents WO96/03392, and WO 95/00501, which are incorporated by reference. Isothiazoles can be prepared as described in PCT document WO 95/00501.

Diaryl/heteroaryl pyridine cyclooxygenase-2 inhibitors can be prepared by the methods described in U.S. Pat. Nos. 5,169,857, 4,011,328, 4,533,666, PCT application Ser. No. US96/01110 and PCT application Ser. No. US96/01111, which are incorporated by reference.

Scheme XI

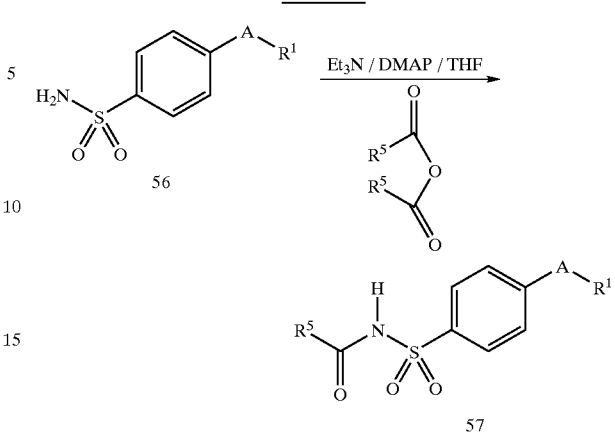

Synthetic Scheme XI illustrates a method for the preparation of acylated sulfonamides 57. The method involves treatment of an unsubstituted sulfonamide 56 with a suitable acylating agent such as an anhydride, acid chloride, acyl imidazole, or active ester, in the presence of base and a suitable solvent, such as tetrahydrofuran (THF), to afford the acylated sulfonamide 57. The product 57 can then be isolated by chromatography or by crystallization.

Scheme XII

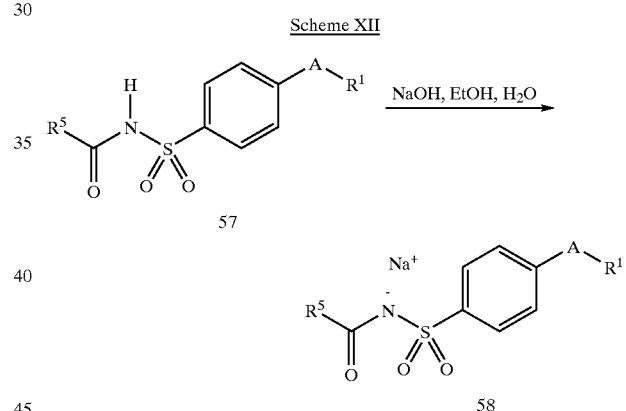

Synthetic Scheme XII shows the method for the preparation of the corresponding salt form of 57. Treatment of 57 with a suitable strong base such as sodium hydroxide, potassium hydroxide, calcium hydroxide and the like produces the corresponding salt form 58. A wide variety of solvents can be used so long as they do not react with the added strong base, such solvents as ethanol and tetrahydrofuran are preferred.

Scheme XIII

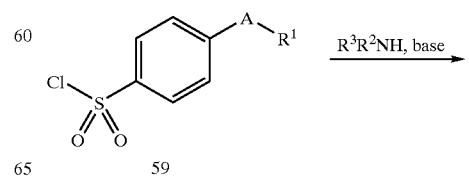

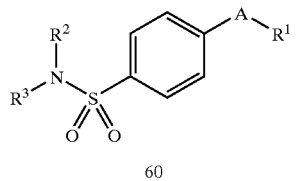

Synthetic Scheme XIII shows the method used for the preparation of substituted sulfonamides 60. The step involves treatment of a suitable sulfonyl chloride 59 with an amine to produce the substituted sulfonamide 59. The amine may be either a primary amine ($R^3NH_2$) or a secondary amine ($R^3R^2NH$). The reaction is generally conducted in the presence of added base. The reaction may also be conducted in the presence of excess amine. Under the conditions of excess amine, the amine functions as both nucleophile and base.

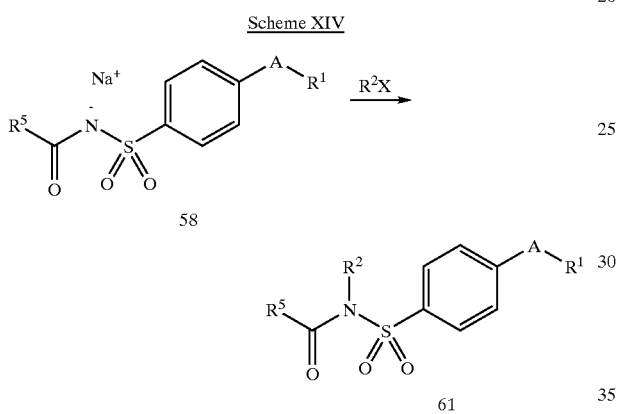

Synthetic Scheme XIV shows the method used for the synthesis of N-substituted acyl sulfonamides 61. The procedure involves treatment of the salt of an acylated sulfonamide 58 with an alkyl halide ($R^2$—X) to produce the corresponding N-alkylated acyl sulfonamide 61. This process may be conducted in a wide variety of solvents with a wide array of electrophiles.

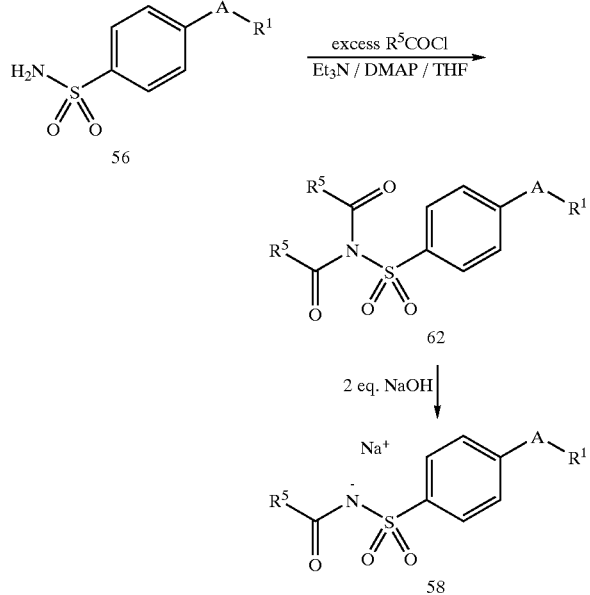

Synthetic Scheme XV illustrates the method used for the synthesis of certain N-acylated sulfonamides 57. The procedure involves treatment of the sulfonamide 56 with an excess of an anhydride, acid chloride or carbamyl chloride in the presence of a tertiary amine base to provide the corresponding bis(N-acylated)sulfonamide 62. The bis(N-acylated)sulfonamide 62 is then treated with two equivalents of a strong base such as sodium hydroxide to provide the sodium salt 58.

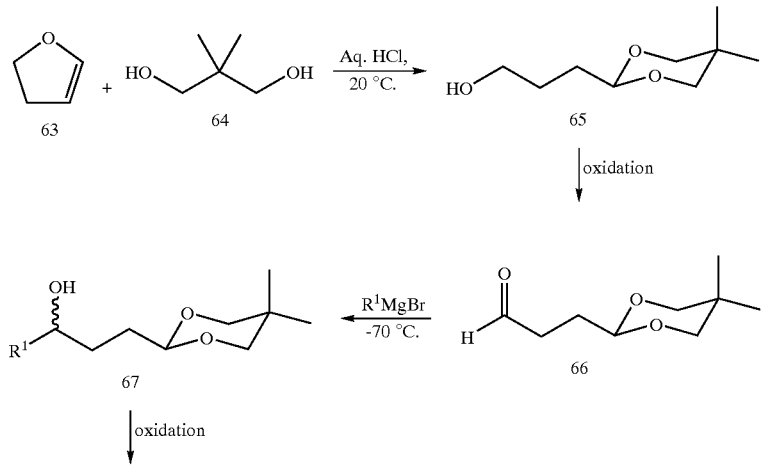

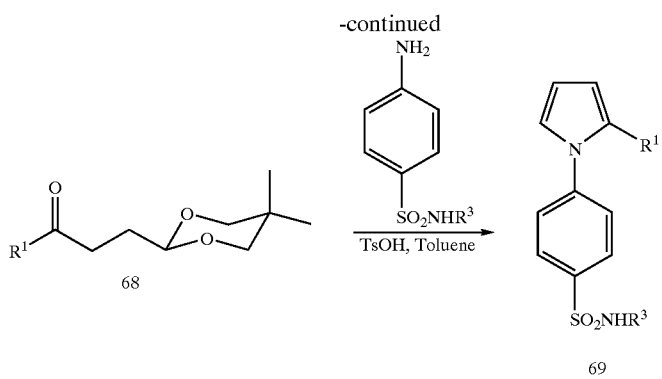

Synthetic Scheme XVI illustrates the method used for the synthesis of certain N-alkylated pyrrole sulfonamides. Alcohol 65 is synthesized by following the literature procedure (J. Org. Chem. 57, 2195,1992). The alcohol 65 is oxidized such as by treatment with oxalyl chloride in an appropriate solvent, such as methylene chloride or DMSO. Addition, such as by Grignard reagents, produces the alcohol 67. Oxidation with pyridinium chlorochromate produces the ketones 68. Condensation with a [(N-substituted amino)sulfonyl]benzeneamine in the presence of p-toluenesulfonic acid (produces the substituted pyrrole sulfonamide 69.

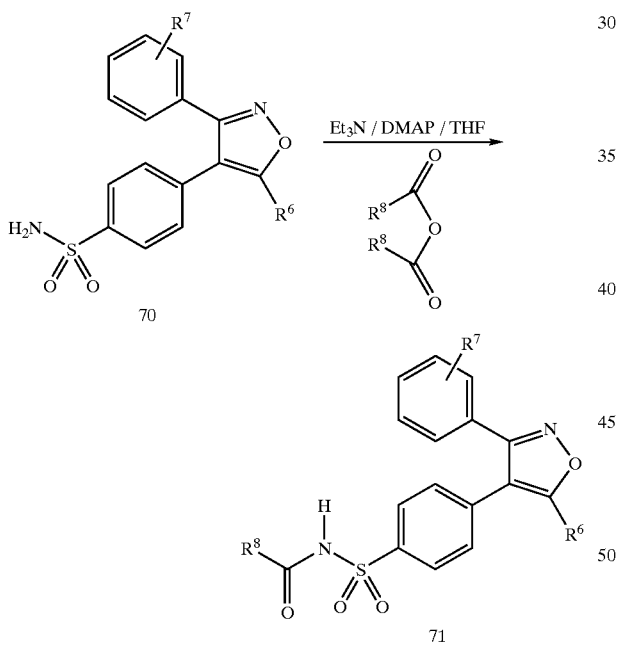

Synthetic Scheme XVII illustrates the method for the preparation of acylated isoxazole sulfonamides 71. The step involves treatment of an unsubstituted sulfonamide 70 with a suitable acylating agent such as an anhydride, acid chloride, acyl imidazole, or active ester to afford the acylated sulfonamide 71. The product 71 can be isolated by chromatography or by crystallization.

The following examples contain detailed descriptions of the methods of preparation of compounds of Formulas I–III. These detailed descriptions fall within the scope, and serve to exemplify, the above described General Synthetic Procedures which form part of the invention. These detailed descriptions are presented for illustrative purposes only and are not intended as a restriction on the scope of the invention. All parts are by weight and temperatures are in Degrees centigrade unless otherwise indicated. All compounds showed NMR spectra consistent with their assigned structures.

The following abbreviations are used:
HCl—hydrochloric acid
DMSO—dimethylsulfoxide
DMSOd6—deuterated dimethylsulfoxide
CDCl$_3$—deuterated chloroform
MgSO$_4$—magnesium sulfate
NaHCO$_3$—sodium bicarbonate
KHSO$_4$—potassium hydrogen sulfate
DMF—dimethylformamide
NaOH—sodium hydroxide
BOC—tert-butyloxycarbonyl
CD$_3$OD—deuterated methanol
EtOH—ethanol
LiOH—lithium hydroxide
CH$_2$Cl$_2$—methylene chloride
h—hour
hr—hour
min—minutes
THF—tetrahydrofuran
TLC—thin layer chromatography
Et$_3$N—triethylamine
DBU—1,8-diazabicyclo[5.4.0]undec-7-ene
DMAP—4-dimethylaminopyridine

EXAMPLE 1

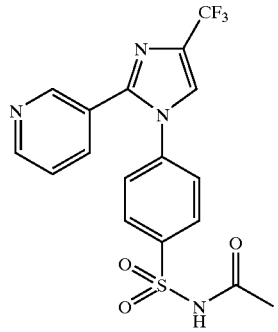

N-[[4-[2-(3-Pyridinyl)-4-(trifluoromethyl)-1H-imidazol-1-yl]phenyl]sulfonyl]acetamide A mixture of 4-[2-(pyridin-3-yl)-4-(trifluoromethyl)-1H-imidazol-1-yl]benzenesulfonamide (0.5 g, 1.36 mmol), acetic anhydride (0.42 g, 4.1 mmol), 4-dimethylaminopyridine (DMAP) (0.083 g, 0.68 mmol) and triethylamine (0.17 g, 1.6 mmol) was stirred at room temperature for 16 hours. The reaction mixture was diluted with 50 mL of water and extracted with ethyl acetate. The organic layer was washed with water, brine, dried over magnesium sulfate and filtered. The filtrate was concentrated under vacuum and the residue was recrystallized from ethyl acetate and hexane to afford 0.5 g (90%) of N-[[4-[2-(3-pyridinyl)-4-(trifluoromethyl)-1H-imidazol-1-yl]phenyl]sulfonyl]acetamide as a colorless solid: mp (DSC): 244–246 _C. Anal. Calc'd. for $C_{17}H_{13}F_3N_4O_3S$: C, 49.76; H, 3.19; N, 13.65; S, 7.81. Found: C, 49.66; H, 3.06; N, 13.53; S, 8.11.

EXAMPLE 2

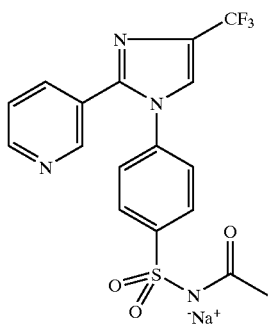

N-[[4-[2-(3-Pyridinyl)-4-(trifluoromethyl)-1H-imidazol-1-yl]phenyl]sulfonyl]acetamide, sodium salt To a suspension of N-[[4-[2-(3-pyridinyl)-4-(trifluoromethyl)-1H-imidazol-1-yl]phenyl]sulfonyl]acetamide (Example 1) (0.41 g, 1.0 mmol) in 10 mL of absolute ethanol was added a solution of sodium hydroxide (0.04 g, 1.0 mmol) in 0.4 mL of ethanol. The mixture was stirred at room temperature for 10 min. Solvent was evaporated in vacuo and the residue was dried at high vacuum to give 0.33 g (76%) of N-[[4-[2-(3-pyridinyl)-4-(trifluoromethyl)-1H-imidazol-1-yl]phenyl]sulfonyl]acetamide, sodium salt as a white powder: mp (DSC): 291 _C (dec). Anal. Calc'd. for $C_{17}H_{12}F_3N_4O_3SNa.0.5\ H_2O$: C, 46.26; H, 2.97; N, 12.69; S, 7.26. Found: C, 45.88; H, 3.02; N, 11.69; S, 7.13.

EXAMPLE 3

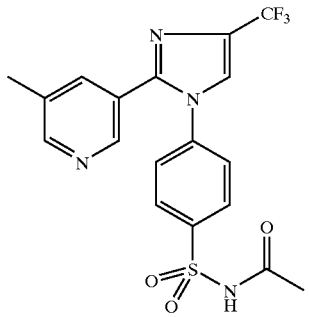

N-[[4-[2-(5-Methylpyridin-3-yl)-4-(trifluoromethyl)-1H-imidazol-1-yl]phenyl]sulfonyl]acetamide A mixture of 4-[2-(5-methylpyridin-3-yl)-4-(trifluoromethyl)-1H-imidazol-1-yl]benzenesulfonamide (0.5 g, 1.3 mmol), acetic anhydride (0.40 g, 3.9 mmol), DMAP (0.09 g, 0.7 mmol) and triethylamine (0.16 g, 1.6 mmol) was stirred at room temperature for 16 hours. The reaction mixture was diluted with 50 mL of water and extracted with ethyl acetate. The organic layer was washed with water, brine, dried over magnesium sulfate and filtered. The filtrate was concentrated under vacuum and the residue was recrystallized from ethyl acetate and hexane to afford 0.4 g (72%) of N-[[4-[2-(5-methylpyridin-3-yl)-4-(trifluoromethyl)-1H-imidazol-1-yl]phenyl]sulfonyl] acetamide as a colorless solid: mp (DSC) 268–270 _C. Anal. Calc'd. for $C_{18}H_{15}F_3N_4O_3S$: C, 50.94; H, 3.56; N, 13.20; S, 7.56. Found: C, 50.68; H, 3.47; N, 12.53; S, 7.43.

EXAMPLE 4

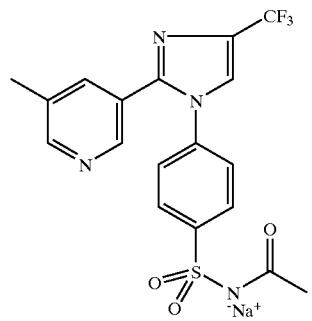

N-[[4-[2-(5-Methylpyridin-3-yl)-4-(trifluoromethyl)-1H-imidazol-1-yl]phenyl]sulfonyl]acetamide, sodium salt To a suspension of N-[[4-[2-(5-methylpyridin-3-yl)-4-(trifluoromethyl)-1H-imidazol-1-yl]phenyl]sulfonyl] acetamide (Example 3) (0.25 g, 0.6 mmol) in 5 mL of absolute ethanol was added a solution of sodium hydroxide (0.024 g, 0.6 mmol) in 0.4 mL of ethanol. The mixture was stirred at room temperature for 10 min. Solvent was evaporated in vacuo and the residue was dried at high vacuum to give 0.25 g (95%) of N-[[4-[2-(5-methylpyridin-3-yl)-4-(trifluoromethyl)-1H-imidazol-1-yl]phenyl]sulfonyl] acetamide, sodium salt as a white powder: mp(DSC) 278–281 _C. Anal. Calc'd. for $C_{18}H_{14}F_3N_4O_3SNa.1.0\ H_2O$: C, 46.55; H, 3.47; N, 12.06; S, 6.90. Found: C, 46.35; H, 3.19; N, 11.79; S, 6.52.

EXAMPLE 5

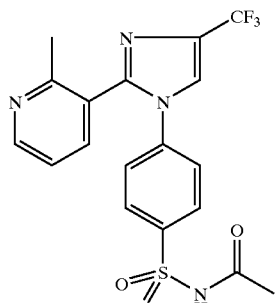

N-[[4-[2-(2-Methylpyridin-3-yl)-4-(trifluoromethyl)-1H-imidazol-1-yl]phenyl]sulfonyl]acetamide A mixture of 4-[2-(2-methylpyridin-3-yl)-4-(trifluoromethyl)-1H-imidazol-1-yl]benzenesulfonamide (0.5 g, 1.3 mmol), acetic anhydride (0.40 g, 3.9 mmol), DMAP (0.09 g, 0.7 mmol) and triethylamine (0.16 g, 1.6 mmol) was stirred at room temperature for 16 hours. The reaction mixture was diluted with 50 mL of water and extracted with ethyl acetate. The organic layer was washed with water, brine, dried over magnesium sulfate and filtered. The filtrate was concentrated under vacuum and the residue was recrystallized from ethyl acetate and hexane to afford 0.55 g (99%) of N-[[4-[2-(2-methylpyridin-3-yl)-4-(trifluoromethyl)-1H-imidazol-1-yl]phenyl]sulfonyl] acetamide as a colorless solid: mp (DSC) 243–245 _C. Anal. Calc'd. for $C_{18}H_{15}F_3N_4O_3S$: C, 50.94; H, 3.56; N, 13.20; S, 7.56. Found: C, 50.64; H, 3.43; N, 12.64; S, 7.37.

EXAMPLE 6

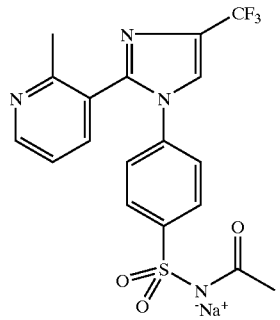

N-[[4-[2-(2-Methylpyridin-3-yl)-4-(trifluoromethyl)-1H-imidazol-1-yl]phenyl]sulfonyl]acetamide, sodium salt To a suspension of N-[[4-[2-(2-methylpyridin-3-yl)-4-(trifluoromethyl)-1H-imidazol-1-yl]phenyl]sulfonyl] acetamide (Example 5) (0.35 g, 0.83 mmol) in 7.5 mL of absolute ethanol was added a solution of sodium hydroxide (0.033 g, 0.83 mmol) in 0.83 mL of ethanol. The mixture was stirred at room temperature for 10 min. Solvent was evaporated in vacuo and the residue was dried at high vacuum to give 0.37 g (99%) of N-[[4-[2-(2-methylpyridin-3-yl)-4-(trifluoromethyl)-1H-imidazol-1-yl]phenyl] sulfonyl]acetamide, sodium salt as a white powder: mp(DSC) 313 _C (dec). Anal. Calc'd. for $C_{18}H_{14}F_3N_4O_3SNa.0.75\ H_2O$: C, 47.01; H, 3.40; N, 12.18; S, 6.97. Found: C, 47.51; H, 3.71; N, 11.70; S, 6.51.

EXAMPLE 7

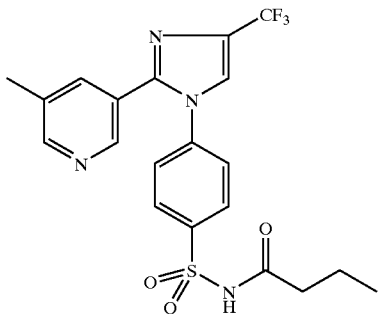

N-[[4-[2-(5-Methylpyridin-3-yl)-4-(trifluoromethyl)-1H-imidazol-1-yl]phenyl]sulfonyl]butanamide A mixture of 4-[2-(5-methylpyridin-3-yl)-4-(trifluoromethyl)-1H-imidazol-1-yl]benzenesulfonamide (0.5 g, 1.3 mmol), butyric anhydride (0.62 g, 3.9 mmol), DMAP (0.09 g, 0.7 mmol) and triethylamine (0.16 g, 1.6 mmol) was stirred at room temperature for 16 hours. The reaction mixture was diluted with 50 mL of water and extracted with ethyl acetate. The organic layer was washed with water, brine, dried over magnesium sulfate and filtered. The filtrate was concentrated under vacuum and the residue was recrystallized from ethyl acetate and hexane to afford 0.50 g (85%) of N-[[4-[2-(5-methylpyridin-3-yl)-4-(trifluoromethyl)-1H-imidazol-1-yl]phenyl]sulfonyl] butanamide as a colorless solid: mp (DSC) 203–204 _C. Anal. Calc'd. for $C_{20}H_{19}F_3N_4O_3S$: C, 53.09; H, 4.23; N, 12.38; S, 7.09. Found: C, 52.73; H, 4.21; N, 11.79; S, 7.00.

EXAMPLE 8

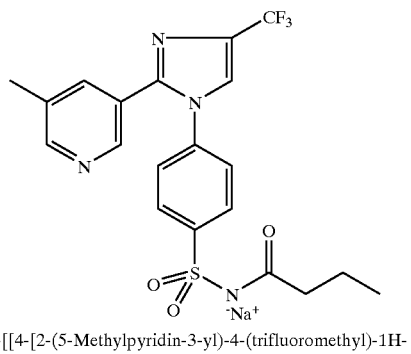

N-[[4-[2-(5-Methylpyridin-3-yl)-4-(trifluoromethyl)-1H-imidazol-1-yl]phenyl]sulfonyl]butanamide, sodium salt To a suspension of N-[[4-[2-(5-methylpyridin-3-yl)-4-(trifluoromethyl)-1H-imidazol-1-yl]phenyl]sulfonyl] butanamide (Example 7) (0.31 g, 0.68 mmol) in 5 mL of absolute ethanol was added a solution of sodium hydroxide (0.028 g, 0.68 mmol) in 0.68 mL of ethanol. The mixture was stirred at room temperature for 10 min. Solvent was evaporated in vacuo and the residue was dried at high vacuum to give 0.28 g (87%) of N-[[4-[2-(5-methylpyridin-3-yl)-4-(trifluoromethyl)-1H-imidazol-1-yl]phenyl] sulfonyl]butanamide, sodium salt as a white powder: mp(DSC) 303 _C (dec). Anal. Calc'd. for $C_{20}H_{18}F_3N_4O_3SNa.1.0\ H_2O$: C, 48.78; H, 4.09; N, 11.38; S, 6.51. Found: C, 47.90; H, 3.67; N, 11.38; S, 6.06.

EXAMPLE 9

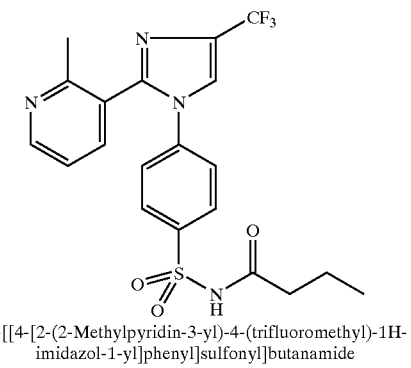

N-[[4-[2-(2-Methylpyridin-3-yl)-4-(trifluoromethyl)-1H-imidazol-1-yl]phenyl]sulfonyl]butanamide A mixture of 4-[2-(2-methylpyridin-3-yl)-4-(trifluoromethyl)-1H-imidazol-1-yl]benzenesulfonamide (0.5 g, 1.3 mmol), butyric anhydride (0.62 g, 3.9 mmol), DMAP (0.09 g, 0.7 mmol) and triethylamine (0.16 g, 1.6 mmol) was stirred at room temperature for 16 hours. The reaction mixture was diluted with 50 mL of water and extracted with ethyl acetate. The organic layer was washed with water, brine, dried over magnesium sulfate and filtered. The filtrate was concentrated under vacuum and the residue was recrystallized from ethyl acetate and hexane to afford 0.49 g (84%) of N-[[4-[2-(2-methylpyridin-3-yl)-4-(trifluoromethyl)-1H-imidazol-1-yl]phenyl]sulfonyl]butanamide as a colorless solid: mp (DSC) 250–252 _C. Anal. Calc'd. for $C_{20}H_{19}F_3N_4O_3S$: C, 53.09; H, 4.23; N, 12.38; S, 7.09. Found: C, 52.97; H, 4.21; N, 11.07; S, 7.11.

EXAMPLE 10

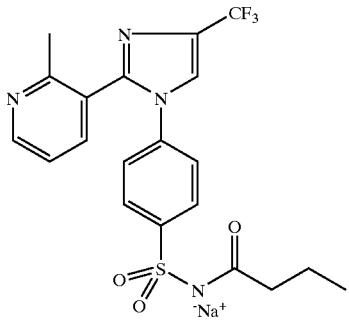

N-[[4-[2-(2-Methylpyridin-3-yl)-4-(trifluoromethyl)-1H-imidazol-1-yl]phenyl]sulfonyl]butanamide, sodium salt To a suspension of N-[[4-[2-(2-methylpyridin-3-yl)-4-(trifluoromethyl)-1H-imidazol-1-yl]phenyl]sulfonyl]butanamide (Example 9) (0.3 g, 0.66 mmol) in 5 mL of absolute ethanol was added a solution of sodium hydroxide (0.027 g, 0.66 mmol) in 0.66 mL of ethanol. The mixture was stirred at room temperature for 10 min. Solvent was evaporated in vacuo and the residue was dried at high vacuum to give 0.26 g (83%) of N-[[4-[2-(2-methylpyridin-3-yl)-4-(trifluoromethyl)-1H-imidazol-1-yl]phenyl]sulfonyl]butanamide, sodium salt as a white powder: mp(DSC) 320 _C (dec). Anal. Calc'd. for $C_{20}H_{18}F_3N_4O_3SNa$: C, 50.63; H, 3.82; N, 11.81; S, 6.76. Found: C, 49.85; H, 3.78; N, 11.51; S, 6.32.

EXAMPLE 11

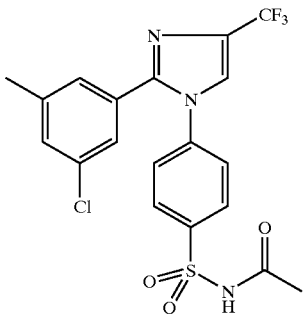

N-[[4-[2-(3-Chloro-5-methylphenyl)-4-(trifluoromethyl)-1H-imidazol-1-yl]phenyl]sulfonyl]acetamide To a suspension of 4-[2-(3-chloro-5-methylphenyl)-4-(trifluoromethyl)-1H-imidazol-1-yl]benzenesulfonamide (0.30 g, 0.72 mmol) in 1.5 mL of acetic acid was added 1.5 mL of acetyl chloride at room temperature. The mixture was heated at reflux for 5 hours. After cooling, the reaction mixture was concentrated under vacuum and the residue was treated with ether to give 0.23 g (70%) of N-[[4-[2-(3-chloro-5-methylphenyl)-4-(trifluoromethyl)-1H-imidazol-1-yl]phenyl]sulfonyl]acetamide as a white solid: mp (DSC) 232–235 _C. Anal. Calc'd. for $C_{19}H_{15}ClF_3N_3O_3S$: C, 49.84; H, 3.30; N, 9.18; S, 7.00. Found: C, 49.72; H, 3.48; N, 8.81; S, 7.18.

EXAMPLE 12

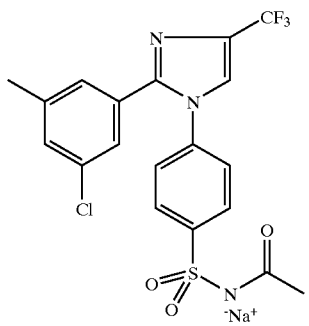

N-[[4-[2-(3-Chloro-5-methylphenyl)-4-(trifluoromethyl)-1H-imidazol-1-yl]phenyl]sulfonyl]acetamide, sodium salt To a suspension of N-[[4-[2-(3-chloro-5-methylphenyl)-4-(trifluoromethyl)-1H-imidazol-1-yl]phenyl]sulfonyl]acetamide (Example 11) (0.1 g, 0.22 mol) in 3 mL of absolute ethanol was added a solution of sodium hydroxide (0.0088 g, 0.22 mmol) in 2 mL of ethanol. The mixture was stirred at room temperature for 10 min. Solvent was evaporated in vacuo and the residue was dried at high vacuum to give 0.09 g (85%) of N-[[4-[2-(3-chloro-5-methylphenyl)-4-(trifluoromethyl)-1H-imidazol-1-yl]phenyl]sulfonyl]acetamide, sodium salt as a white powder: mp(DSC) 320 _C (dec). Anal. Calc'd. for $C_{19}H_{14}ClF_3N_3O_3SNa$: C, 47.56; H, 2.94; N, 8.76; S, 6.68. Found: C, 46.89; H, 3.02; N, 8.27; S, 6.03.

EXAMPLE 13

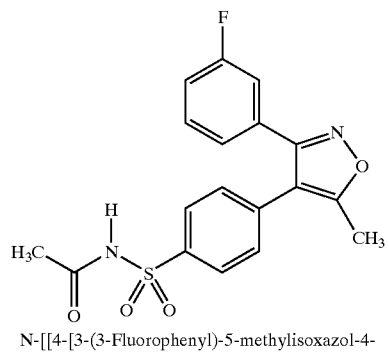

N-[[4-[3-(3-Fluorophenyl)-5-methylisoxazol-4-yl]phenyl]sulfonyl]acetamide

Acetic anhydride (1.01 g, 9.39 mmol) and triethylamine (0.401 g, 3.97 mmol) were added to a solution of 4-[5-methyl-3-(3-fluorophenyl)isoxazol-4-yl]benzenesulfonamide (1.10 g, 3.31 mmol) and N,N-dimethylpyridine (0.202 g) in dry tetrahydrofuran. After stirring for 18 hours at room temperature, the reaction mixture was concentrated. The residue was dissolved in ethyl acetate, washed successively with 1N hydrochloric acid and brine, dried over anhydrous $MgSO_4$ and concentrated to afford 1.0 g (81%) of the desired product as a crystalline product: mp 144–145° C. $^1H$ NMR $(CDCl_3)$ 8.00 (d, 2H, J=7.3 Hz), 7.30–7.27 (m, 4H), 7.10–7.06 (m, 3H), 2.46 (s, 3H), 1.99 (s, 3H). Anal. Calc'd for $C_{18}H_{15}FN_2O_4S$: C, 57.75; H, 4.04; N, 7.48. Found: C, 57.84; H, 4.06; N, 7.49.

EXAMPLE 14

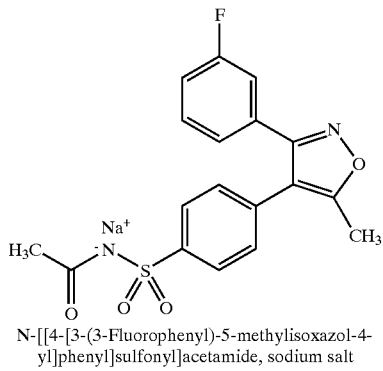

N-[[4-[3-(3-Fluorophenyl)-5-methylisoxazol-4-yl]phenyl]sulfonyl]acetamide, sodium salt A mixture of N-[[4-[3-(3-fluorophenyl)-5-methylisoxazol-4-yl]phenyl]sulfonyl]acetamide (Example 13) (0.312 g, 0.83 mmol) and sodium hydroxide (0.33 mL, 2.5 N) in ethanol was concentrated to dryness. The residue was diluted with ethanol and was concentrated again. The residue was dried in vacuo to afford 0.32 g (97%) of the crystalline product: mp 112–131° C. $^1$H NMR (D$_2$O/300 MHz) 7.64 (d, 2H, J=8.3 Hz), 7.21–6.91 (m, 6H), 2.27 (s, 3H), 1.78 (s, 3H). Anal. Calc'd for C$_{18}$H$_{14}$FN$_2$O$_4$SNa.0.5H$_2$O: C, 53.28; H, 3.73; N, 6.80. Found: C, 53.57; H, 3.73; N, 6.80.

The following compounds (Examples 15–67) were obtained according to procedures similar to that exemplified in Examples 13–14, with the substitution of the appropriate sulfonamide and anhydride.

EXAMPLE 15

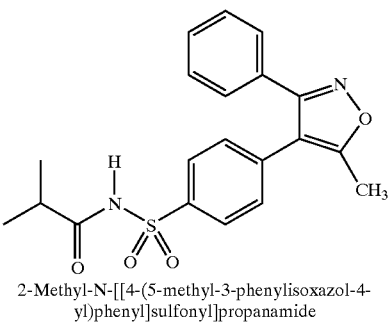

2-Methyl-N-[[4-(5-methyl-3-phenylisoxazol-4-yl)phenyl]sulfonyl]propanamide mp 115.0–115.6° C. $^1$H NMR (CDCl$_3$/300 MHz) 8.43 (brs, 1H), 8.04 (d, 2H, J=8.4 Hz), 7.40–7.31 (m, 7H), 2.50 (s, 3H), 2.45 (sept, 1H, J=6.9 Hz), 1.12 (d, 6H, J=6.9 Hz). FABLRMS m/z 385 (M$^+$H). FABHRMS m/z 385.1222 (M$^+$H, C$_{20}$H$_{21}$N$_2$O$_4$S Calc'd 385.1245). Anal. Calc'd for C$_{20}$H$_{20}$N$_2$O$_4$S: C, 62.48; H, 5.24; N, 7.29. Found: C, 62.55; H, 5.24; N, 7.21.

EXAMPLE 16

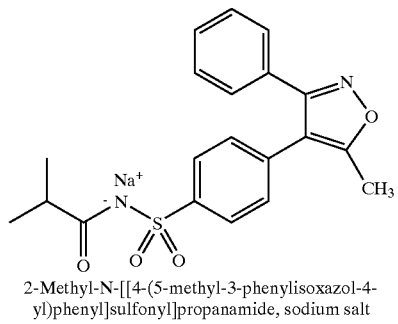

2-Methyl-N-[[4-(5-methyl-3-phenylisoxazol-4-yl)phenyl]sulfonyl]propanamide, sodium salt mp>300° C. $^1$H NMR (DMSO-d$_6$/300 MHz) 7.71 (d, 2H, J=8.1 Hz), 7.43–7.24 (m, 5H), 7.19 (d, 2H, J=8.1 Hz), 2.44 (s, 3H), 2.15 (sept, 1H, J=6.9 Hz), 0.89 (d, 6H, J=6.9 Hz). FABLRMS m/z 407 (M$^+$H). FABHRMS m/z 407.1053 (M$^+$H, C$_{20}$H$_{21}$N$_2$O$_4$SNa Calc'd 407.1041). Anal. Calc'd for C$_{20}$H$_{19}$N$_2$O$_4$SNa: C, 59.10; H, 4.71; N, 6.89. Found: C, 58.98; H, 4.68; N, 6.94.

EXAMPLE 17

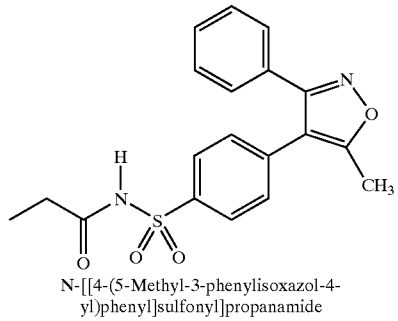

N-[[4-(5-Methyl-3-phenylisoxazol-4-yl)phenyl]sulfonyl]propanamide mp 148.9–151.0° C. $^1$H NMR (CDCl$_3$/300 MHz) 8.60 (brs, 1H), 8.04 (d, 2H, J=8.7 Hz), 7.38–7.31 (m, 7H), 2.50 (s, 3H), 2.32 (q, 2H, J=7.2 Hz), 1.10 (t, 3H, J=7.2 Hz). FABLRMS m/z 371 (M$^+$H). FABHRMS m/z 371.1049 (M$^+$H), Calc'd 371.1066. Anal. Calc'd for C$_{19}$H$_{18}$N$_2$O$_4$S: C, 61.61; H, 4.90; N, 7.56. Found: C, 61.52; H, 4.92; N, 7.53.

EXAMPLE 18

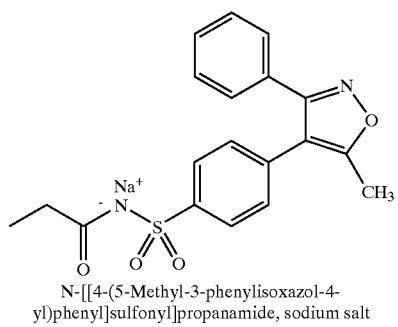

N-[[4-(5-Methyl-3-phenylisoxazol-4-yl)phenyl]sulfonyl]propanamide, sodium salt mp 271.5–272.7° C. $^1$H NMR (D$_2$O/300 MHz) 7.57 (d, 2H, J=8.4 Hz), 7.30–6.90 (m, 7H), 2.12 (s, 3H), 2.00 (q, 2H, J=7.8 Hz), 0.83 (t, 3H, J=7.8 Hz). FABLRMS m/z 393 (M$^+$H). Anal. Calc'd for C$_{19}$H$_{17}$N$_2$O$_4$SNa: C, 58.61; H, 4.37; N, 7.14. Found: C, 57.92; H, 4.53; N, 6.95.

EXAMPLE 19

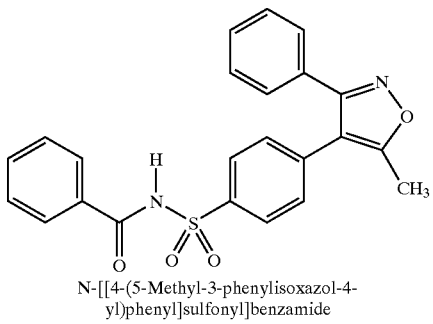

N-[[4-(5-Methyl-3-phenylisoxazol-4-yl)phenyl]sulfonyl]benzamide mp 208.8–210.2° C. $^1$H NMR (CDCl$_3$/300 MHz) 9.05 (brs, 1H), 8.14 (d, 2H, J=8.5 Hz), 7.82 (d, 2H, J=7.5 Hz), 7.59 (dd, 1H, J=7.3, 7.5 Hz), 7.49–7.30 (m, 9H), 2.50 (s, 3H). FABLRMS m/z 419 (M$^+$H). FABHRMS m/z 419.1083 (M$^+$H, Calc'd 419.1066). Anal. Calc'd for C$_{23}$H$_{18}$N$_2$O$_4$S: C, 66.02; H, 4.34; N, 6.69. Found: C, 65.95; H, 4.40; N, 6.69.

EXAMPLE 20

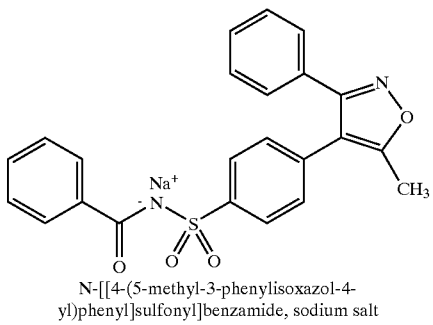

N-[[4-(5-methyl-3-phenylisoxazol-4-yl)phenyl]sulfonyl]benzamide, sodium salt mp 288.2–291.2° C. $^1$H NMR (DMSO-d$_6$/300 MHz) 7.90 (d, 2H, J=8.1 Hz), 7.83 (d, 2H, J=8.4 Hz), 7.44–7.23 (m, 8H), 7.22 (d, 2H, J=8.4 Hz), 2.44 (s, 3H). FABLRMS m/z 441 (M$^+$H). FABHRMS m/z 441.0898 (M$^+$H, Calc'd 441.0885). Anal. Calc'd for C$_{23}$H$_{17}$N$_2$O$_4$SNa: C, 62.72; H, 3.89; N, 6.36. Found: C, 62.53; H, 4.06; N, 6.17.

EXAMPLE 21

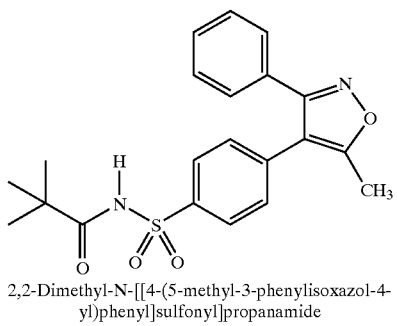

2,2-Dimethyl-N-[[4-(5-methyl-3-phenylisoxazol-4-yl)phenyl]sulfonyl]propanamide mp 190.5–191.1° C. $^1$H NMR (CDCl$_3$/300 MHz) 8.20 (brs, 1H), 8.04 (d, 2H, J=8.5 Hz), 7.39–7.30 (m, 7H), 2.51 (s, 3H), 1.10 (s, 9H). FABLRMS m/z 399 (M$^+$H). FABHRMS m/z 399.1388 (M$^+$H, Calc'd 399.1379). Anal. Calc'd for C$_{21}$H$_{22}$N$_2$O$_4$S: C, 63.30; H, 5.56; N, 7.03. Found: C, 63.45; H, 5.53; N, 7.08.

EXAMPLE 22

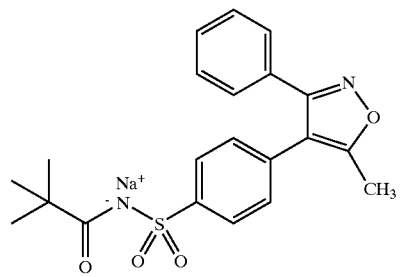

2,2-Dimethyl-N-[[4-(5-methyl-3-phenylisoxazol-4-yl)phenyl]sulfonyl]propanamide, sodium salt mp>300° C. $^1$H NMR (DMSO-d$_6$/300 MHz) 7.68 (d, 2H, J=8.1 Hz), 7.42–7.31 (m, 5H), 7.18 (d, 2H, J=8.1 Hz), 2.44 (s, 3H), 0.96 (s, 9H). FABLRMS m/z 421 (M$^+$H). FABHRMS m/z 421.1196 (M$^+$H, Calc'd 421.1198). Anal. Calc'd for C$_{21}$H$_{21}$N$_2$O$_4$SNa: C, 59.99; H, 5.03; N, 6.66. Found: C, 59.83; H, 5.08; N, 6.58.

EXAMPLE 23

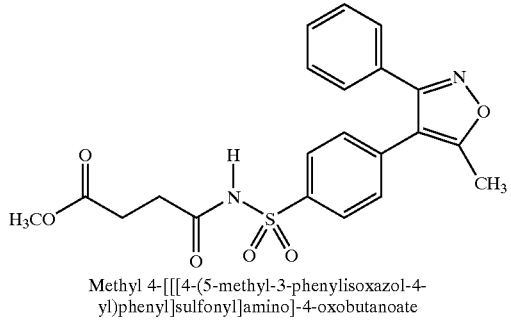

Methyl 4-[[[4-(5-methyl-3-phenylisoxazol-4-yl)phenyl]sulfonyl]amino]-4-oxobutanoate mp 114.9–117.7° C. $^1$H NMR (CDCl$_3$/300 MHz) 8.70 (brs, 1H), 8.04 (d, 2H, J=8.4 Hz), 7.38–7.26 (m, 7H), 3.66 (s, 3H), 2.67–2.57 (m, 4H), 2.50 (s, 3H), 1.10 (s, 9H). FABLRMS m/z 429 (M$^+$H). FABHRMS m/z 429.1102 (M$^+$H, Calc'd 429.1120). Anal. Calc'd for C$_{21}$H$_{20}$N$_2$O$_6$S: C, 58.87; H, 4.70; N, 6.54. Found: C, 58.61; H, 4.77; N, 6.44.

EXAMPLE 24

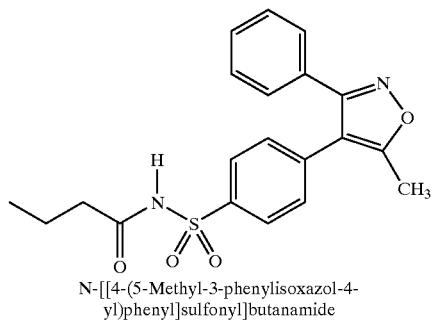

N-[[4-(5-Methyl-3-phenylisoxazol-4-yl)phenyl]sulfonyl]butanamide mp 173.2° C. $^1$H NMR (CDCl$_3$/300 MHz) 8.55 (brs, 1H), 8.05 (d, 2H, J=8.7 Hz), 7.40–7.29 (m, 7H), 2.50 (s, 3H), 2.86 (t, 2H, J=7.2 Hz), 1.61 (sext, 2H, J=7.2 Hz), 0.88 (t, 3H J=7.2 Hz). FABLRMS m/z 391 (M$^+$Li). FABHRMS m/z 385.1224 (M$^+$H, Calc'd 385.1222). Anal. Calc'd for $C_{20}H_{20}N_2O_4S$: C, 62.48; H, 5.24; N, 7.29. Found: C, 62.37; H, 5.28; N, 7.22.

EXAMPLE 25

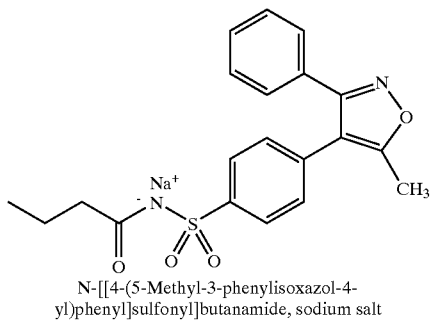

N-[[4-(5-Methyl-3-phenylisoxazol-4-yl)phenyl]sulfonyl]butanamide, sodium salt mp 273.5–277.7° C. $^1$H NMR (D$_2$O/300 MHz) 7.54 (d, 2H, J=8.4 Hz), 7.13–6.73 (m, 7H), 2.06 (s, 3H), 1.94 (t, 2H, J=7.2 Hz), 1.27 (sext, 2H, J=7.2 Hz), 0.55 (t, 3H, J=7.2 Hz). FABLRMS m/z 407 (M$^+$H). FABHRMS m/z 407.1065 (M$^+$H, Calc'd 407.1041). Anal. Calc'd. for $C_{20}H_{19}N_2O_4SNa$: C, 59.10; H, 4.71; N, 6.89. Found: C, 58.91; H, 4.77; N, 6.80.

EXAMPLE 26

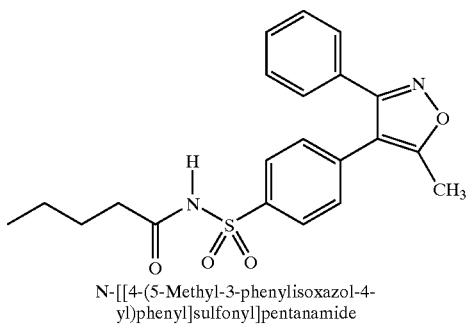

N-[[4-(5-Methyl-3-phenylisoxazol-4-yl)phenyl]sulfonyl]pentanamide mp 134.1–136.5° C. $^1$H NMR (CDCl$_3$/300 MHz) 8.58 (brs, 1H), 8.04 (d, 2H, J=8.6 Hz), 7.40–7.31 (m, 7H), 2.50 (s, 3H), 2.28 (t, 2H, J=7.5 Hz), 1.56 (pent, 2H, J=7.5 Hz), 1.27 (sext, 2H, J=7.5 Hz), 0.85 (t, 3H, J=7.5 Hz). FABLRMS m/z 399 (M$^+$H). FABHRMS m/z 399.1286 (M, Calc'd 399.1300). Anal. Calc'd for $C_{21}H_{22}N_2O_4S$: C, 63.30; H, 5.56; N, 7.03. Found: C, 63.25; H, 5.63; N, 9.69.

EXAMPLE 27

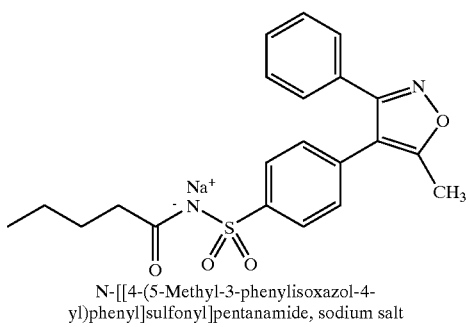

N-[[4-(5-Methyl-3-phenylisoxazol-4-yl)phenyl]sulfonyl]pentanamide, sodium salt mp 264.7° C. $^1$H NMR (DMSO-d$_6$/300 MHz) 7.71 (d, 2H, J=8.1 Hz), 7.43–7.32 (m, 5H), 7.18 (d, 2H, J=8.1 Hz), 2.43 (s, 3H), 1.90 (t, 2H, J=7.5 Hz), 1.35 (pent, 2H, J=7.5 Hz), 1.17 (sext, 2H, J=7.5 Hz), 0.78 (t, 3H, J=7.5 Hz). FABLRMS m/z 421 (M$^+$H). Anal. Calc'd for $C_{21}H_{21}N_2O_4SNa$: C, 59.99; H, 5.03; N, 6.66. Found: C, 59.85; H, 5.08; N, 6.62.

EXAMPLE 28

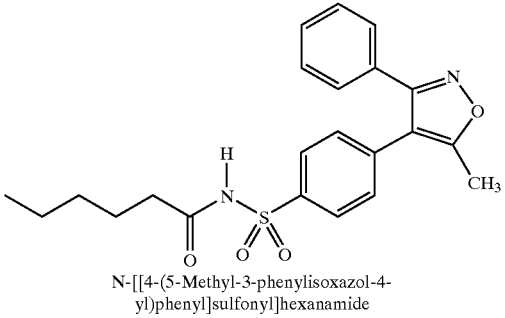

N-[[4-(5-Methyl-3-phenylisoxazol-4-yl)phenyl]sulfonyl]hexanamide $^1$H NMR (CDCl$_3$/300 MHz) 8.50 (brs, 1H), 8.04 (d, 2H, J=8.4 Hz), 7.40–7.30 (m, 7H), 2.50 (s, 3H), 2.27 (t, 2H, J=7.2 Hz), 1.58 (pent, 2H, J=7.2 Hz), 1.27–1.19 (m, 4H), 0.84 (t, 3H, J=7.2 Hz). FABLRMS m/z 413 (M$^+$H). FABHRMS m/z 413.1517 (M$^+$H, Calc'd 413.1535). Anal. Calc'd for $C_{22}H_{24}N_2O_4S$: C, 64.06; H, 5.86; N, 6.79. Found: C, 64.04; H, 5.85; N, 6.70.

EXAMPLE 29

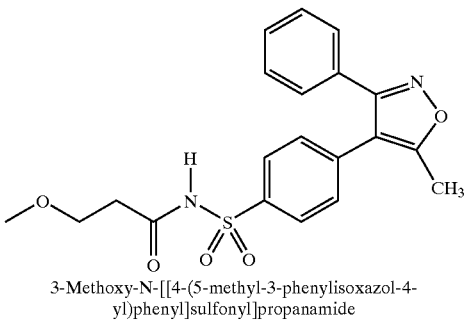

3-Methoxy-N-[[4-(5-methyl-3-phenylisoxazol-4-yl)phenyl]sulfonyl]propanamide mp 139.7–140.9° C. $^1$H NMR (CDCl$_3$/300 MHz) 9.34 (brs, 1H), 8.05 (d, 2H, J=8.5 Hz), 7.37 (m, 7H), 3.62 (t, 2H, J=5.5 Hz), 3.43 (s, 3H), 2.54 (t, 2H, J=5.5 Hz), 2.51 (s, 3H). FABHRMS m/z 400.1071 (M$^+$, $C_{20}H_{20}N_2O_5S$ Calc'd 400.1093).

EXAMPLE 30

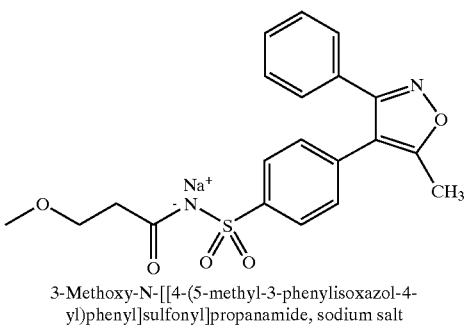

3-Methoxy-N-[[4-(5-methyl-3-phenylisoxazol-4-yl)phenyl]sulfonyl]propanamide, sodium salt mp 240.7–243.2° C. $^1$H NMR (D$_2$O/300 MHz) 7.63 (d, 2H, J=8.5 Hz), 7.33 (m, 1H), 7.20 (m, 4H), 7.16 (d, 2H, J=8.5 Hz), 3.49 (t, 2H, J=6.2 Hz), 3.11 (s, 3H), 2.29 (s and t overlapped, 5H, J=6.2 Hz). FABHRMS m/z 429.1074 (M⁺Li), C$_{20}$H$_{19}$N$_2$O$_5$SNaLi Calc'd 429.1072).

EXAMPLE 31

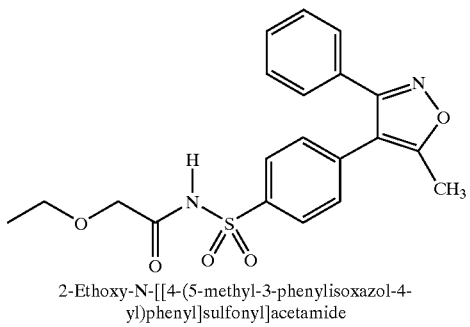

2-Ethoxy-N-[[4-(5-methyl-3-phenylisoxazol-4-yl)phenyl]sulfonyl]acetamide mp 131.3–132.2° C. ¹H NMR (CDCl$_3$/300 MHz) 8.98 (brs, 1H), 8.08 (d, 2H, J=8.7 Hz), 7.37 (m, 7H), 3.95 (s, 2H), 3.58 (q, 2H, J=7.0 Hz), 2.51 (s, 3H), 1.26 (t, 3H, J=7.0 Hz). FABHRMS m/z 400.1093 (M⁺), C$_{20}$H$_{20}$N$_2$O$_5$S Calc'd 400.1072).

EXAMPLE 32

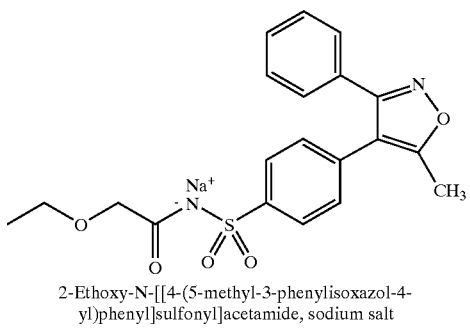

2-Ethoxy-N-[[4-(5-methyl-3-phenylisoxazol-4-yl)phenyl]sulfonyl]acetamide, sodium salt mp 207.2–210.0° C. ¹H NMR (D$_2$O/300 MHz) 7.67 (d, 2H, J=8.5 Hz), 7.33 (m, 1H), 7.26–7.19 (m, 6H), 3.80 (s, 2H), 3.36 (q, 2H, J=7.1 Hz), 2.33 (s, 3H), 1.00 (t, 3H, J=7.1 Hz). FABHRMS m/z 423.0992 (M⁺H), C$_{20}$H$_{20}$N$_2$O$_5$SNa Calc'd 423.0991).

EXAMPLE 33

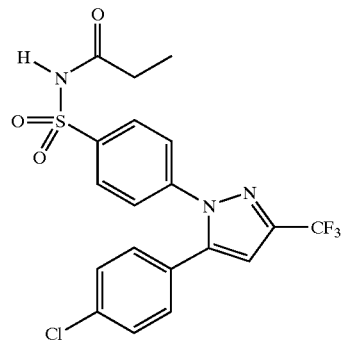

N-[[4-[5-(4-Chlorophenyl)-3-(trifluoromethyl)-1H-pyrazol-1-yl]phenyl]sulfonyl]propanamide mp 77.9–85.1° C. Anal. Calc'd for C$_{19}$H$_{15}$ClF$_3$N$_3$O$_3$S: C, 49.84; H, 3.30; N, 9.18. Found: C, 49.83; H, 3.36; N, 9.10.

EXAMPLE 34

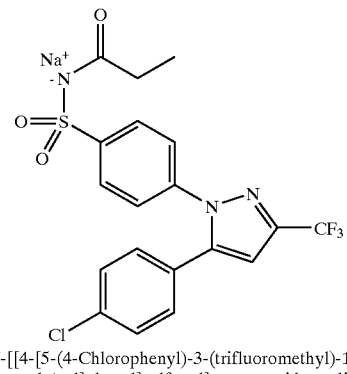

N-[[4-[5-(4-Chlorophenyl)-3-(trifluoromethyl)-1H-pyrazol-1-yl]phenyl]sulfonyl]propanamide, sodium salt mp>300° C. Anal. Calc'd for C$_{19}$H$_{14}$ClF$_3$N$_3$O$_3$SNa: C, 47.56; H, 2.94; N, 8.76. Found: C, 47.51; H, 3.02; N, 8.72.

EXAMPLE 35

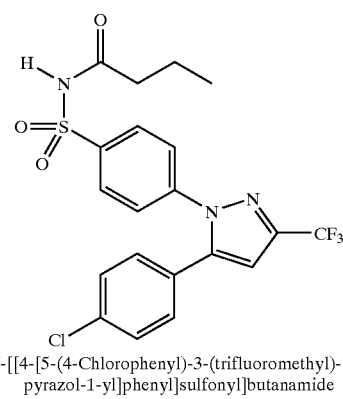

N-[[4-[5-(4-Chlorophenyl)-3-(trifluoromethyl)-1H-pyrazol-1-yl]phenyl]sulfonyl]butanamide ¹H NMR (CDCl$_3$/300 MHz) 8.1 (d, 2H, J=8.7 Hz), 7.94 (brs, 1H), 7.5 (d, 2H, J=8.7 Hz), 7.37 (d, 2H, J=8.4 Hz), 7.17 (d, 2H, J=8.4 Hz), 6.79 (S, 1H), 2.24 (t, 2H, J=7.5 Hz), 1.62 (m, 2H), 0.9 (t, 3H, J=7.5 Hz). FABLRMS m/z 494 (M⁺H).

EXAMPLE 36

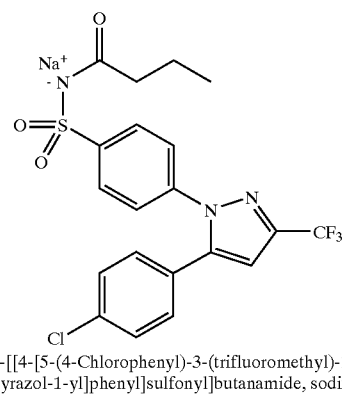

N-[[4-[5-(4-Chlorophenyl)-3-(trifluoromethyl)-1H-pyrazol-1-yl]phenyl]sulfonyl]butanamide, sodium salt mp 285.4–286.5° C. ¹H NMR (CD$_3$OD/300 MHz) 7.95 (d, 2H, J=8.7 Hz), 7.37 (m, 4H), 7.27 (d, 2H, J=9.0 Hz), 6.96 (S, 1H), 2.1 (t, 2H, 6.9 Hz), 1.55 (m, 2H), 0.84 (t, 3H, J=7.2 Hz).

EXAMPLE 37

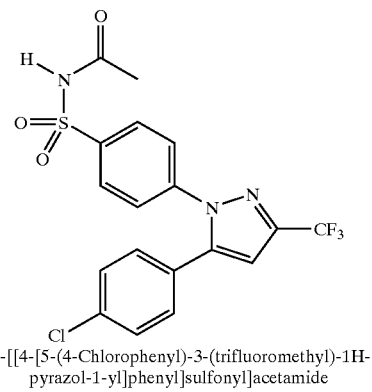

N-[[4-[5-(4-Chlorophenyl)-3-(trifluoromethyl)-1H-pyrazol-1-yl]phenyl]sulfonyl]acetamide mp 161.9–162.7° C. $^1$H NMR (CDCl$_3$/300 MHz) 8.6 (brs, 1H), 8.07 (d, 2H, J=6.9Hz), 7.5 (d, 2H, J=6.9 Hz), 7.38 (d, 2H, J=6.9 Hz), 7.18 (d, 2H, J=6.9 Hz), 6.79 (s, 1H), 2.07 (s, 3H).

EXAMPLE 38

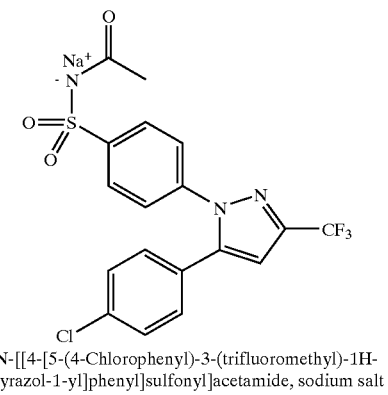

N-[[4-[5-(4-Chlorophenyl)-3-(trifluoromethyl)-1H-pyrazol-1-yl]phenyl]sulfonyl]acetamide, sodium salt mp 269.8–272° C. $^1$H NMR (D$_2$O/300 MHz) 7.73 (d, 2H, J=8.7 Hz), 7.3 (d, 2H, J=8.7 Hz), 7.23 (d, 2H, J=8.4 Hz), 7.06 (d, 2H, J=8.4 Hz), 6.87 (s, 1H), 1.8 (s, 3H).

EXAMPLE 39

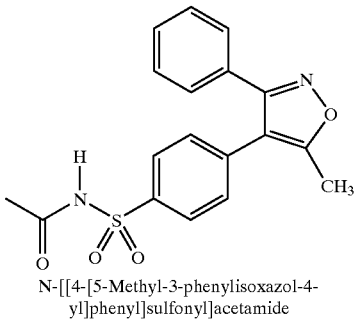

N-[[4-[5-Methyl-3-phenylisoxazol-4-yl]phenyl]sulfonyl]acetamide mp 169.3–170.6° C. Anal. Calc'd for C$_{18}$H$_{16}$N$_2$O$_4$S: C, 60.66; H, 4.53; N, 7.86. Found C, 60.57; H, 4.59; N, 7.81.

EXAMPLE 40

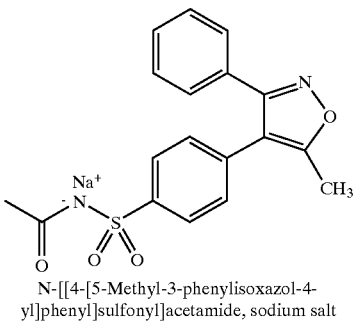

N-[[4-[5-Methyl-3-phenylisoxazol-4-yl]phenyl]sulfonyl]acetamide, sodium salt mp 245.6–247° C. Anal. Calc'd for C$_{18}$H$_{15}$N$_2$O$_4$SNa.H$_2$O: C, 54.54; H, 4.32; N, 7.07. Found C, 54.47; H, 4.34; N, 7.07.

EXAMPLE 41

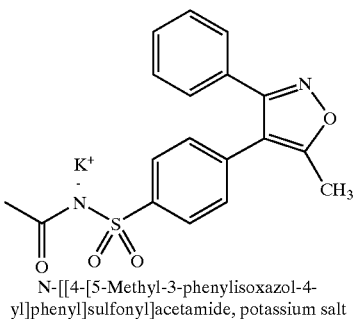

N-[[4-[5-Methyl-3-phenylisoxazol-4-yl]phenyl]sulfonyl]acetamide, potassium salt mp 279.7–283.7° C. $^1$H NMR (D$_2$O/30 MHz) 7.62 (d, 2H, J=8.4 Hz), 7.2 (m, 7H), 2.27 (s, 3H), 1.77 (s, 3H).

EXAMPLE 42

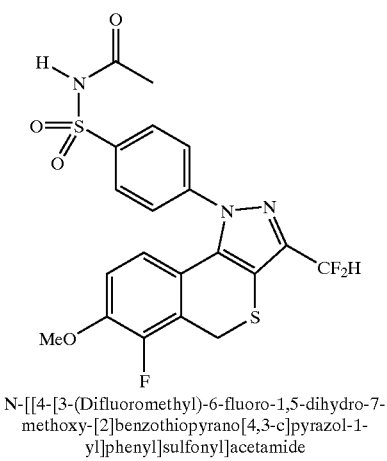

N-[[4-[3-(Difluoromethyl)-6-fluoro-1,5-dihydro-7-methoxy-[2]benzothiopyrano[4,3-c]pyrazol-1-yl]phenyl]sulfonyl]acetamide $^1$H NMR (300 MHz/CDCl$_3$) 8.1 (d, 2H, J=6.9 Hz), 7.61 (d, 2H, J=6.9 Hz), 6.69 (m, 3H), 4.0 (s, 2H), 3.82 (s, 3H), 1.96 (s, 3H). FABLRMS m/z 484 (M$^+$H).

EXAMPLE 43

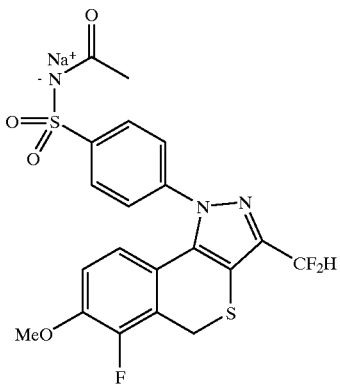

N-[[4-[3-(Difluoromethyl)-6-fluoro-1,5-dihydro-7-methoxy-[2]benzothiopyrano[4,3-c]pyrazol-1-yl]phenyl]sulfonyl]acetamide, sodium salt mp>300° C. $^1$H NMR (CD$_3$OD/300 MHz) 8.04 (d, 2H, J=6.6 Hz), 7.6 (d, 2H, J=6.6 Hz), 6.82 (m, 3H), 4.08 (s, 2H), 3.85 (s, 3H), 1.90 (s, 3H).

EXAMPLE 44

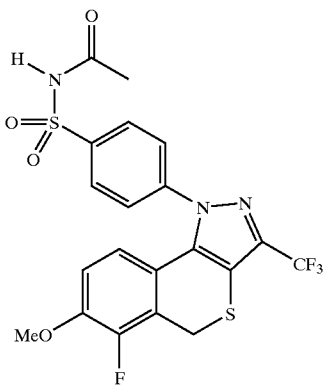

N-[[4-[6-Fluoro-1,5-dihydro-7-methoxy-3-(trifluoromethyl)-[2]benzothiopyrano[4,3-c]pyrazol-1-yl]phenyl]sulfonyl]acetamide $^1$H NMR (CDCl$_3$/300 MHz) 8.06 (d, 2H, J=8.4 Hz), 7.6 (d, 2H, J=8.4 Hz), 6.68 (d, 2H, J=8.7 Hz), 6.50 (d, 2H, J=8.7 Hz), 3.97 (s, 2H), 3.79 (s, 3H), 1.92 (s, 3H). FABLRMS m/z 502 (M$^+$H).

EXAMPLE 45

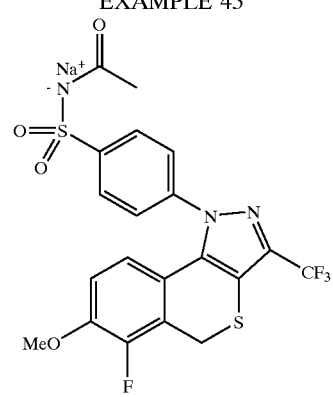

N-[[4-[6-Fluoro-1,5-dihydro-7-methoxy-3-(trifluoromethyl)-[2]benzothiopyrano[4,3-c]pyrazol-1-yl]phenyl]sulfonyl]acetamide, sodium salt mp 183–191.1° C. $^1$H NMR (CD$_3$OD/300 MHz) 8.06 (d, 2H, J=8.7 Hz), 7.62 (d, 2H, J=8.7 Hz), 6.9 (d, 2H, J=8.7 Hz), 6.6 (d, 2H, J=8.7 Hz), 4.11 (s, 2H), 3.85 (s, 3H), 1.90 (s, 3H).

EXAMPLE 46

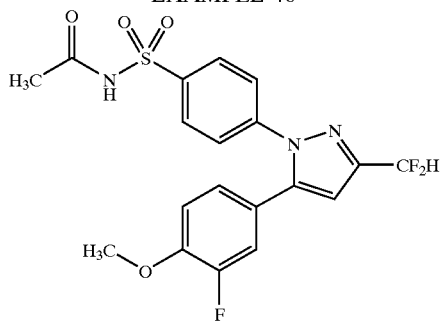

N-[[4-[3-(Difluoromethyl)-5-(3-fluoro-4-methoxyphenyl)-1H-pyrazol-1-yl]phenyl]sulfonyl]acetamide mp 173–175° C. $^1$H NMR (acetone-d$_6$/300 MHz) 8.1 (d, 2H, J=8.9 Hz), 7.6 (d, 2H, J=8.9 Hz), 7.2–6.8 (m, 6H), 3.9 (s, 3H). Anal. Calc'd for C$_{19}$H$_{16}$N$_3$F$_3$O$_4$S: C, 51.94; H, 3.67; N, 9.56. Found: C, 51.80; H, 3.72; N, 9.47.

EXAMPLE 47

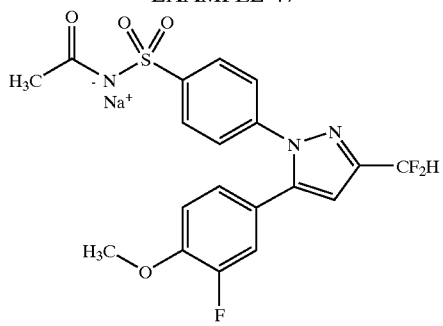

N-[[4-[3-(Difluoromethyl)-5-(3-fluoro-4-methoxyphenyl)-1H-pyrazol-1-yl]phenyl]sulfonyl]acetamide, sodium salt mp 140.1–146.0° C. $^1$H NMR (D$_2$O/300 MHz) 7.7 (d, 2H, J=8.4 Hz), 7.2 (d, 2H, J=8.4 Hz), 6.9–6.6 (m, 5H), 3.7 (s, 3H), 1.8 (s, 3H). Anal. Calc'd for C$_{19}$H$_{15}$N$_3$F$_3$O$_4$SNa+ 3.06% H$_2$O: C, 47.95; H, 3.52; N, 8.83. Found: C, 47.94; H, 3.42; N, 8.78.

EXAMPLE 48

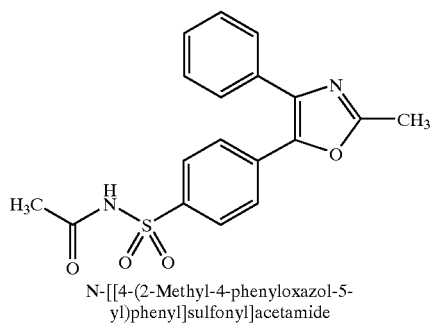

N-[[4-(2-Methyl-4-phenyloxazol-5-yl)phenyl]sulfonyl]acetamide mp 220.7–221.0° C. $^1$H NMR (acetone-$d_6$/300 MHz) 8.0 (d, 2H, J=8.7 Hz), 7.8 (d, 2H, J=9.0 Hz), 7.6 (m, 2H), 7.4 (m, 3H), 2.5 (s, 3H), 2.0 (s, 3H). Anal. Calc'd for $C_{18}H_{16}N_2O_4S$: C, 60.66; H, 4.53; N, 7.86. Found: C, 60.54; H, 4.56; N, 7.90.

EXAMPLE 49

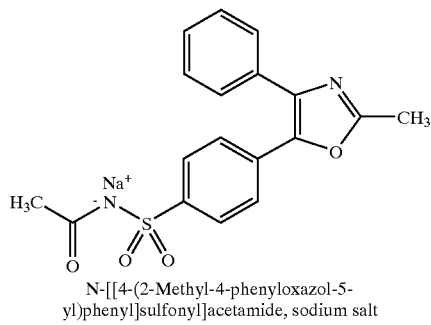

N-[[4-(2-Methyl-4-phenyloxazol-5-yl)phenyl]sulfonyl]acetamide, sodium salt mp 259.9–260.0° C. $^1$H NMR ($D_2O$/300 MHz) 7.6 (d, 2H, J 8.4 Hz), 7.4 (d, 2H, J 8.4 Hz), 7.3 (m, 5H), 2.3 (s, 3H), 1.8 (s, 3H). Anal. Calc'd for $C_{18}H_{15}N_2O_4SNa+5.94\%\ H_2O$: C, 53.74; H, 4.42; N, 6.96. Found: C, 53.73; H, 4.28; N, 6.94.

EXAMPLE 50

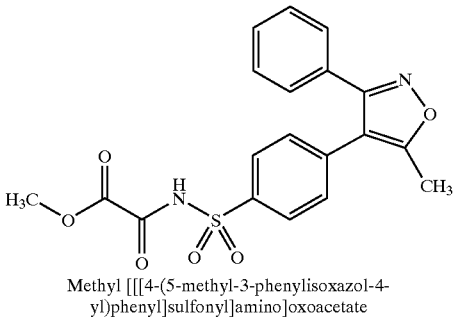

Methyl [[[4-(5-methyl-3-phenylisoxazol-4-yl)phenyl]sulfonyl]amino]oxoacetate mp 171.1–172.3° C. $^1$H NMR ($CDCl_3$/300 MHz) 9.4 (bs, 1H), 8.1 (d, 2H, J=8.7 Hz), 7.4–7.2 (m, 7H), 7.6 (m, 2H), 3.9 (s, 3H), 2.5 (s, 3H). Anal. Calc'd for $C_{19}H_{16}N_2O_6S$: C, 56.99; H, 4.03; N, 7.00. Found: C, 56.74; H, 3.96; N, 6.94.

EXAMPLE 51

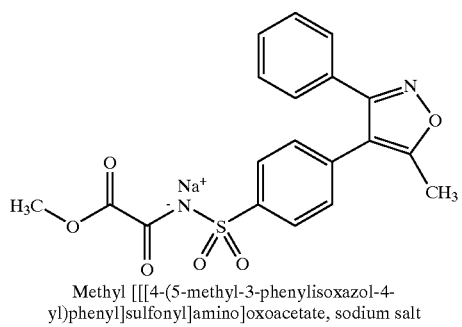

Methyl [[[4-(5-methyl-3-phenylisoxazol-4-yl)phenyl]sulfonyl]amino]oxoacetate, sodium salt mp 146.0–151.8° C. $^1$H NMR (DMSO-$d_6$/300 MHz) 7.8–7.7 (m, 2H), 7.5–7.2 (m, 7H), 3.5 (s, 3H), 2.5 (s, 3H). Anal. Calc'd for $C_{19}H_{15}N_2O_6SNa+3.22\%\ H_2O$: C, 52.29; H, 3.82; N, 6.42. Found: C, 52.28; H, 3.77; N, 6.44.

EXAMPLE 52

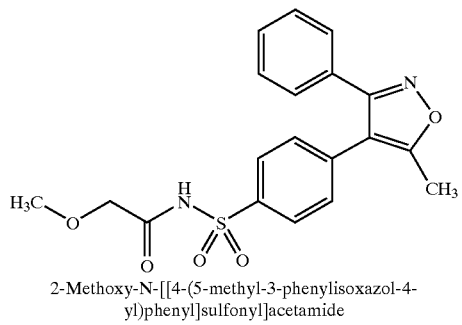

2-Methoxy-N-[[4-(5-methyl-3-phenylisoxazol-4-yl)phenyl]sulfonyl]acetamide mp 123.9–125.3° C. $^1$H NMR (acetone-$d_6$/300 MHz) 8.0 (d, 2H, J=8.7 Hz), 7.5 (d, 2H, J=8.7 Hz), 7.5–7.4 (m, 5H), 4.0 (s, 2H), 3.4 (s, 3H), 2.5 (s, 3H). Anal. Calc'd for $C_{19}H_{18}N_2O_5S$: C, 59.06; H, 4.70; N, 7.25. Found: C, 59.14; H, 4.73; N, 725.

EXAMPLE 53

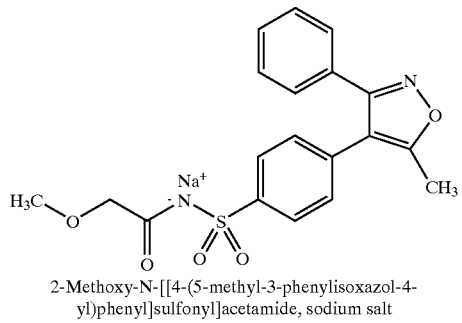

2-Methoxy-N-[[4-(5-methyl-3-phenylisoxazol-4-yl)phenyl]sulfonyl]acetamide, sodium salt mp 276.9–277.9° C. $^1$H NMR (DMSO-$d_6$/300 MHZ) 7.7 (d, 2H, J=8.4 Hz), 7.5–7.3 (m, 5H), 7.2 (d, J=8.4 Hz, 2H), 3.6 (s, 2H), 3.2 (s, 3H), 2.4 (s, 3H). FABHRMS m/z 409.0848 ($M^+H$, Calc'd 409.0851).

EXAMPLE 54

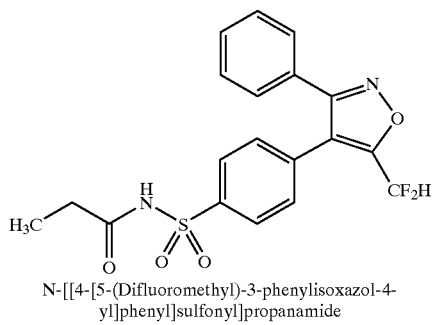

N-[[4-[5-(Difluoromethyl)-3-phenylisoxazol-4-yl]phenyl]sulfonyl]propanamide mp 136.9–141.0° C. $^1$H NMR (acetone-$d_6$/300 MHz) 10.7 (bs, 1H), 8.1 (d, 2H, J=8.4 Hz), 7.6 (d, 2H, J=8.4 Hz), 7.6–7.4 (m, 5H), 7.2 (t, 1H, J=52.2 Hz), 2.4 (t, 2H, J=7.5 Hz), 1.0 (t, 3H, J=7.5 Hz). Anal. Calc'd for $C_{19}H_{16}F_2N_2O_4S$: C, 56.15; H, 3.97; N, 6.89. Found: C, 56.10; H, 3.93; N, 6.81.

EXAMPLE 55

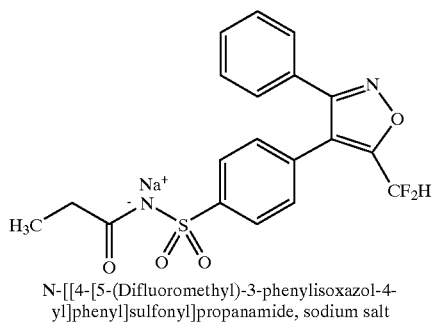

N-[[4-[5-(Difluoromethyl)-3-phenylisoxazol-4-yl]phenyl]sulfonyl]propanamide, sodium salt mp 287.8–293.6° C. $^1$H NMR (DMSO-$d_6$/300 MHz) 7.7 (d, 2H, J=8.1 Hz), 7.5–7.1 (m, 8H), 1.9 (dd, 2H, J=7.5 Hz), 0.8 (t, 3H, J=7.5 Hz). Anal. Calc'd for $C_{19}H_{15}N_2F_2NaO_4S$+ 2.04% $H_2O$: C, 52.17; H, 3.63; N, 6.45. Found: C, 52.18; H, 3.69; N, 6.41.

EXAMPLE 56

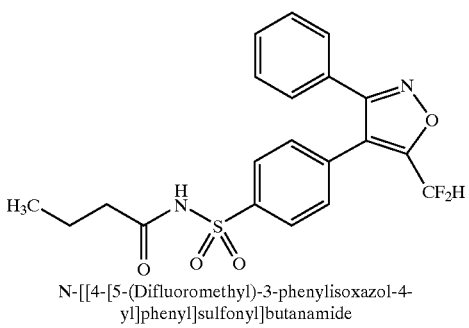

N-[[4-[5-(Difluoromethyl)-3-phenylisoxazol-4-yl]phenyl]sulfonyl]butanamide mp 154.9–155.9° C. $^1$H NMR (acetone-$d_6$/300 MHz) 10.7 (bs, 1H), 8.1 (d, 2H, J=8.4 Hz), 7.6 (d, 2H, J=8.4 Hz), 7.6–7.4 (m, 5H), 7.2 (t, 1H, J=51.9 Hz), 2.3 (dd, 2H, J=7.2 Hz), 1.6 (m, 2H), 0.8 (t, 3H, J=7.2 Hz). Anal. Calc'd for $C_{20}H_{18}F_2N_2O_4S$: C, 57.14; H, 4.32; N, 6.66. Found: C, 57.18; H, 4.37; N, 6.65.

EXAMPLE 57

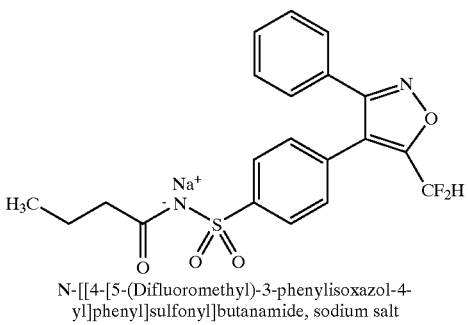

N-[[4-[5-(Difluoromethyl)-3-phenylisoxazol-4-yl]phenyl]sulfonyl]butanamide, sodium salt mp 281.7–286.3° C. $^1$H NMR (DMSO-$d_6$/300 MHz) 7.7 (d, 2H, J=8.1 Hz), 7.6–7.1 (m, 8H), 1.9 (dd, 2H, J=7.2 Hz), 1.4 (m, 2H), 0.7 (t, 3H, J=7.5 Hz). Anal. Calc'd for $C_{20}H_{17}N_2F_2NaO_4S$+2.25% $H_2O$: C, 53.07; H, 3.96; N, 6.17. Found: C, 53.08; H, 4.04; N, 6.19.

EXAMPLE 58

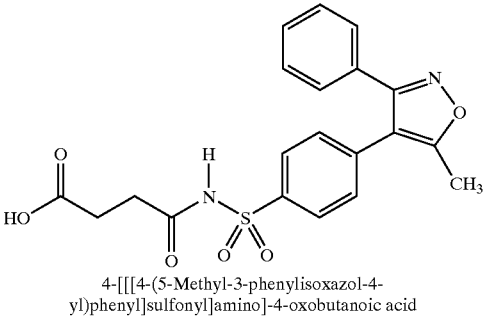

4-[[[4-(5-Methyl-3-phenylisoxazol-4-yl)phenyl]sulfonyl]amino]-4-oxobutanoic acid mp 158.4–165.4° C. $^1$H NMR (CDCl$_3$/300 MHz) 8.04 (m, 2H, J=8.7 Hz), 7.45–7.25 (m, 7H), 2.75–2.65 (m, 2H), 2.65–2.53 (m, 2H), 2.51 (s, 3H). FABLRMS m/z 415 (M$^+$H). FABHRMS m/z 415.0958 (M$^+$H, Calc'd 415.0964). Anal. Calc'd for $C_{20}H_{18}N_2O_6S$: C, 57.96; H, 4.38; N, 6.76. Found: C, 57.71; H, 4.81; N, 6.67.

EXAMPLE 59

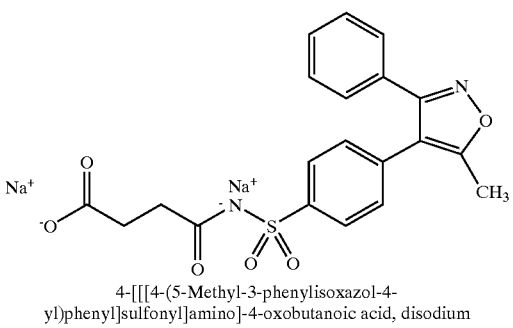

4-[[[4-(5-Methyl-3-phenylisoxazol-4-yl)phenyl]sulfonyl]amino]-4-oxobutanoic acid, disodium mp>300° C. $^1$H NMR (D$_2$O/300 MHz) 7.68 (d, 2H, J 8.5 Hz), 7.39–7.20 (m, 7H), 2.34 (s, 3H), 2.33–2.15 (m, 4 H). Anal. Calc'd for $C_{20}H_{16}N_2O_6SNa_2$. 0.95 $H_2O$: C, 50.53; H, 3.79; N, 5.89. Found: C, 50.52; H, 3.82; N, 5.89.

EXAMPLE 60

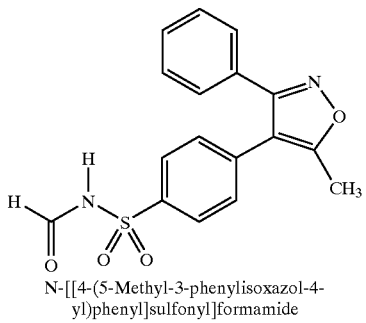

N-[[4-(5-Methyl-3-phenylisoxazol-4-yl)phenyl]sulfonyl]formamide mp 111–122° C. $^1$H NMR (CDC$_3$/300 MHz) 8.69 (br s, 1H), 7.92 (d, 2H, J=8.5 Hz), 7.48–7.31 (m, 7H), 2.52 (s, 3H). FABLRMS m/z 343 (M$^+$H). FABHRMS m/z 343.0753 (M$^+$H, Calc'd 343.0753). Anal. Calc'd for C$_{17}$H$_{14}$N$_2$O$_4$S: C, 59.64; H, 4.12; N, 8.18; Found C, 59.59; H, 4.17; N, 8.07.

EXAMPLE 61

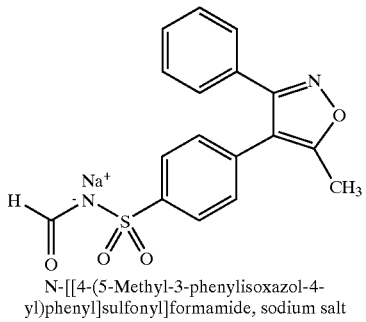

N-[[4-(5-Methyl-3-phenylisoxazol-4-yl)phenyl]sulfonyl]formamide, sodium salt mp 198–204° C. $^1$H NMR (D$_2$O/300 MHz) 8.57 (s, 1H), 7.64 (d, 2H, J=8.3 Hz), 7.38–7.13 (m, 7H), 2.31 (s, 3H). FABLRMS m/z 365 (M$^+$H). FABHRMS m/z 365.0565 (M$^+$H, Calc'd 365.0572). Anal. Calc'd for C$_{17}$H$_{13}$N$_2$O$_4$SNa 0.73 EtOH.0.51 H$_2$O: C, 54.46; H, 4.55; N, 6.88; Found C, 54.46; H, 4.44; N, 6.74.

EXAMPLE 62

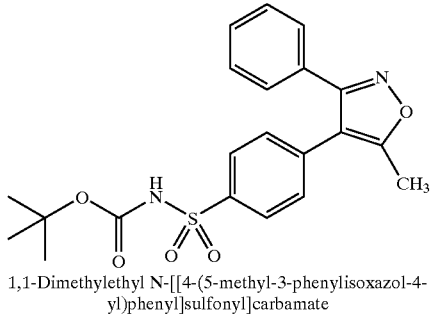

1,1-Dimethylethyl N-[[4-(5-methyl-3-phenylisoxazol-4-yl)phenyl]sulfonyl]carbamate mp 168–171° C. $^1$H NMR (CDCl$_3$/300 MHz) 8.01(d, 2H, J=8.7 Hz), 7.51 (s, 1H), 7.46–7.30 (m, 7H), 2.50 (s, 3H), 1.40 (s, 9H). FABLRMS m/z 415 (M$^+$H). FABHRMS m/z 415.1337 (M$^+$H, Calc'd 415.1328). Anal. Calc'd for C$_{21}$H$_{22}$N$_2$O$_5$S: C, 60.86; H, 5.35; N, 6.76; Found: C, 60.79; H, 5.40; N, 6.75.

EXAMPLE 63

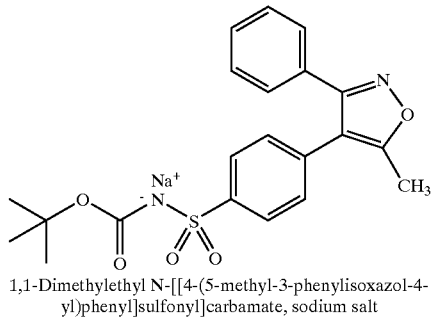

1,1-Dimethylethyl N-[[4-(5-methyl-3-phenylisoxazol-4-yl)phenyl]sulfonyl]carbamate, sodium salt mp 241–243° C. $^1$H NMR (D$_2$O/300 MHz) 7.67 (d, 2H, J=8.3 Hz), 7.42–7.17 (m, 7H), 2.35 (s, 3H), 1.11 (s, 9H). FABLRMS (M$^+$H) m/z 437. FABHRMS m/z 437.1171(M$^+$H, Calc'd 437.1147). Anal. Calc'd for C$_{21}$H$_{21}$N$_2$O$_5$SNa . 0.96 H$_2$O: C, 55.52; H, 5.10; N, 6.17; Found C, 55.50; H, 5.06; N, 6.29.

EXAMPLE 64

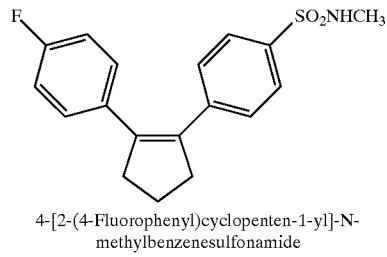

4-[2-(4-Fluorophenyl)cyclopenten-1-yl]-N-methylbenzenesulfonamide mp 121–122° C. $^1$H NMR (CDCl$_3$) δ 2.08 (p, J=9 Hz, 2H), 2.67 (s, 3H), 2.91 (t, J=9 Hz, 4H), 4.24 (br s, 1H), 6.92 (d, J=9 Hz, 2H), 7.07–7.13 (m, 2H), 7.28 (d, J=9 Hz, 2H), 7.67 (d, J=9 Hz, 2H). MS (FAB) m/z 332 (M+H)$^+$. Anal. Calc'd for C$_{18}$H$_{18}$NO$_2$SF: C, 65.24; H, 5.47; N, 4.23. Found: C, 65.02; H, 5.69; N, 4.20.

EXAMPLE 65

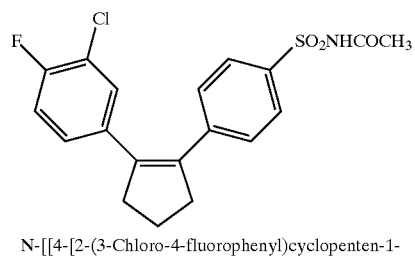

N-[[4-[2-(3-Chloro-4-fluorophenyl)cyclopenten-1-yl]phenyl]sulfonyl]acetamide mp 127–129° C. $^1$H NMR (CDCl$_3$) δ 2.03–2.14 (m, 5H), 2.84–2.95 (m, 4H), 6.92–7.00 (m, 2H), 7.18 (dd, J=2, 8 Hz, 1H), 7.29 (d, J=9 Hz, 2H), 7.88 (d, J=9 Hz, 2H), 8.20 (br s, 1H). MS (FAB) m/z 394 (M+H)$^+$. HRMS Calc'd for (M+H) 394.0680. Found 394.0630. Anal. Calc'd for C$_{19}$H$_{17}$NClFO$_3$S & 0.49 H$_2$O): C, 56.68; H, 4.50; N, 3.48. Found: C, 56.65; H, 4.39; N, 3.74.

EXAMPLE 66

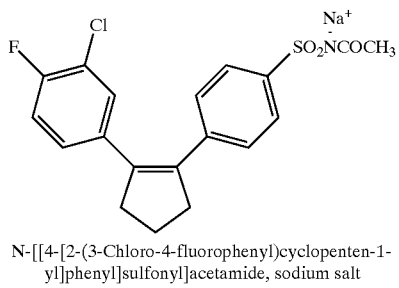

N-[[4-[2-(3-Chloro-4-fluorophenyl)cyclopenten-1-yl]phenyl]sulfonyl]acetamide, sodium salt mp>180° C. $^1$H NMR (D$_2$O) δ 1.77 (s, 3H), 1.90 (p, J=8 Hz, 2H), 2.67–2.78 (m, 4H), 6.94 (d, J=8 Hz, 2H), 7.13 (s, 1H), 7.17 (d, J=8 Hz, 2H), 7.53 (d, J=8 Hz, 2H). Anal. Calc'd for (C$_{19}$H$_{16}$NClFO$_3$SNa & 0.15 NaOH & 0.85 H$_2$O): C, 52.21; H, 4.12; N, 3.20; Na, 6.03. Found: C, 52.20; H, 4.02; N, 3.22; Na, 6.02.

EXAMPLE 67

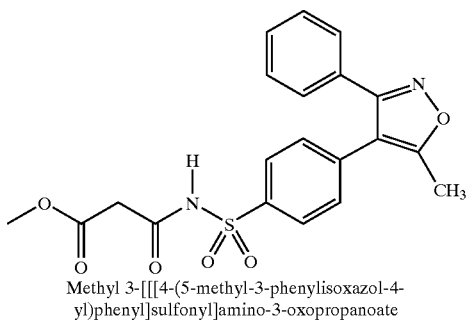

Methyl 3-[[[4-(5-methyl-3-phenylisoxazol-4-yl)phenyl]sulfonyl]amino-3-oxopropanoate $^1$H NMR (acetone-d$_6$/300 MHz) 8.04 (d, J=8.5 Hz, 2H), 7.49 (d, J=8.5 Hz, 2H), 7.40–7.39 (m, 5H), 3.64 (s, 3H), 3.47 (s, 2H), 2.53 (s, 3H). FABLRMS m/z 415 (M$^+$H).

EXAMPLE 68

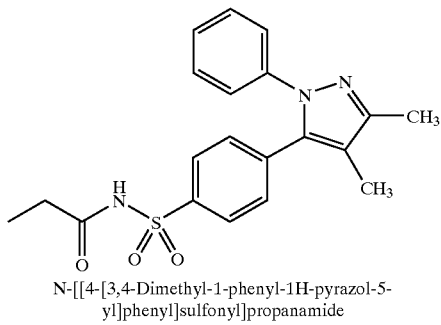

N-[[4-[3,4-Dimethyl-1-phenyl-1H-pyrazol-5-yl]phenyl]sulfonyl]propanamide mp 187.4–188.7° C. $^1$H NMR (acetone d$_6$/300 MHz) 8.0 (d, 2H, J=8.5 Hz), 7.43 (d, 2H, J=8.5 Hz), 7.23 (m, 5H), 2.27 (s, 3H), 2.05 (s, 3H). Anal. Calc'd for C$_{20}$H$_{21}$N$_3$O$_3$S: C, 62.64; H, 5.52; N, 10.96. Found C, 62.83; H, 5.61; N, 10.90.

EXAMPLE 69

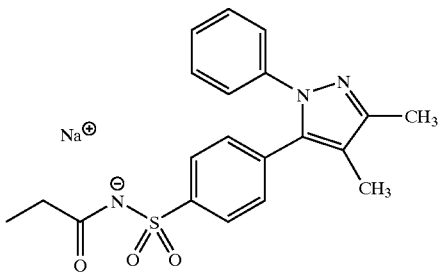

N-[[4-[3,4-Dimethyl-1-phenyl-1H-pyrazol-5-yl]phenyl]sulfonyl]propanamide, sodium salt mp 264.0–267.6° C. $^1$H NMR (DMSO d6/300 MHz) 7.68 (d, 2H, J=8.4 Hz), 7.25 (m, 3H), 7.11 (m, 4H), 2.19 (s, 3H), 1.94 (s, 3H).

EXAMPLE 70

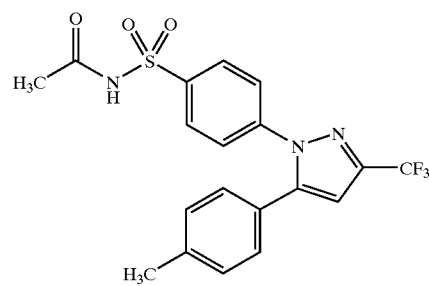

N-[[4-[5-(4-Methylphenyl)-3-(trifluoromethyl)-1H-pyrazol-1-yl]phenyl]sulfonyl]acetamide 4-[5-(4-Methylphenyl)-3-(trifluoromethyl)-1H-pyrazol-1-yl]benzenesulfonamide (0.60 g, 1.57 mmol) was heated in 2 mL acetyl chloride and 2 mL acetic acid at reflux for 2 h. An additional 2 mL acetyl chloride was added and the mixture was heated to reflux for an additional 5 h. The mixture was cooled and concentrated. Recrystallization from ether/hexane furnished the product as a white solid: Anal. Calc'd for C$_{19}$H$_{16}$N$_3$O$_3$SF$_3$: C, 53.90; H, 3.81; N, 9.92; S, 7.57. Found: C, 54.04; H, 3.80; N, 9.93; S, 7.66.

EXAMPLE 71

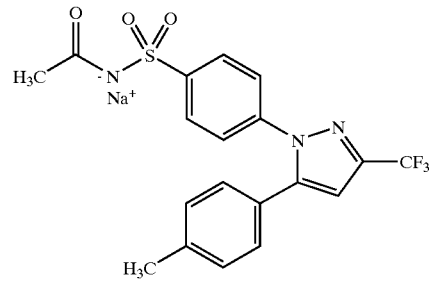

N-[[4-[5-(4-Methylphenyl)-3-(trifluoromethyl)-1H-pyrazol-1-yl]phenyl]sulfonyl]acetamide, sodium salt To 300 mg (0.71 mmol) of N-[[4-[5-(4-methylphenyl)-3-(trifluoromethyl)-1H-pyrazol-1-yl]phenyl]sulfonyl]acetamide (Example 70) in 4 mL EtOH was added 40 μL of 50% NaOH (0.76 mmol) and the mixture was stirred at room temperature for 1 h. Concentration provided the sodium salt as a white solid.

EXAMPLE 72

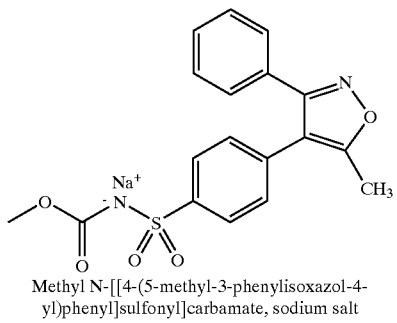

Methyl N-[[4-(5-methyl-3-phenylisoxazol-4-yl)phenyl]sulfonyl]carbamate, sodium salt A solution of 4-[5-methyl-3-(phenyl)isoxazol-4-yl]benzenesulfonamide (1.920 g, 6.11 mmol) in 40 mL of THF was treated with methyl chloroformate (1.16 mL, 1.38 g, 14.60 mmol) and then 1,8-diazabicyclo[5.4.0]undec-7-ene (DBU) (2.80 mL, 2.79 g, 18.33 mmol) at room temperature. After 48 hours, the resulting mixture was partitioned between ethyl acetate and KHSO$_4$ solution. The organic phase was washed with brine, dried over MgSO$_4$, filtered and concentrated in vacuo yielding a pale yellow clear oil. This oil was purified by running two flash chromatographic columns (1st eluant 1:1; hexane: ethyl acetate; 2nd eluant CH$_2$Cl$_2$ with THF) yielding the crude compound which was suitable for use without further purification. The crude compound was dissolved in 8 mL of chloroform and treated with 2 mL of saturated aqueous NaHCO$_3$. The product separated as a crystalline solid and was collected by filtration to afford pure salt as white needles (0.607 g, 25%): mp 267.4–275.0° C. $^1$H NMR (D$_2$O/300 MHz) 7.68 (d, 2H, J=8.5 Hz), 7.39–7.12 (m, 7H), 3.37 (s, 3H), 2.34 (s, 3H). FABLRMS m/z 401 (M+Li). FABHRMS m/z 395.0675 (M$^+$H, Calc'd 395.0678). Anal. Calc'd for C$_{18}$H$_{15}$N$_2$O$_5$SNa. 3.66 H$_2$O: C, 46.96; H, 4.89, N, 6.09; Found: C, 46.91, H, 4.40, N, 6.00.

EXAMPLE 73

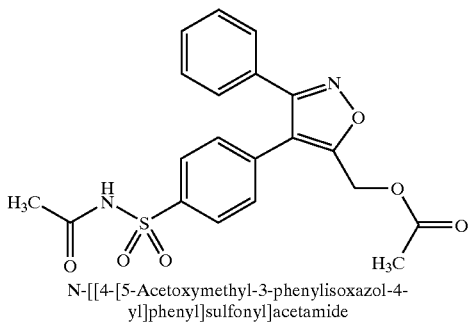

N-[[4-[5-Acetoxymethyl-3-phenylisoxazol-4-yl]phenyl]sulfonyl]acetamide

A suspension of 4-[5-hydroxymethyl-3-(phenyl)isoxazol-4-yl]benzenesulfonamide (1.51 g, 4.56 mmol) in 60 mL of dichloromethane was treated with acetic anhydride (1.30 mL, 1.40 g, 13.69 mmol), triethylamine (1.90 mL, 1.40 g, 13.70 mmol) and dimethylaminopyridine (0.056 g, 0.46 mmol). Within 5 minutes the mixture became homogeneous and stirring was continued for 40 hours. The reaction mixture was diluted with ethyl acetate and washed with 1N KHSO$_4$, brine, dried over MgSO$_4$, filtered and concentrated in vacuo to afford N-[[4-[5-acetoxymethyl-3-phenylisoxazol-4-yl]phenyl]sulfonyl]acetamide (1.67 g, 88%): mp 137–139° C. $^1$H NMR (CDCl$_3$/300 MHz) 8.58 (brs, 1H), 8.06 (d, 2H, J=8.47 Hz), 7.47–7.34 (m, 7H), 5.17 (s, 2H), 2.12 (s, 3H), 2.10 (s, 3H). FABLRMS m/z 421 (M+Li). FABHRMS m/z 415.0953 (M+H, C$_{20}$H$_{19}$N$_2$O$_6$S Calc'd 415.0964)

EXAMPLE 74

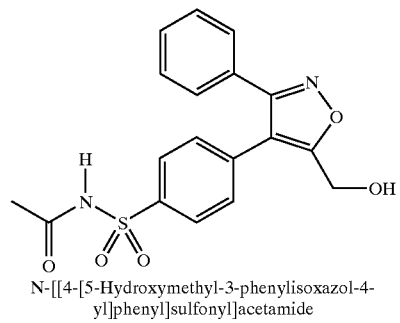

N-[[4-[5-Hydroxymethyl-3-phenylisoxazol-4-yl]phenyl]sulfonyl]acetamide

A solution of N-[[4-[5-acetoxymethyl-3-phenylisoxazol-4-yl]phenyl]sulfonyl]acetamide (Example 73) (0.867 g, 2.09 mmol) in methanol was treated with sodium hydroxide. The reaction was concentrated in vacuo, dissolved in water and slowly acidified with 1N HCl to yield a solid. The solid was dissolved in ethyl acetate, washed with brine, dried over MgSO$_4$, filtered and concentrated in vacuo to afford N-[[4-[5-hydroxymethyl-3-phenylisoxazol-4-yl]phenyl]sulfonyl]acetamide as a yellow foam, (0.513 g, 66%) of suitable purity for use without further purification: mp 94–103° C. $^1$H NMR (CDCl$_3$/300 MHz) 8.18 (brs, 1H), 7.09 (d, 2H, J=10.08 Hz), 7.47–7.35 (m, 7H), 4.78 (s, 2H), 2.23 (brs, 1H), 2.11 (s, 3H). FABLRMS m/z 373 (M+H). FABHRMS m/z 373.0876 (M+H, Calc'd 373.0858). Anal. Calc'd for C$_{18}$H$_{16}$N$_2$O$_5$S$_1$: C, 58.06; H, 4.33, N, 7.52. Found: C, 57.73, H, 4.70, N, 7.07.

EXAMPLE 75

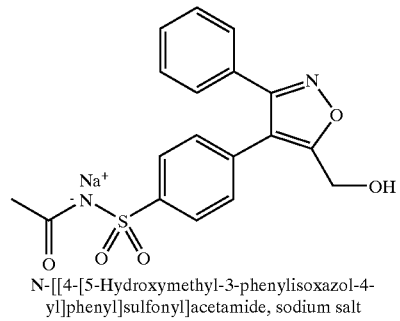

N-[[4-[5-Hydroxymethyl-3-phenylisoxazol-4-yl]phenyl]sulfonyl]acetamide, sodium salt A solution of N-[[4-[5-hydroxymethyl-3-phenylisoxaxzol-4-yl]phenyl]sulfonyl]acetamide (Example 74) (0.468 g, 1.26 mmol) in methanol was treated with NaOH solution (0.50 mL, 2.50N solution, 1.26 mmol). After 5 minutes, the solution was concentrated in vacuo to afford N-[[4-[5-hydroxymethyl-3-phenylisoxaxzol-4-yl]phenyl]sulfonyl]acetamide, sodium salt (0.462 g, 93%) as a tan foam: $^1$H NMR (D$_2$O/300 MHz) 7.68 (d, 2H, J=8.46 Hz), 7.39–7.23 (m, 7H), 4.60 (s, 2H), 1.79 (s, 3H). FABLRMS m/z 395 (M+Na).

EXAMPLE 76

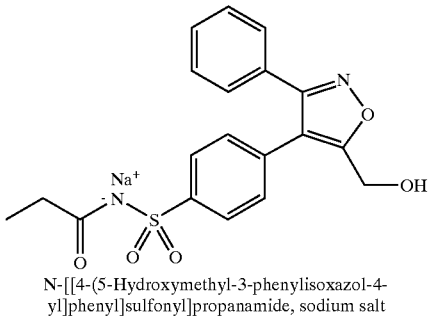

N-[[4-(5-Hydroxymethyl-3-phenylisoxazol-4-yl]phenyl]sulfonyl]propanamide, sodium salt Step 1: Preparation of N-[[4-(5-Propoxymethyl-3-phenylisoxazol-4-yl]phenyl]sulfonyl]propanamide A suspension of 4-[5-hydroxymethyl-3-(phenyl)isoxazol-4-yl]benzenesulfonamide (0.314 g, 0.947 mmol) in THF was treated with propionic anhydride (0.36 mL, 0.37 g, 2.846 mmol), triethylamine (0.40 mL, 0.29 g , 2.85 mmol),) and dimethylaminopyridine (0.025 g, 0.205 mmol). The resulting solution was stirred for 24 hours. The crude reaction was diluted with ethyl acetate and washed with KHSO$_4$, brine, dried over MgSO$_4$, filtered and concentrated in vacuo. The resulting product was purified by flash chromatography using as eluant hexane/ethyl acetate (1:1). Concentration of the appropriate fractions gave N-[[4-(5-propoxymethyl-3-phenylisoxazol-4-yl]phenyl]sulfonyl] propanamide (0.33 g, 79%) as a clear brown oil of suitable purity to use in the next step.

Step 2: Preparation of N-[[4-(5-Hydroxymethyl-3-phenylisoxazol-4-yl]phenyl]sulfonyl]propanamide The N-[[4-(5-propoxymethyl-3-phenylisoxazol-4-yl]phenyl]sulfonyl]propanamide (Step 1) was dissolved in methanol and NaOH solution (0.89 mL of 2.5 N, 2.24 mmol) added with stirring. After 12 hours, the reaction was acidified with 1 N HCl solution and extracted with a mixture of dichloromethane and ethyl acetate. The combined organic phases were dried over MgSO$_4$, filtered and concentrated in vacuo yielding N-[[4-(5-hydroxymethyl-3-phenylisoxazol-4-yl]phenyl]sulfonyl]propanamide (0.238 g, 83%) of sufficient purity to use in the next step.

Step 3: Preparation of N-[[4-(5-hydroxymethyl-3-phenylisoxazol-4-yl]phenyl]sulfonyl]propanamide, Sodium Salt N-[[4-(5-Hydroxymethyl-3-phenylisoxazol-4-yl]phenyl] sulfonyl]propanamide (Step 2) was dissolved in methanol and treated with NaOH solution (1.23 mL of 0.50 N, 0.62 mmol). The resulting solution was concentrated in vacuo. The resulting oil was diluted with water and concentrated on high vacuum yielding N-[[4-(5-hydroxymethyl-3-phenylisoxazol-4-yl]phenyl]sulfonyl]propanamide, sodium salt (0.195 mg, 64%) as a tan foam: mp 153.5–157.1° C. $^1$H NMR (D$_2$O/300 MHz) 7.68 (d, 2H, J=8.46 Hz), 7.39–7.15 (m, 7H), 4.59 (s, 2 H), 2.04 (q, 2H, J=7.66 Hz), 0.86 (t, 3H, J=7.66 Hz).

EXAMPLE 77

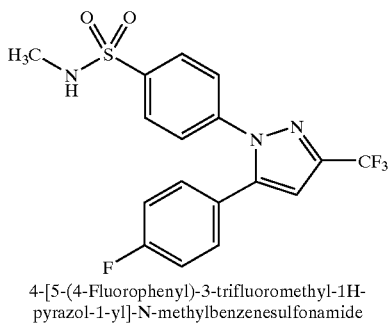

4-[5-(4-Fluorophenyl)-3-trifluoromethyl-1H-pyrazol-1-yl]-N-methylbenzenesulfonamide To a solution of 4-[5-(4-fluorophenyl)-3-trifluoromethyl-1H-pyrazol-1-yl]benzenesulfonamide (100 mg, 0.26 mmol) in DMSO (2 mL) was added sodium hydride (6 mg, 0.26 mmol). The reaction mixture was stirred at ambient temperature for 1.5 h. To this mixture was added methyl iodide (0.025 mL, 0.4 mmol). The mixture was stirred at room temperature for 16 h. The mixture was diluted with ethyl acetate (15 mL) and washed with water (3×10 mL). The organic solution was collected, dried (Na$_2$SO$_4$) and concentrated. The residue was chromatographed (3:1 hexane:ethyl acetate) to give the monomethyl sulfonamide (22 mg, 21%) as a gum. Exact mass Calc'd for C$_{17}$H$_{13}$F$_4$N$_3$O$_2$S: 399.0664. Found 399.0662.

EXAMPLE 78

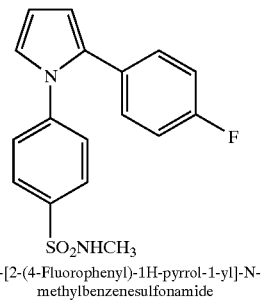

4-[2-(4-Fluorophenyl)-1H-pyrrol-1-yl]-N-methylbenzenesulfonamide

Step 1: Preparation of 5,5-Dimethyl-1,3-dioxane-2-proanol

The 5,5-dimethyl-1,3-dioxane-2-propanol was synthesized by following the literature procedure (J. Org. Chem. 57, 2195,1992).

Step 2: Preparation of 5,5-dimethyl-1,3-dioxane-2-propanal

DMSO (10.2 ml, 0.14 mol) was added to a solution of oxalyl chloride (5.5 ml, 63.2 mmol) in methylene chloride (25 ml) at −78° C. After stirring for 15 min, a solution of 5,5-dimethyl-1,3-dioxane-2-propanol (Step 1) (10 g, 57.5 mmol) in methylene chloride (100 ml) was added over 10 min. The reaction was stirred for 1 hr and triethylamine (40 ml, 0.2 mol) was added. After stirring at −70° C. for 1 hr, the reaction mixture was warmed to room temperature and stirred for 2 hr. The reaction was quenched with water and extracted with methylene chloride. The organic fractions were washed with aqueous sodium bicarbonate and brine. After drying (Na$_2$SO4), filtration and concentration, the crude compound was chromatographed (silica gel, hexane/ethyl acetate 7/3) to give 5,5-dimethyl-1,3-dioxane-2-propanal (6.1 g, 61%) as a colorless liquid: Anal Calc'd. for C$_9$H$_{16}$O$_3$ 0.2H$_2$O: C, 61.48; H, 9.40. Found: C, 61.46; H, 9.24.

Step 3: Preparation of C: α-(4-Fluorophenyl)-5,5-dimethyl-1,3-dioxane-2-propanol 4-Fluorophenyl magnesium bromide (8.7 ml, 2M solution in ether, 17.44 mmol) was added to a solution of 5,5-dimethyl-1,3-dioxane-2-propanal (2 g, 11.62 mmol) (Step 2) in THF (50 ml) at −70° C. After stirring at −70° C. for 2 hr, the reaction mixture was warmed to room temperature and stirred overnight. The reaction was quenched with water and extracted with ethyl acetate. The organic fractions were combined and washed successively with water and brine. After drying (MgSO$_4$), filtration and concentration, the crude compound (3.5 g) was chromatographed to give α-(4-fluorophenyl)-5,5-dimethyl-1,3-dioxane-2-propanol (2.73 g) as a white solid: mp (DSC) 84° C. Anal Calc'd. for $C_{15}H_{21}FO_3$: C, 67.14; H, 7.89. Found: C, 67.18; H, 7.98.

Step 4: Preparation of 3-(5,5-dimethyl-1,3-dioxan-2-yl)-1-(4-fluorophenyl)propan-1-one To a solution of α-(4-fluorophenyl)-5,5-dimethyl-1,3-dioxane-2-propanol (Step 3) (2.6 g, 10.7 mmol) in methylene chloride (100 ml), pyridinium chlorochromate (3.5 g, 16.05 mmol) was added. After stirring at room temperature for 3 hr, the reaction mixture was diluted with ether and filtered through a short silica gel column. The column was eluted with ether and the fractions containing 3-(5,5-dimethyl-1,3-dioxan-2-yl)-1-(4-fluorophenyl)propan-1-one were combined and concentrated (2.2 g, 85%): mp (DSC) 65° C. Anal Calc'd. for $C_{15}H_{19}FO_3$: C, 67.65; H, 7.19. Found: C, 67.21; H, 7.43.

Step 5: Preparation of N-methyl-4-nitrobenzenesulfonamide

To a suspension of 4-nitrobenzenesulfonyl chloride (5 g, 22.56 mmol) in ether (250 ml), methylamine (5 ml, 40% aq. solution, 56.4 mmol) was added, and the mixture was stirred at room temperature. After 16 hr, the reaction mixture was concentrated to remove the solvent and the residue was resuspended in methylene chloride. After washing with 2N HCl and brine, the organic fractions were dried (MgSO$_4$), filtered and concentrated to give N-methyl-4-nitrobenzenesulfonamide (4.8 g, 98%): mp (DSC) 109° C. Anal Calc'd. for $C_7H_8N_2O_4S$: C, 38.89; H, 3.73; N, 12.96. Found: C, 38.83; H, 3.72; N, 12.96.

Step 6: Preparation of 4-[(N-methylamino)sulfonyl]aniline

To a solution of N-methyl-4-nitrobenzenesulfonamide (Step 5) (4.8 g, 22.2 mmol) in methanol (100 ml) in a Parr bottle was added Raney-nickel in methanol. The reaction mixture was flushed with nitrogen and hydrogen several times and maintained under hydrogen at delivery pressure of 5 psi. After stirring at 25° C. for approximately 20 hr, the reaction was vented and purged with nitrogen. The contents of the reaction were filtered and concentrated to remove the solvent. The 4-[(N-methylamino)sulfonyl]aniline obtained as a white solid (4.1 g, 100%) was used in the next step without further purification: mp (DSC) 138° C. Anal Calc'd. for $C_7H_{10}N_2O_2S$ 0.25 $H_2O$: C, 44.08; H, 5.55; N, 14.69. Found: C, 43.83; H, 5.39; N, 14.81.

Step 7: Preparation of 4-[2-(4-Fluorophenyl)-1H-pyrrol-1-yl]-N-methylbenzenesulfonamide A mixture of 3-(5,5-dimethyl-1,3-dioxan-2-yl)-1-(4-fluorophenyl)propan-1-one (Step 4) (400 mg, 1.5 mmol), 4-[(N-methylamino)sulfonyl]aniline (Step 6) (308 mg, 1.65 mmol) and p-toluenesulfonic acid (40 mg) in toluene (80 ml) was heated to reflux for 48 hr. The reaction mixture was cooled, filtered and concentrated. The crude yellowish solid (760 mg) was chromatographed (silica gel, hexane/ethyl acetate 7/3) to give 4-[2-(4-fluorophenyl)-1H-pyrrol-1-yl]-N-methylbenzenesulfonamide (198 mg, 40%) as a white solid: mp (DSC) 174° C. Anal Calc'd. for $C_{17}H_{15}N_2FO_2S$ 0.25 $H_2O$: C, 60.97; H, 4.67; N, 8.37. Found: C, 60.86; H, 4.56; N, 8.01.

EXAMPLE 79

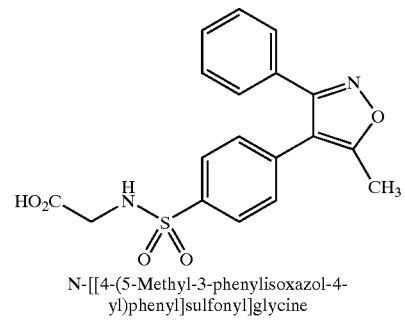

N-[[4-(5-Methyl-3-phenylisoxazol-4-yl)phenyl]sulfonyl]glycine

Step 1: Preparation of N-acetyl-N-[[4-(5-methyl-3-phenylisoxazol-4-yl)phenyl]sulfonyl]glycine, ethyl ester To a stirred solution of N-[[4-(5-methyl-3-phenylisoxazol-4-yl)phenyl]sulfonyl]acetamide (Example 39) (0.612 g, 1.72 mmol) in dichloromethane was treated with ethyl bromoacetate (0.20 mL, 0.29 g, 1.72 mmol) and Et$_3$N (0.26 mL, 0.19 g, 1.89 mmol). After 7 days the reaction was still incomplete by TLC. Additional ethyl bromoacetate (0.20 mL, 0.29 g, 1.72 mmol) and Et$_3$N (0.26 mL, 0.19 g, 1.89 mmol) were added and the reaction was stirred for an additional 6 days. The reaction was diluted with dichloromethane and washed with KHSO$_4$ solution, NaHCO$_3$ solution, and brine, dried over MgSO$_4$, filtered and concentrated in vacuo yielding a clear oil. This oil was purified by flash chromatography yielding N-acetyl-N-[[4-(5-methyl-3-phenylisoxazol-4-yl)phenyl]sulfonyl]glycine, ethyl ester (0.243 g, 32%) as a clear colorless oil of suitable purity for use in the next step: $^1$H NMR (CDCl$_3$/300 MHz) 8.03 (d, 2H, J=8.7 Hz), 7.47–7.27 (m, 9H), 4.61 (s, 2H), 4.21 (q, 2H, J=7.1 Hz), 2.51 (s, 3H), 2.33 (s, 3H), 1.28 (t, 3H, J=7.1 Hz). FABLRMS m/z 443 (M$^+$H). FABHRMS m/z 442.1201 (M$^+$, $C_{22}H_{22}N_2O_6S$ Calc'd 442.1199).

Step 2: Preparation of N-[[4-(5-methyl-3-phenylisoxazol-4-yl)phenyl]sulfonyl]glycine To a stirred solution of N-acetyl-N-[[4-(5-methyl-3-phenylisoxazol-4-yl)phenyl]sulfonyl]glycine, ethyl ester (Step 1) (0.24 g, 0.54 mmol) in methanol was added LiOH.H$_2$O (0.06 g, 1.36 mmol) in water. After 5 days the reaction was complete and the solvents were removed in vacuo. The resulting semi-solid was partitioned between ethyl acetate and 1N KHSO$_4$ solution. The ethyl acetate phase was dried over MgSO$_4$, filtered and concentrated in vacuo yielding N-[[4-(5-methyl-3-phenylisoxazol-4-yl)phenyl]sulfonyl]glycine (0.139 g, 69%) as a white powder: mp 242–248° C. $^1$H NMR (CDCl$_3$/300 MHz with DMSO-d$_6$) 7.76 (d, 2H, J=8.5 Hz), 7.33–7.22 (m, 5H), 7.19 (d, 2H, J=8.5 Hz), 6.35 (t, 1H, J=5.4 Hz), 3.63 (d, 2H, J=5.4 Hz), 2.39 (s, 3H). FABLRMS m/z 373 (M$^+$H). FABHRMS m/z 372.0786 (M+, Calc'd 372.0780). Anal. Calc'd for $C_{18}H_{16}N_2O_5S$: C, 58.06; H, 4.33; N, 7.52; Found C, 58.09; H, 4.44; N, 7.45.

EXAMPLE 80

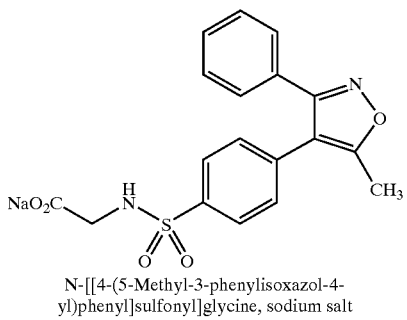

N-[[4-(5-Methyl-3-phenylisoxazol-4-yl)phenyl]sulfonyl]glycine, sodium salt

To a solution of N-[[4-(5-methyl-3-phenylisoxazol-4-yl)phenyl]sulfonyl]glycine (Example 79) (0.095 g, 0.255 mmol) in EtOH was added 0.5022N NaOH (0.58 mL, 0.29 mmol). The solution was concentrated in vacuo to afford the desired salt (0.100 g, 100%) as a white powder: mp 216° C. (dec). $^1$H NMR (D$_2$O/300 MHz) 7.66 (d, 2H, J=8.1 Hz), 7.42–7.15 (m, 7H), 3.36 (s, 2H), 2.32 (s, 3H). FABLRMS m/z 395 (M$^+$H). FABHRMS m/z 395.0707 (M$^+$H, Calc'd 395.0678). Anal. Calc'd for C$_{18}$H$_{15}$N$_2$O$_5$SNa.1.55 H$_2$O: C, 51.19; H, 4.32; N, 6.63. Found C, 51.18; H, 4.20; N, 6.56.

EXAMPLE 81

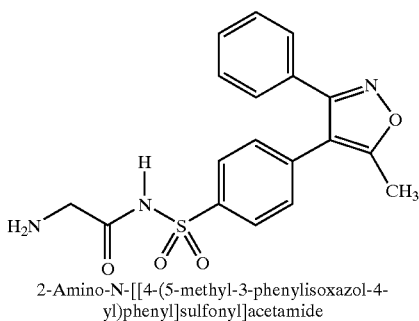

2-Amino-N-[[4-(5-methyl-3-phenylisoxazol-4-yl)phenyl]sulfonyl]acetamide

Step 1. Preparation of 1,1-Dimethylethyl N-[2-[[[4-(5-methyl-3-phenylisoxazol-4-yl)phenyl]sulfonyl]amino]-2-oxoethyl]carbamate A mixture of 4-[5-methyl-3-(phenyl)isoxazol-4-yl]benzenesulfonamide (15.0 g, 47.7 mmol), N-t-boc-glycine N-hydroxysuccinimide ester (13.0 g, 47.7 mmol) and 1,8-diazobicyclo[4.3.0]undec-7-ene (14.5 g, 95.4 mmol) were mixed together in tetrahydrofuran for 1 hour at room temperature. Additional N-t-boc-glycine N-hydroxysuccinimide ester (1.3 g, 4.7 mmol) was added and the solution was stirred an additional 2 hours. The solvent was removed at reduced pressure and residue was taken up in ethyl acetate. The ethyl acetate was washed with 10% aqueous HCl, sat. aq. NaHCO$_3$, dried over anhydrous Na$_2$SO$_4$, filtered and concentrated in vacuo to afford the desired amide as a clear glassy solid (6.5 g, 75%): mp 160.2–162.0° C. $^1$H NMR (CDCl$_3$/300 MHz) 8.04 (d, 2H, J=8.4 Hz), 7.44–7.33 (m, 5H), 7.28 (d, 2H, J=8.4 Hz), 5.24 (brs, 1H), 3.85 (m, 2H), 2.50 (s, 3H), 1.43 (s, 9H). FABLRMS m/z 472 (M+H). Anal. Calc'd for C$_{23}$H$_{25}$N$_3$O$_5$S.0.18 H$_2$O: C, 58.19; H, 5.38; N, 8.85. Found: C, 58.22; H, 5.73; N, 8.92.

Step 2. Preparation of 2-Amino-N-[[4-(5-methyl-3-phenylisoxazol-4-yl)phenyl]sulfonyl]acetamide The amide from Step 1 (16.2 g, 34.3 mmol) was dissolved in dichloromethane. Anhydrous HCl was bubbled through the solution for 30 minutes at room temperature. The solution was mixed for 1 hour and solvent was removed at reduced pressure. The resulting residue was dissolved in water and crystals began to form. The solution was stirred for 3 hours and crystals collected by vacuum filtration. The product, was dried to a constant weight under vacuum (25° C. at 15 mm Hg, 4 days) (9.4 g, 73%): mp 230.7–234.7° C. $^1$H NMR (DMSO-d$_6$/300 MHz) 7.84 (d, 2H, J=8.4 Hz), 7.70–7.60 (brs, 3H), 7.45–7.30 (m, 5H), 7.23 (d, 2H, J=8.4 Hz), 3.24 (m, 2H), 2.43 (s, 3H). FABLRMS m/z 372 (M+H). Anal. Calc'd for C$_{18}$H$_{17}$N$_3$O$_4$S.0.30 H$_2$O: C, 57.37; H, 4.71; N, 11.15. Found: C, 57.37; H, 4.70; N, 11.12.

EXAMPLE 82

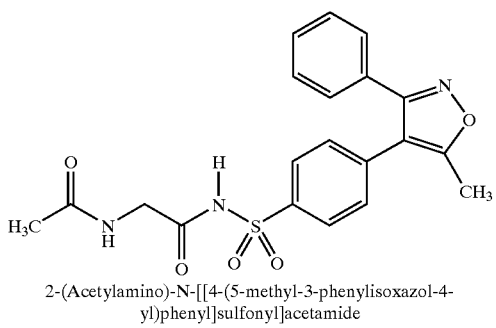

2-(Acetylamino)-N-[[4-(5-methyl-3-phenylisoxazol-4-yl)phenyl]sulfonyl]acetamide

The 2-amino-N-[[4-(5-methyl-3-phenylisoxazol-4-yl)phenyl]sulfonyl]acetamide (Example 81)(4.08 g, 10.9 mmol) was mixed in acetonitrile at room temperature. Triethylamine (3.03 g, 30.0 mmol) and acetic anhydride (1.23 g, 12.1 mmol) were added and the heterogeneous solution was stirred for 2 hours. The solution was vacuum filtered through a pad of diatomaceous earth and solvent was removed at reduced pressure. Water was added and the solution was stirred for 30 minutes. White crystals formed, were collected by vacuum filtration and dried to afford the desired product as a white solid (3.25 g, 78%): mp 218.2–219.3° C. $^1$H NMR (CD$_3$OD/300 MHz) 8.01 (d, 2H, J=8.2 Hz), 7.42–7.36 (m, 7H), 3.85 (s, 2H), 2.50 (s, 3H), 1.95 (s, 3H). FABLRMS m/z 414 (M+H). Anal. Calc'd for C$_{20}$H$_{19}$N$_3$O$_5$S: C, 58.10; H, 4.63; N,10.16. Found: C, 58.18; H, 4.66; N, 10.14.

EXAMPLE 83

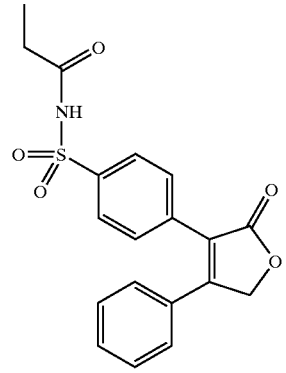

N-[[4-(3-Phenyl-2,3-dihydro-2-oxofuran-4-yl)phenyl]sulfonyl]propanamide

Step 1. Preparation of 3,4-Diphenyl-2-(5H)-furanone.

A solution of phenacyl bromide (16.540 g, 83.1 mmol) and phenylacetic acid (11.612 g, 85.3 mmol) in acetonitrile was treated with triethylamine (9.23 g, 91.4 mmol) and the solution was stirred at room temperature for 1 hour. The solution was treated with 1,8-diazabicyclo[5.4.0]undec-7-ene (DBU) (30 mL. 0.234 mol) and the solution was stirred at room temperature for 1 hour. The solution was diluted with 3 N HCl and extracted with ethyl acetate. The combined extract was washed with 3 N HCl, brine, dried over anhydrous $MgSO_4$, filtered and concentrated in vacuo to afford a solid. The solid was crystallized from hexanes/ethyl acetate 1:1 to afford the furanone (11.627 g, 59%): mp 103.8–104.9° C. $^1$H NMR ($CDCl_3$/300 MHz) 7.45–7.25 (m, 10H), 5.18 (s, 2H). FABLRMS m/z 237 (M+H). Anal. Calc'd for $C_{16}H_{13}O_2 \cdot 0.83\%$ $H_2O$: C, 80.66; H, 5.17. Found: C, 80.67; H, 5.29.

Step 2. Preparation of 3-[4-Aminosulfonyl)phenyl)]-4-phenyl-2-(5H)-furanone.

To 20 mL of stirring chlorosulfonic acid cooled to –5° C. was added 3,4-diphenyl-2-(5H)-furanone (Step 1)(3.160 g, 13.4 mmol) portion-wise over 30 minutes. The solution was warmed to room temperature and maintained at that temperature for 16 hours. The reaction mixture was diluted with dichloromethane and quenched into ice water. The phases were separated and the aqueous phase extracted with dichloromethane, the combined dichloromethane extract was dried over anhydrous $MgSO_4$, filtered and concentrated in vacuo. The residue was diluted with dichloromethane and added to excess concentrated $NH_4OH$. The mixture was stirred for 1 hour. The phases were separated and the aqueous phase was extracted with dichloromethane. The organic extract was dried over anhydrous $MgSO_4$, filtered and concentrated in vacuo to give a white solid that was crystallized from aqueous ethanol to afford pure 3-[(4-aminosulfonyl)phenyl)]-4-phenyl-2-(5H)-furanone (2.110 g, 50%): mp 225.5–226.5° C. $^1$H NMR ($CDCl_3$/300 MHz) 7.79 (d, 2H, J=8.4 Hz), 7.41 (d, 2H, J=8.4 Hz), 6.38 (brs, 2H), 5.09 (s, 2H). FABLRMS m/z 316 (m+H). Anal. Calc'd for $C_{16}H_{13}NO_4S$: C, 60.94; H, 4.16; N, 4.44. Found: C, 60.86; H, 4.18; N, 4.40.

Step 3. Preparation of N-[[4-(3-phenyl-2,3-dihydro-2-oxofuran-4-yl)pheny]sulfonyl]propanamide A solution of 3-[(4-aminosulfonyl)phenyl)]-4-phenyl-2-(5H)-furanone (Step 2)(209 mg, 0.663 mmol), triethylamine (134 mg, 1.33 mmol), N,N-dimethylaminopyridine (58 mg, 0.475 mmol) in THF was treated with propionic anhydride (129 mg, 0.994 mmol) at room temperature for 45 minutes. The solution was diluted with 3N HCl and extracted with ethyl acetate. The ethyl acetate solution was washed with brine, dried over anhydrous $MgSO_4$, filtered and concentrated to give an oil that was crystallized from ethyl acetate/hexanes to afford the acylated sulfonamide as a white solid (179 mg, 73%): mp 182.3–183.4° C. $^1$H NMR ($CDCl_3$/300 MHz) 8.56 (s, 1H), 8.06 (d, 2H, J=8.7 Hz), 7.62 (d, 2H, J=8.7 Hz), 7.44–7.22 (m, 5H), 5.23 (s, 2H), 2.30 (q, 2H, J=7.5 Hz), 1.08 (t, 3H, J=7.5 Hz). FABLRMS m/z 372 (M+H). Anal. Calc'd for $C_{19}H_{17}NO_5S$: C, 61.44; H, 4.61; N, 3.77. Found: C, 61.26; H, 4.64; N, 3.71.

EXAMPLE 84

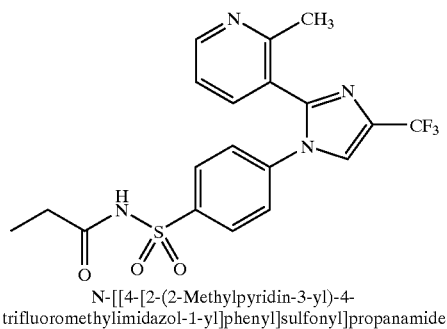

N-[[4-[2-(2-Methylpyridin-3-yl)-4-trifluoromethylimidazol-1-yl]phenyl]sulfonyl]propanamide A mixture of of 4-[2-(2-methylpyridin-3-yl)-4-(trifluoromethyl)-1H-imidazol-1-yl]benzenesulfonamide (2.0 g, 5.2 mmol), propionic anhydride (2.03 g, 15.6 3mmol), DMAP (0.38 g, 2.6 mmol) and triethylamine (0.65 g, 6.4 mmol) in 80 mL of THF was stirred at room temperature for 16 hours. The reaction mixture was diluted with 200 mL of water and extracted with ethyl acetate. The organic layer was washed with water, brine, dried over $MgSO_4$ and filtered. The filtrate was concentrated under vacuum and the residue was recrystallized from ethyl acetate and hexane to afford 1.95 g of the desired product as a colorless solid (87%): mp(DSC): 217–218° C. Anal. Calc'd for $C_{19}H_{17}F_3N_4O_3S$: C, 52.05; H, 3.91; N, 12.98; S, 7.31. Found: C, 51.87; H, 3.84; N, 12.67; S, 7.63.

EXAMPLE 85

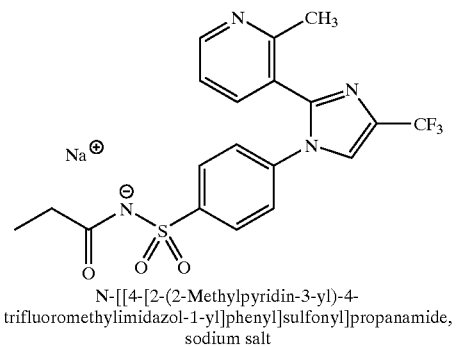

N-[[4-[2-(2-Methylpyridin-3-yl)-4-trifluoromethylimidazol-1-yl]phenyl]sulfonyl]propanamide, sodium salt To a suspension of N-[[4-[2-(2-methylpyridin-3-yl)-4-trifluoromethylimidazol-1-yl]phenyl]sulfonyl]propanamide (Example 84) (1.1 g, 2.5 mmol) in 20 mL of absolute ethanol was added a solution of sodium hydroxide (0.1 g, 2.5 mmol) in 1.0 mL of ethanol. The mixture was stirred at room temperature for 10 minutes. Solvent was evaporated in vacuo and the residue was dried at high vacuum to give 1.15 g of compound as a white powder (99%): mp(DSC): 298° C. (dec). Anal. Calc'd. for $C_{19}H_{17}F_3N_4O_3SNa \cdot 1.0$ H2O: C, 47.70; H, 3.79; N, 11.71; S, 6.70. Found: C, 47.37; H, 4.03; N, 11.32; S, 6.32.

EXAMPLE 87

A composition is prepared having the following components:

| | |
|---|---|
| N-[[4-(5-methyl-3-phenylisoxazol-4-yl)phenyl]sulfonyl]propanamide, sodium salt | 40 mg |
| phosphate buffer, pH 7.5 (10 mM) | 2 ml |
| mannitol | 40 mg |

Mannitol (40 mg) is added to phosphate buffer solution (2 ml). The N-[[4-(5-methyl-3-phenylisoxazol-4-yl)phenyl]sulfonyl]propanamide, sodium salt is added and the resulting solution is lyophilized.

BIOLOGICAL EVALUATION

Rat Carrageenan Foot Pad Edema Test

The carrageenan foot edema test was performed with materials, reagents and procedures essentially as described by Winter, et al., (*Proc. Soc. Exp. Biol. Med.*, 111, 544 (1962)). Male Sprague-Dawley rats were selected in each group so that the average body weight was as close as possible. Rats were fasted with free access to water for over sixteen hours prior to the test. The rats were dosed orally (1 mL) with compounds suspended in vehicle containing 0.5% methylcellulose and 0.025% surfactant, or with vehicle alone. One hour later a subplantar injection of 0.1 mL of 1% solution of carrageenan/sterile 0.9% saline was administered and the volume of the injected foot was measured with a displacement plethysmometer connected to a pressure transducer with a digital indicator. Three hours after the injection of the carrageenan, the volume of the foot was again measured. The average foot swelling in a group of drug-treated animals was compared with that of a group of placebo-treated animals and the percentage inhibition of edema was determined (Otterness and Bliven, *Laboratory Models for Testing NSAIDs*, in *Non-steroidal Anti-Inflammatory Drugs*, (J. Lombardino, ed. 1985)). The % inhibition shows the % decrease from control paw volume determined in this procedure and the data for selected compounds in this invention are summarized in Table I.

Rat Carrageenan-induced Analgesia Test

The rat carrageenan analgesia test was performed with materials, reagents and procedures essentially as described by Hargreaves, et al., (*Pain*, 32, 77 (1988)). Male Sprague-Dawley rats were treated as previously described for the Carrageenan Foot Pad Edema test. Three hours after the injection of the carrageenan, the rats were placed in a special plexiglass container with a transparent floor having a high intensity lamp as a radiant heat source, positionable under the floor. After an initial twenty minute period, thermal stimulation was begun on either the injected foot or on the contralateral uninjected foot. A photoelectric cell turned off the lamp and timer when light was interrupted by paw withdrawal. The time until the rat withdraws its foot was then measured. The withdrawal latency in seconds was determined for the control and drug-treated groups, and percent inhibition of the hyperalgesic foot withdrawal determined. Results are shown in Table I.

TABLE I

| | RAT PAW EDEMA | ANALGESIA |
|---|---|---|
| | % Inhibition | % Inhibition |
| Example | @ 30 mg/kg body weight | @ 10 mg/kg body weight |
| 13 | 58 | 61.5 |
| 14 | 65 | 41 |
| 25 | 60 | 33 |

In Vitro Conversion of Prodrugs

The conversion of the prodrugs by S9 liver fractions was determined by the following method. The S9 liver fraction suspension (IIAM) was thawed and the suspension was stirred by vortex. The suspension was mixed with 12M urea at 1:7, v:v, (yielding 10.5 M urea final concentration) and further stirred by vortex. The S9 suspension solution was partially purified by solid phase extraction (Vac-Elut apparatus:$C_{18}$ columns (Varian #1210–2001)) eluting with acetonitrile. The fractions were mixed by vortex and concentrated to dryness under nitrogen (no heat). The fractions were resuspended in 100 µl acetonitrile:phosphate buffer (8.3 mM, pH 7.2) (20:80).

The compounds were dissolved in water (0.2 ml, 10 µg/ml) and incubated at 37° C. (pH 7.2, 90 minutes) with purified S9 fractions (0.2 ml, 3 mg/ml). Conversion of the prodrug to the active COX-2 inhibitor was followed by HPLC (Beckmann System Gold, Novapak $C_{18}$ column (3.9×150 mm), acetonitrile:phosphate buffer (8.3 mM, pH 7.2) (20:80–40:60), UV detection 240 nm). Quantitation of the conversion of the prodrug was determined by measurement of integrated HPLC peak area. The results of the analysis are included in Table II:

TABLE II

| Metabolism of Prodrugs | |
|---|---|
| Example | Parent (% remaining) |
| 14 | 63.4 |
| 18 | 3.3 |
| 25 | 0.8 |

Also embraced within this invention is a class of pharmaceutical compositions comprising the active compounds of this combination therapy in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The active compounds and composition may, for example, be administered orally, intravascularly (IV), intraperitoneally, subcutaneously, intramuscularly (IM) or topically.

For oral administration, the pharmaceutical composition may be in the form of, for example, a tablet, hard or soft capsule, lozenges, dispensable powders, suspension or liquid. The pharmaceutical composition is preferably made in the form of a dosage unit containing a particular amount of the active ingredient. Examples of such dosage units are tablets or capsules.

The active ingredient may also be administered by injection (IV, IM, subcutaneous or jet) as a composition wherein, for example, saline, dextrose, or water may be used as a suitable carrier. The pH of the composition may be adjusted, if necessary, with suitable acid, base, or buffer. Suitable bulking, dispersing, wetting or suspending agents, including mannitol and PEG 400, may also be included in the composition. A suitable parenteral composition can also include a compound formulated as a sterile solid substance, including lyophilized powder, in injection vials. Aqueous solution can be added to dissolve the compound prior to injection.

The amount of therapeutically active compounds that are administered and the dosage regimen for treating a disease condition with the compounds and/or compositions of this invention depends on a variety of factors, including the age, weight, sex and medical condition of the subject, the severity of the inflammation or inflammation related disorder, the route and frequency of administration, and the particular compound employed, and thus may vary widely. The prodrug compositions should include similar dosages as for the parent compounds. The pharmaceutical compositions may contain active ingredients in the range of about 0.1 to 1000 mg, preferably in the range of about 0.5 to 250 mg and most preferably between about 1 and 60 mg. A daily dose of about 0.01 to 100 mg/kg body weight, preferably between about 0.05 and about 20 mg/kg body weight and most preferably between about 0.1 to 10 mg/kg body weight, may be appropriate. The daily dose can be administered in one to four doses per day.

In the case of skin conditions, it may be preferable to apply a topical preparation of compounds of this invention to the affected area two to four times a day.

For disorders of the eye or other external tissues, e.g., mouth and skin, the formulations are preferably applied as a topical gel, spray, ointment or cream, or as a suppository, containing the active ingredients in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs. The compounds of this invention can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane. The transdermal patch may include the compound in a suitable solvent system with an adhesive system, such as an acrylic emulsion, and a polyester patch.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, and sodium lauryl sulfate, among others.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or-other mineral oils can be used.

Formulations suitable for topical administration to the eye also include eye drops wherein the active ingredients are dissolved or suspended in suitable carrier, especially an aqueous solvent for the active ingredients. The antiinflammatory active ingredients are preferably present in such formulations in a concentration of 0.5 to 20%, advantageously 0.5 to 10% and particularly about 1.5% w/w.

For therapeutic purposes, the active compounds of this combination invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art. Although this invention has been described with respect to specific embodiments, the details of these embodiments are not to be construed as limitations.

What is claimed is:
1. A compound of Formula I

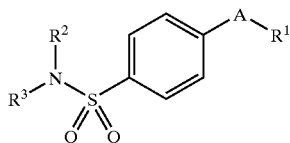

wherein A is a ring substituent selected from partially unsaturated heterocyclic, heteroaryl, cycloalkenyl and aryl, wherein A is unsubstituted or substituted with one or more radicals selected from alkylcarbonyl, formyl, halo, alkyl, haloalkyl, oxo, cyano, nitro, carboxyl, alkoxy, aminocarbonyl, alkoxycarbonyl, carboxyalkyl, cyanoalkyl, hydroxyalkyl, haloalkylsulfonyloxy, alkoxyalkyloxyalkyl, carboxyalkoxyalkyl, cycloalkylalkyl, alkenyl, alkynyl, heterocycloxy, alkylthio, cycloalkyl, aryl, heterocyclyl, cycloalkenyl, aralkyl, heterocyclylalkyl, alkylthioalkyl, arylcarbonyl, aralkylcarbonyl, aralkenyl, alkoxyalkyl, arylthioalkyl, aryloxyalkyl, aralkylthioalkyl, araalkoxyalkyl, alkoxycarbonylalkyl, aminocarbonylalkyl, alkylaminocarbonyl, N-arylaminocarbonyl, N-alkyl-N-arylaminocarbonyl, alkylaminocarbonylalkyl, alkylamino, -arylamino, N-aralkylamino, N-alkyl-N-aralkylamino, N-alkyl-N-arylamino, aminoalkyl, alkylaminoalkyl, N-arylaminoalkyl, N-aralkylaminoalkyl, N-alkyl-N-arylaminoalkyl, aryloxy, aralkoxy, arylthio, aralkylthio, alkylsulfinyl, alkylsulfonyl, aminosulfonyl, alkylaminosulfonyl, N-arylaminosulfonyl, arylsulfonyl, and N-alkyl-N-arylaminosulfonyl;

wherein $R^1$ is selected from heterocyclyl, cycloalkyl, cycloalkenyl, and aryl, wherein $R^1$ is unsubstituted or substituted with one or more radicals selected from alkyl, haloalkyl, cyano, carboxyl, alkoxycarbonyl, hydroxyl, hydroxyalkyl, haloalkoxy, amino, alkylamino, arylamino, nitro, alkoxyalkyl, alkylsulfinyl, halo, alkoxy, and alkylthio;

wherein $R^2$ is selected from hydrido and alkoxycarbonylalkyl; and wherein $R^3$ is selected from alkyl, carboxyalkyl, acyl, alkoxycarbonyl, heteroarylcarbonyl, alkoxycarbonylalkylcarbonyl, alkoxycarbonylcarbonyl, amino acid residue, and alkylcarbonylaminoalkylcarbonyl;

provided A is not tetrazolium, or pyridinium; and further provided A is not indanone when $R^3$ is alkyl or carboxyalkyl; further provided A is not thienyl, when $R^1$ is 4-fluorophenyl, when $R^2$ is hydrido, and when $R^3$ is methyl or acyl;

or a pharmaceutically-acceptable salt thereof.

2. A compound of claim 1 wherein A is selected from partially unsaturated heterocyclyl, 5- or 6-membered heteroaryl, $C_3$–$C_8$-cycloalkenyl and phenyl, wherein A is unsubstituted or substituted with one or more radicals selected from formyl, $C_1$–$C_{10}$-alkylcarbonyl, halo, $C_1$–$C_{10}$-alkyl, $C_1$–$C_6$-haloalkyl, oxo, cyano, nitro, carboxyl, $C_1$–$C_6$-alkoxy, aminocarbonyl, $C_1$–$C_6$-alkoxycarbonyl, $C_1$–$C_{10}$-carboxyalkyl, $C_1$–$C_{10}$-cyanoalkyl, $C_1$–$C_6$-hydroxyalkyl, $C_1$–$C_6$-haloalkylsulfonyloxy, $C_1$–$C_{10}$-alkoxyalkyloxyalkyl, carboxy-$C_1$–$C_{10}$-alkoxyalkyl, $C_3$–$C_8$-cycloalkylalkyl, $C_2$–$C_6$-alkenyl, $C_2$–$C_6$-alkynyl, heterocyclyloxy, $C_1$–$C_6$-alkylthio, $C_3$–$C_8$-cycloalkyl, phenyl, 5–6 membered heterocyclyl, $C_4$–$C_8$-cycloalkenyl, phenyl-$C_1$–$C_{10}$-alkyl, 5–6 membered ring heterocyclylalkyl, $C_1$–$C_6$-alkylthioalkyl, phenylcarbonyl, phenyl-$C_1$–$C_{10}$-alkylcarbonyl, phenyl-$C_2$–$C_6$-alkenyl, $C_1$–$C_{10}$-alkoxyalkyl, phenylthio-$C_1$–$C_{10}$-alkyl, phenyloxy-$C_1$–$C_{10}$-alkyl, phenyl-$C_1$–$C_6$-alkylthioalkyl, phenyl-$C_1$–$C_6$-alkoxyalkyl, $C_1$–$C_6$-alkoxycarbonylalkyl, aminocarbonyl-$C_1$–$C_{10}$-alkyl, $C_1$–$C_6$-alkylaminocarbonyl, N-phenylaminocarbonyl, N-$C_1$–$C_6$-alkyl-N-phenylaminocarbonyl, $C_1$–$C_6$-alkylaminocarbonylalkyl, $C_1$–$C_6$-alkylamino, N-phenylamino, N-phenyl-$C_1$–$C_6$-alkylamino, N-$C_1$–$C_6$-alkyl-N-phenylalkylamino, N-$C_1$–$C_6$-alkyl-N-phenylamino, $C_1$–$C_{10}$-aminoalkyl, $C_1$–$C_6$-alkylaminoalkyl, N-phenylarnino-$C_1$–$C_{10}$-alkyl, N-phenyl-$C_1$–$C_6$-alkylaminoalkyl, N-$C_1$–$C_6$-alkyl-N-phenylalkylaminoalkyl, N-$C_1$–$C_6$-alkyl-N-phenylaminoalkyl, phenyloxy, phenyl-$C_1$–$C_6$-alkoxy, phenylthio, phenyl-$C_1$–$C_{10}$-alkylthio, $C_1$–$C_6$-alkylsulfinyl, $C_1$–$C_6$-alkylsulfonyl, aminosulfonyl, $C_1$–$C_6$-alkylaminosulfonyl, N-phenylaminosulfonyl, phenylsulfonyl, and N-$C_1$–$C_6$-alkyl-N-phenylaminosulfonyl; wherein $R^1$ is selected from 5- or 6-membered heterocyclyl, $C_3$–$C_8$-cycloalkyl, $C_4$–$C_8$-cycloalkenyl and phenyl, wherein $R^1$ is unsubstituted or substituted with one or more radicals selected from $C_1$–$C_{10}$-alkyl, $C_1$–$C_6$-haloalkyl, cyano, carboxyl, $C_1$–$C_6$-alkoxycarbonyl, hydroxyl, $C_1$–$C_6$-hydroxyalkyl, $C_1$–$C_6$-haloalkoxy, amino, $C_1$–$C_6$-alkylamino, phenylamino, nitro, $C_1$–$C_{10}$-alkoxyalkyl, $C_1$–$C_6$-alkylsulfinyl, halo, $C_1$–$C_6$-alkoxy and $C_1$–$C_6$-alkylthio; wherein $R^2$ is selected from hydrido and $C_1$–$C_6$-alkoxycarbonylalkyl; and wherein $R^3$ is selected from $C_1$–$C_{10}$-alkyl, carboxy-$C_1$–$C_{10}$-alkyl, alkanoyl, aroyl, amino acid residue, $C_1$–$C_6$-alkoxycarbonyl, $C_1$–$C_{10}$-alkoxyalkylcarbonyl, (5–6-membered heteroaryl) carbonyl, $C_1$–$C_6$-alkoxycarbonylalkylcarbonyl, $C_1$–$C_6$-alkoxycarbonylcarbonyl, and -$C_1$–$C_{10}$-alkylcarbonylaminoalkylcarbonyl; or a pharmaceutically-acceptable salt thereof.

3. Compound of claim 2 wherein A is a radical selected from thienyl, oxazolyl, furyl, pyrrolyl, thiazolyl, imidazolyl, benzofuryl, indenyl, benzothienyl, isoxazolyl, pyrazolyl, cyclopentenyl, cyclopentadienyl, benzindazolyl, benzopyranopyrazolyl, phenyl and pyridyl, wherein A is unsubstituted or substituted with one or more radicals selected from formyl, methylcarbonyl, fluoro, chloro, bromo, methyl, trifluoromethyl, difluoromethyl, oxo, cyano, carboxyl, methoxy, aminocarbonyl, methoxycarbonyl, ethoxycarbonyl, carboxypropyl, hydroxymethyl, cyanomethyl, phenyl, phenylnethyl, methoxycarbonyl, phenylcarbonyl, methoxymethyl, phenyloxymethyl, aminocarbonylmethyl, carboxymethyl, and phenyloxy; wherein $R^1$ is selected from thienyl, oxazolyl, isoxazolyl, furyl, thiazolyl, pyridyl, and phenyl, where $R^1$ is unsubstituted or substituted with one or more radicals selected from methyl, trifluoromethyl, hydroxyl, hydroxymethyl, trifluoromethoxy, nitro, methoxymethyl, fluoro, chloro, bromo, methoxy and methylthio; wherein $R^2$ is hydrido, or ethoxycarbonylmethyl; and wherein $R^3$ is selected from methyl, carboxymethyl, formyl, methylcarbonyl, ethylcarbonyl, propylcarbonyl, isopropylcarbonyl, butylcarbonyl, tert-butylcarbonyl, pentylcarbonyl, benzylcarbonyl, phenyl(hydroxyl)methylcarbonyl, methoxycarbonyl, tert-butoxycarbonyl, phenylcarbonyl, methoxycarbonylmethylcarbonyl, methoxycarbonylethylcarbonyl, methoxycarbonylcarbonyl, aminomethylcarbonyl, tert-butoxycarbonylaminomethylcarbonyl, and methylcarbonylaminomethylcarbonyl; or a pharmaceutically acceptable salt thereof.

4. Compound of claim 3 selected from the group consisting of

N-[[4-[3-(difluoromethyl)-5-(3-fluoro-4-methoxyphenyl)-1H-pyrazol-1-yl]phenyl]sulfonyl]propanamide;

N-[[4-[3-(difluoromethyl)-5-(3-fluoro-4-methoxyphenyl)-1H-pyrazol-1-yl]phenyl]sulfonyl]butanamide;

N-[[4-[1,5-dimethyl)-3-phenyl-1H-pyrazol-4-yl]phenyl]sulfonyl]acetamide;

N-[[4-(2-(3-pyridinyl)-4-(trifluoromethyl)-1H-imidazol-1-yl)phenyl]sulfonyl]acetamide;

N-[[4-[2-(5-methylpyridin-3-yl)-4-(trifluoromethyl)-1H-imidazol-1-yl]phenyl]sulfonyl]acetamide;

N-[[4-[2-(2-methylpyridin-3-yl)-4-(trifluoromethyl)-1H-imidazol-1-yl]phenyl]sulfonyl]acetamide;

N-[[4-[2-(5-methylpyridin-3-yl)-4-(trifluoromethyl)-1H-imidazol-1-yl]phenyl]sulfonyl]butanamide;

N-[[4-[2-(2-methylpyridin-3-yl)-4-(trifluoromethyl)-1H-imidazol-1-yl]phenyl]sulfonyl]butanamide;

N-[[4-[2-(3-chloro-5-methylphenyl)-4-(trifluoromethyl)-1H-imidazol-1-yl]phenyl]sulfonyl]acetamide;

N-[[4-[3-(3-fluorophenyl)-5-methylisoxazol-4-yl]phenyl]sulfonyl]acetamide;

2-methyl-N-[[4-(5-methyl-3-phenylisoxazol-4-yl)phenyl]sulfonyl]propanamide;

N-[[4-(5-methyl-3-phenylisoxazol-4-yl)phenyl]sulfonyl]propanamide;

N-[[4-(5-methyl-3-phenylisoxazol-4-yl)phenyl]sulfonyl]benzamide;

2,2-dimethyl-N-[[4-(5-methyl-3-phenylisoxazol-4-yl)phenyl]sulfonyl]propanamide;

N-[[4-5-methyl-3-phenylisoxazol-4-yl)phenyl]sulfonyl]butanamide;

N-[[4-(5-methyl-3-phenylisoxazol-4-yl)phenyl]sulfonyl]pentanamide;

N-[[4-(5-methyl-3-phenylisoxazol-4-yl)phenyl]sulfonyl]hexanamide;

3-methoxy-N-[[4-(5-methyl-3-phenylisoxazol-4-yl)phenyl]sulfonyl]propanamide;

2-ethoxy-N-[[4-(5-methyl-3-phenylisoxazol-4-yl)phenyl]sulfonyl]acetamide;

N-[[4-[5-methyl-3-phenylisoxazol-4-yl]phenyl]sulfonyl]acetamide;

N-[[4-[5-(4-chlorophenyl)-3-(trifluoromethyl)-1H pyrazol-1-yl]phenyl]sulfonyl]propanamide;

N-[[4-[5-(4-chlorophenyl)-3-(trifluoromethyl)-1H-pyrazol-1-yl]phenyl]sulfonyl]butanamide;

N-[[4-[5-(4-chlorophenyl)-3-(trifluoromethyl)-1H-pyrazol-1-yl]phenyl]sulfonyl]acetamide;

N-[[4-[3-(difluoromethyl)-6-fluoro-1,5-dihydro-7-methoxy-[2]benzothiopyrano[4,3-c]pyrazol-1-yl)phenyl]sulfonyl]acetamide;

N-[[4-[6-fluoro-1,5-dihydro-7-methoxy-3-(trifluoromethyl)-[2]benzothiopyrano[4,3-c]pyrazol-1-yl]phenyl]sulfonyl]acetamide;

N-[[4-[3-(difluoromethyl)-5-(3-fluoro-4-methoxyphenyl)-1H-pyrazol-1-yl]phenyl]sulfonyl]acetamide;

N-[[4-(2-methyl-4-phenyloxazol-5-yl)phenyl]sulfonyl]acetamide;

methyl[[[4-(5-methyl-3-phenylisoxazol-4-yl)phenyl]sulfonyl]amino]oxoacetate;

2-methoxy-N-[[4-(5-methyl-3-phenylisoxazol-4-yl)phenyl]sulfonyl]acetamide;

N-[[4-[5-(difluoromethyl)-3-phenylisoxazol-4-yl]phenyl]sulfonyl]propanamide;

N-[[4-[5-(difluoromethyl)-3-phenylisoxazol-4-yl]phenyl]sulfonyl]butanamide;

N-[[4-(5-methyl-3-phenylisoxazol-4-yl)phenyl]sulfonyl]formamide;

1,1-dimethylethyl-N-[[4-(5-methyl-3-phenylisoxazol-4-yl)phenyl]sulfonyl]carbamate;

N-[[$^4$-(5-methyl-3-phenylisoxazol-4-yl)phenyl]sulfonyl]glycine;

2-amino-N-[[4-(5-methyl-3-phenylisoxazol-4-yl)phenyl]sulfonyl]acetamide;

2-(acetylamino)-N-[[4-(5-methyl-3-phenylisoxazol-4-yl)phenyl]sulfonyl]acetamide;

methyl 4-[[[4-(5-methyl-3-phenylisoxazol-4-yl)phenyl]sulfonyl]amino]-4-oxobutanoate;

methyl N-[[4-(5-methyl-3-phenylisoxazol-4-yl)phenyl]sulfonyl]carbamate;

N-acetyl-N-[[4-(5-methyl-3-phenylisoxazol-4-yl)phenyl]sulfonyl]glycine, ethyl ester;

N-[[4-(5-(4-methylphenyl)-3-(trifluoromethyl)-1H-pyrazol-1-yl)phenyl]sulfonyl]acetamide;

methyl 3-[[[4-(5-methyl-3-phenylisoxazol-4-yl)phenyl]sulfonyl]amino]-3-oxopropanoate;

4-[5-(3-bromo-5-fluoro-4-methoxyphenyl)-2-(trifluoromethyl)oxazol-4-yl]-N-methylbenezenesulfonamide;

N-(1,1-dimethylethyl)-4-(5-methyl-3-phenylisoxazol-4-yl)benzenesulfonamide;

4-[5-(4-fluorophenyl)-3-(trifluoromethyl)-1H-pyrazol-1-yl]-N-methylbenzenesulfonamide;

N-methyl-4-(5-methyl-3-phenylisoxazol-4-yl)benezenesulfonamide;

N-[[4-[5-(hydroxymethyl)-3-phenylisoxazol-4-yl]phenyl]sulfonyl]acetamide:

N-[[4-[5-(acetoxymethyl)-3-phenylisoxazol-4-yl]phenyl]sulfonyl]acetamide;

N-[[4-[2-(3-chloro-4-fluorophenyl)cyclopenten-1-yl)phenyl]sulfonyl]acetamide;

4-[2-(4-fluorophenyl)-1H-pyrrol-1-yl]-N-methylbenzenesulfonamide;

N-[[4-(3,4-dimethyl-1-phenyl-1H-pyrazol-5-yl]phenyl]sulfonyl]propanamide;

N-[[4-[2-(2-methylpyridin-3-yl)-4-trifluoromethylimidazol-1-yl]phenyl]sulfonyl]propanamide;

4-[2-(4-fluorophenyl)cyclopenten-1-yl]-N-methylbenzenesulfonamide; and

N-[[4-(3-phenyl-2,3-dihydro-2-oxofuran-4-yl)phenyl]sulfonyl]propanamide.

5. A compound of Formula II

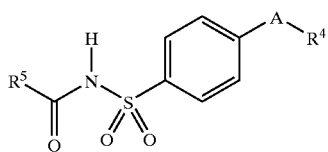

II wherein A is a ring substituent selected from partially unsaturated heterocyclyl, 5- or 6-membered heteroaryl, $C_4$–$C_8$-cycloalkenyl and phenyl; wherein A is unsubstituted or substituted with one or more radicals selected from acyl, halo, hydroxy, $C_1$–$C_{10}$-alkyl, $C_1$–$C_6$-haloalkyl, oxo, cyano, nitro, carboxyl, $C_1$–$C_6$-alkoxy, aminocarbonyl, $C_1$–$C_6$-alkoxycarbonyl, carboxy-$C_1$–$C_{10}$-alkyl, $C_1$–$C_{10}$-cyanoalkyl, $C_1$–$C_6$-hydroxyalkyl, $C_1$–$C_{10}$-alkylcarbonyloxyalkyl, and phenyl;

wherein $R^4$ is selected from heterocyclyl, cycloalkyl, cycloalkenyl and phenyl, wherein $R^4$ is unsubstituted or substituted with one or more radicals selected from $C_1$–$C_{10}$-alkyl, $C_1$–$C_6$-haloalkyl, cyano, carboxyl, $C_1$–$C_6$-alkoxycarbonyl, hydroxyl, $C_1$–$C_6$-hydroxyalkyl, $C_1$–$C_6$-haloalkoxy, amino, $C_1$–$C_6$-alkylamino, phenylamino, nitro, $C_1$–$C_{10}$-alkoxyalkyl, $C_1$–$C_6$-alkylsulfumyl, halo, $C_1$–$C_6$-alkoxy and $C_1$–$C_6$-alkylthio; and wherein $R^5$ is selected from hydrido, $C_1$–$C_{10}$-alkyl, $C_1$–$C_{10}$-alkoxy, $C_1$–$C_{10}$-alkoxyalkyl, phenyl, aryl-$C_1$–$C_{10}$-alkyl, carboxy-$C_1$–$C_{10}$-alkyl, $C_1$–$C_6$-alkoxycarbonylalkyl, $C_1$–$C_6$-alkoxycarbonyl, amino-$C_1$–$C_{10}$-alkyl, $C_1$–$C_6$-alkoxycarbonylaminoalkyl, and $C_1$–$C_{10}$-alkylcarbonylaminoalkyl; provided A is not tetrazolium or pyridinium; further provided A is not thienyl when $R^4$ is 4-fluorophenyl and when $R^5$ is methyl:

or a pharmaceutically-acceptable salt thereof.

6. Compound of claim 5 wherein A is a ring substituent selected from thienyl, oxazolyl, furyl, pyrrolyl, thiazolyl, imidazolyl, benzofuryl, indenyl, benzothienyl, isoxazolyl, pyrazolyl, cyclopentenyl, cyclopentadienyl, benzindazolyl, benzopyranopyrazolyl, phenyl, and pyridyl, wherein A is unsubstituted or substituted with one or more radicals selected from acyl, $C_1$–$C_{10}$-alkyl, $C_1$–$C_6$-haloalkyl, oxo, cyano, nitro, carboxyl, $C_1$–$C_6$-alkoxy, aminocarbonyl, $C_1$–$C_6$-alkoxycarbonyl, carboxy-$C_1$–$C_{10}$-alkyl, $C_1$–$C_{10}$-cyanoalkyl, $C_1$–$C_{10}$-alkylcarbonyloxyalkyl, phenyl and $C_1$–$C_6$-hydroxyalkyl;

wherein $R^4$ is selected from 5–6 membered heteroary and phenyl, wherein $R^4$ is unsubstituted or substituted with one or more radicals selected from $C_1$–$C_{10}$-alkyl, $C_1$–$C_{10}$-haloalkyl, cyano, carbonyl, $C_1$–$C_6$-alkoxycarbonyl, hydroxyl, $C_1$–$C_6$-hydroxyalkyl, $C_1$–$C_6$-haloalkoxy, amino, $C_1$–$C_6$-alkylamino, phenylamino, nitro, $C_1$–$C_{10}$-alkoxyalkyl, $C_1$–$C_6$-alkylsulfinyl, halo, $C_1$–$C_6$-alkoxy and $C_1$–$C_6$-alkylthio; and wherein $R^5$ is selected from hydrido, $C_1$–$C_{10}$-alkyl, $C_1$–$C_6$-alkoxy, $C_1$–$C_{10}$-alkoxyalkyl, phenyl, $C_1$–$C_6$-alkoxycarbonylalkyl, $C_1$–$C_6$-alkoxycarbonyl, amino-$C_1$–$C_{10}$-alkyl, $C_1$–$C_6$-alkoxycarbonylaminoalkyl, and $C_1$–$C_{10}$-alkylcarbonylaminoalkyl;

or a pharmaceutically-acceptable salt thereof.

7. Compound of claim 5 wherein A is a ring substituent selected from thienyl, oxazolyl, furyl, pyrrolyl, thiazolyl, imidazolyl, isothiazolyl, isoxazolyl, pyrazolyl, cyclopentenyl, cyclopentadienyl, benzindazolyl, benzopyranopyrazolyl, phenyl, and pyridyl; wherein A is unsubstituted or substituted with one or more radicals selected from formyl, fluoro, chloro, bromo, methyl, trifluoromethyl, oxo, cyano, carboxyl, methoxy, aminocarbonyl, methoxycarbonyl, ethoxycarbonyl, carboxymethyl, carboxypropyl methylcarbonyloxymethyl, and hydroxymethyl;

wherein $R^4$ is selected from thienyl, pyridyl and phenyl, wherein $R^4$ is unsubstituted or substituted with one or more radicals selected from methyl, trifluoromethyl, hydroxyl, hydroxymethyl, trifluoromethoxy, nitro, methoxymethyl, fluoro, chloro, bromo, methoxy and methoxythio; and wherein $R^5$ is selected from hydrido, methyl, ethyl, isopropyl, propyl, tert-butyl, butyl, pentyl, methoxy, tert-butoxy, methoxyethyl, ethoxymethyl, methoxymethyl, phenyl, carboxyethyl, methoxycarbonylmethyl, methoxycarbonylethyl, tert-butoxycarbonylaminomethyl, methoxycarbonyl, aminomethyl, and methylcarbonylaminomethyl;

or a pharmaceutically-acceptable salt thereof.

8. Compound of claim 7 selected from the group consisting of

N-[[4-[3-(difluoromethyl)-5-(3-fluoro-4-methoxyphenyl)-1H-pyrazol-1-yl]phenyl]sulfonyl] propanamide;

N-[[4-[3-(difluoromethyl)-5-(3-fluoro-4-methoxyphenyl)-1H-pyrazol-1yl]phenyl]sulfonyl] butanamide;

N-[[4-[1,5-dimethyl)-3-phenyl-1H-pyrazol-4-yl]phenyl] sulfonyl]acetamide;

N-[[4-[2-3-pyridinyl)-4-(trifluoromethyl)-1H-imdazol-1-yl)phenyl]sulfonyl]acetamide;

N-[[4-[2-(5-methylpyridin-3-yl)-4-(trifluoromethyl)-1H-imidazol-1-yl]phenyl]sulfonyl]acetamide;

N-[[4-[2-(2-methylpyridin-3-yl)-4-(trifluoromethyl)-1H-imidazol-1-yl]phenyl]sulfonyl]acetamide;

N-[[4-[2-(5-methylpyridin-3-yl)-4-(trifluoromethyl)-1H-imidazol-1-yl]phenyl]sulfonyl]butanamide;

N-[[4-[2-(2-methylpyridin-3-yl)-4-(trifluoromethyl)-1H-imidazol-1-yl]phenyl]sulfonyl]butanamide;

N-[[4-[2-(3-chloro-5-methylpheny)-4-(trifluoromethyl)-1H-imidazol-1-yl]phenyl]sulfonyl]acetamide;

N-[[4-[3-(3-fluorophenyl)-5methylisoxazol-4-yl]phenyl] sulfonyl]acetamide;

2-methyl-N-[[4-(5-methyl-3-phenylisoxazol-4-yl)phenyl] sulfonyl]propanamide;

N-[[4-(5-methyl-3-phenylisoxazol-4-yl)phenyl]sulfonyl] propanamide;

N-[[$^4$-(5-methyl-3-phenylisoxazol-4-yl]phenyl)sulfonyl] benzamide;

2,2-dimethyl-N-[[4-(5-methyl-3-phenylisoxazol-4-yl) phenyl]sulfonyl]propanamide;

N-[[4-(5-methyl-3-phenylisoxazol-4-yl)phenyl]sulfonyl] butanamide;

N-[[4-(5-methyl-3-phenylisoxazol-4-yl)phenyl]sulfonyl] pentanamide;

N-[[4-(5-methyl-3-phenylisoxazol-4-yl)phenyl]sulfonyl] hexanamide;

3-methoxy-N-[[4-(5-methyl-3-phenylisoxazol-4-yl) phenyl]sulfonyl]propanamide;

2-ethoxy-N-[[4-(5-methyl-3-phenylisoxazol-4-yl)phenyl]
  sulfonyl]acetamide;
N-[[4-(5-methyl-3-phenylisoxazol-4-yl)phenyl]sulfonyl]
  acetamide;
N-[[4-(5-(4-chlorophenyl)-3-(trifluoromethyl)-1H-
  pyrazol-1-yl)phenyl]sulfonyl]propanamide;
N-[[4-(5-(4-chlorophenyl)-3-(trifluoromethyl)-1H-
  pyrazol-1-yl]sulfonyl]Butanamide;
N-[[4-(5-(4-chlorophenyl)-3-(trifluoromethyl)-1H-
  pyrazol-1-yl]sulfonyl]acetamide;
N-[[4-(6-fluor-1,5-dihydro-7-methoxy-3-
  (trifluoromethyl)-(2) benzothiopyrano (4,3-c)pyrazol-
  1-yl)phenyl]sulfonyl]acetamide;
N-[[4-(2-methyl-4-phenyloxazol-5-yl)phenyl]sulfonyl]
  acetamide;
methyl [[[4-(5-methyl-3-phenylisoxazolk-4-yl]phenyl]
  sulfonyl]amino)oxoacetate;
2-methoxy-N-[[4-(5-methyl-3-phenylisoxazol-4-yl)
  phenyl]sulfonyl]acetamide;
N-[[4-[5-(difluoromethyl)-3-phenylisoxazol-4-yl]phenyl]
  sulfonyl]propanamide;
N-[[4-[5-(difluoromethyl)-3-phenylisoxazol-4-yl]phenyl]
  sulfonyl]butanamide;
4-[[4-(5-methyl-3-phenylisoxazol-4-yl)phenyl]sulfonyl]
  amino-4-oxobutanoic acid;
N-[[4-(5-methyl-3-phenylisoxazol-4-yl)phenyl]sulfonyl]
  formamide;
1,1-dimethylethyl -[[4-(5-methyl-3-phenylisoxazol-4-yl)
  phenyl]sulfonyl]carbamate;
N-[[4-(5-methyl-3-phenylisoxazol-4-yl)phenyl]sulfonyl]
  glycine;
2-amino-N-[[4-(5-methyl-3-phenylisoxazol-4-yl)phenyl]
  sulfonyl]acetamide;
2-(acetylamino)-N-[[4-(5-methyl-3-phenylisoxazol-4-yl)
  phenyl]sulfonyl]acetamide;
methyl 4-[[(4-(5-methyl-3-phenylisoxazol-4-yl)phenyl]
  sulfonyl]amino)-4-oxobutanoate;
methyl N-[[4-(5-methyl-3-phenylisoxazol-4-yl)phenyl]
  sulfonyl]carbamate;
N-[[4-(5-(4-methylphenyl)-3-(trifluoromethyl)-1H-
  pyrazol-1-yl)pheny]sulfonyl]acetamide;
methyl 3-[[(4-(5-methyl-3-phenylisoxazol-4-yl)phenyl]
  sulfonyl]amino)-3-oxopropanoate;
N-[[4-(5-(hydroxymethyl)-3-phenylisoxazol-4-yl)
  phenyl]sulfonyl]acetamide;
N-[[4-(5-(acetoxymethyl)-3-phenylisoxazol-4-yl)phenyl]
  sulfonyl]acetamide;
1,1-dimethylethyl-N-(2-[[(4-(5-methyl-3-
  phenylisoxazol-4-yl)phenyl]sulfonyl]amino)-2-
  oxoethyl)carbamate;
N-[[4-(3,4-dimethyl-1-phenyl-1H-pyrazol-5-yl)phenyl]
  sulfonyl]propanamide;
N-[[4-(2-(2-methylpyridin-3-yl)-4-
  trifluoromethylimidazol-1-yl)phenyl]sulfonyl]
  propanamide;
N-[[4-(2-(3-Chloro-4-fluorophenyl)cyclopenten-1-yl)
  phenyl]sulfonyl]acetamide; and
N-[[4-(3-phenyl-2,3-dihydro-2-oxofuran-4-yl)phenyl]
  sulfonyl]propanamide.

9. Compound of claim 5 wherein the pharmaceutically-acceptable salt is a metal salt.

10. Compound of claim 9 wherein the pharmaceutically-acceptable salt is selected from an alkali metal salt and an alkaline earth metal salt.

11. Compound of claim 10 wherein the pharmaceutically acceptable salt is selected from a sodium salt and a potassium salt.

12. Compound of claim 11 selected from the group consisting of
  N-[[4-[3-(difluoromethyl)-5-(3-fluoro-4-
    methoxyphenyl)-1H-pyrazol-1-yl]phenyl]sulfonyl]
    propanamide, sodium salt;
  N-[[4-[3-(difluoromethyl)-5-(3-fluoro-4-
    methoxyphenyl)-1H-pyrazol-1-yl]phenyl]sulfonyl]
    butanamide, sodium salt;
  N-[[4-(1,5-dimethyl)-3-phenyl-1H-pyrazol-4-yl]phenyl]
    sulfonyl]acetamide, sodium salt;
  N-[[4-(2-(3-pyridinyl)-4-(trifluoromethyl)-1H-imidazol-
    1-yl]phenyl]sulfonyl]acetamide, sodium salt;
  N-[[4-(2-(5-methylpyridin-3-yl)-4-(trifluoromethyl)-1H-
    imidazol-1-yl]phenyl]sulfonyl]butanamide, sodium
    salt;
  N-[[4-(2-(2-methylpyridin-3-yl)-4-(trifluoromethyl)-1H-
    imidazol-1-yl]phenyl]sulfonyl]butanamide, sodium
    salt;
  N-[[4-(2-(3-chloro-5-methylphenyl)-4-(trifluoromethyl)-
    1H-imidazol-1-yl]phenyl]sulfonyl]acetamide, sodium
    salt;
  N-[[4-(2-(3-fluorophenyl)-5-(methylisoxazole)-4-yl]
    phenyl]sulfonyl]acetamide, sodium salt;
  2-methyl-N-[[4-(5-methyl-3-phenylisoxazol-4-yl)phenyl]
    sulfonyl]propanamide, sodium salt;
  N-[[4-(5-methyl-3-phenylisoxazol-4-yl)phenyl]sulfonyl]
    propanamide, sodium salt;
  N-[[4-(5-methyl-3-phenylisoxazol-4-yl)phenyl]sulfonyl]
    benzamide, sodium salt;
  2,2-dimethyl-N-[[4-(5-methyl-3-phenylisoxazol-4-yl)
    phenyl]sulfony]propanamide, sodium salt;
  N-[[4-(5-methyl-3-phenylisoxazol-4-yl)phenyl]sulfonyl]
    butanamide, sodium salt;
  N-[[4-(5-methyl-3-phenylisoxazol-4-yl)phenyl]sulfonyl]
    pentanamide, sodium salt;
  N-[[4-(5-methyl-3-phenylisoxazol-4-yl)phenyl]sulfonyl]
    hexanamide, sodium salt;
  3-methoxy-N-[[4-(5-methyl-3-phenylisoxazol-4-yl)
    phenyl]sulfonyl]propanamide, sodium salt;
  2-ethoxy-N-[[4-(5-methyl-3-phenylisoxazol-4-yl)phenyl]
    sulfonyl]acetamide, sodium salt;
  N-[[4-(5-methyl-3-phenylisoxazol-4-yl)phenyl]sulfonyl]
    acetamide, sodium salt;
  N-[[4-(5-methyl-3-phenylisoxazol-4-yl)phenyl]sulfonyl]
    acetamide, potassium salt;
  N-[[4-(5-(4-chlorophenyl)-3-(trifluoromethyl)-1H-
    pyrazol-1-yl]phenyl]sulfonyl]propanamide, sodium
    salt;
  N-[[4-(5-(4-chlorophenyl)-3-(trifluoromethyl)-1H-
    pyrazol-1-yl]phenyl]sulfonyl]butanamide, sodium salt;
  N-[[4-(5-(4-chlorophenyl)-3-(trifluoromethyl)-1H-
    pyrazol-1-yl]phenyl]sulfonyl]acetamide, sodium salt;
  N-[[4-(3-(difluoromethyl)-6-fluoro-1,5-dihydro-7-
    methoxy-[2]benzothiopyrano[4,3-c]pyrazol-1-yl]
    phenyl]sulfonyl]acetamide, sodium salt;
  N-[[4-(6-fluoro-1,5-dihydro-7-methoxy-3-
    (trifluoromethyl)-[2]benzothiopyrano[4,3-c]pyrazol-1-
    yl]phenyl]sulfonyl]acetamide, sodium salt;
  N-[[4-(3-difluoromethyl)-5-(3-fluoro-4-methoxyphenyl)-
    1H-pyrazol-1-yl]phenyl]sulfonyl]acetamide, sodium
    salt;

N-[[4-(2-methyl-4-phenyloxazol-5-yl)phenyl]sulfonyl]
acetamide, sodium salt;
methyl [[[4-(5-methyl-3-phenylisoxazol-4-yl)phenyl]
sulfonyl]amino]oxoacetate, sodium salt;
2-methoxy-N-[[4-(5-methyl-3-phenylisoxazol-4-yl)
phenyl]sulfonyl]acetamide, sodium salt;
N-[[4-(5-difluoromethyl)-3-phenylisoxazol-4-yl)phenyl]
sulfonyl]propanamide, sodium salt;
N-[[4-(5-difluoromethyl)-3-phenylisoxazol-4-yl)phenyl]
sulfonyl]butanamide, sodium salt;
4-[[[4-(5-methyl-3-phenylisoxazol-4-yl)phenyl]sulfonyl]
amino]-4-oxobutanoic acid, sodium salt;
N-[[4-(5-methyl-3-phenylisoxazol-4-yl)phenyl]sulfonyl]
formamide, sodium salt;
1,1-dimethylethyl-N-[[4-(5-methyl-3-phenylisoxazole-4-
yl)phenyl]sulfonyl]carbamate, sodium salt;
N-[[4-(5-methyl-3-phenylisoxazol-4-yl)phenyl]sulfonyl]
glycine, sodium salt;
2-amino-N-[[4-(5-methyl-3-phenylisoxazol-4-yl)phenyl]
sulfonyl]acetamide, sodium salt;
2-(acetylamino)-N-[[4-(5-methyl-3-phenylisoxazol-4-yl)
phenyl]sulfonyl]acetamide, sodium salt;
methyl 4-[[[4-(5-methyl-3-phenylisoxazol-4-yl)phenyl]
sulfonyl]amino]-4-oxobutanoate, sodium salt;
methyl N-[[4-(5-methyl-3-phenylisoxazol-4-yl)phenyl]
sulfonyl]carbamate, sodium salt;
N-[[4-(5-hydroxymethyl-3-phenylisoxazol-4-yl)phenyl]
sulfonyl]acetamide, sodium salt;
N-[[4-(5-(4-methylphenyl)-3-(trifluoromethyl)-1H-
pyrazol-1-yl]phenyl]sulfonyl]acetamide, sodium salt;
methyl 3-[[[4-(5-methyl-3-phenylisoxazol-4-yl]phenyl]
sulfonyl]amino]-3-oxopropionate, sodium salt;
N-[[4-[5-(hydroxymethyl)-3-phenylisoxazol-4-yl]
phenyl]sulfonyl]acetamide, sodium salt;
N-[[4-[5-(hydroxymethyl)-3-phenylisoxazol-4-yl]
phenyl]sulfonyl]acetamide, sodium salt;
N-[[4-[5-(acetoxymethyl)-3-phenylisoxazol-4-yl]phenyl]
sulfonyl]acetamide, sodium salt;
N-[[4-[3,4-dimethyl-1-phenyl-1H-pyrazol-5-yl]phenyl]
sulfonyl]propanamide, sodium salt;
N-[[4-[2-(2-methylpyridin-3-yl)-4-
triflurormethylimidazol-1-yl]phenyl]sulfonyl]
propanamide, sodium salt;
N-[[4-[2-(3-chloro-4-fluorophenyl)cyclopenten-1-yl]
phenyl]sulfonyl]acetamide, sodium salt; and
N-[[4-(3-phenyl-2,3-dihydro-2-oxofuran-4-yl)phenyl]
sulfonyl]propanamide, sodium salt.

13. A pharmaceutical composition comprising a thetapeutically-effective amount of a compound, said compound selected from a family of compounds according to claim 1, including those wherein A is tetrazolium or A is indane when $R^3$ is alkyl or cycloalkyl; or according to any of claims 2–12.

14. A method of preparing a compound of Formula II

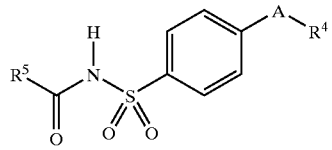

wherein A is a ring substituent selected from partially unsaturated heterocyclyl, 5- or 6-membered heteroaryl, $C_3$–$C_8$-cycloalkenyl and phenyl; wherein A is unsubstituted or substituted with one or more radicals selected from acyl, halo, hydroxy, $C_1$–$C_{10}$ alkyl, $C_1$–$C_6$ haloalkyl, oxo, cyano, nitro, carboxyl, $C_1$–$C_6$-alkoxy, aminocarbonyl, $C_1$–$C_6$ alkoxycarbonyl, carboxy-$C_1$–$C_{10}$-alkyl, $C_1$–$C_{10}$-cyanoalkyl, $C_1$–$C_6$-hydroxyalkyl, $C_1$–$C_{10}$-alkylcarbonyloxyalkyl, and phenyl;

wherein $R^4$ is selected from heterocyclyl, cycloalkyl, cyanoalkyl, and phenyl, wherein $R^4$ is unsubstituted or substituted with one or more radicals selected from $C_1$–$C_{10}$ alkyl, $C_1$–$C_6$ haloalkyl, cyano, carboxyl, $C_1$–$C_6$ alkoxycarbonyl, hydroxyl, $C_1$–$C_{10}$-hydroxyalkyl, $C_1$–$C_6$-haloalkoxy, amino, $C_1$–$C_6$ alkylamino, phenylamino, nitro, $C_1$–$C_{10}$ alkoxyalkyl, $C_1$–$C_6$ alkylsulfinyl, halo, $C_1$–$C_6$ alkoxy and $C_1$–$C_6$ alkylthio; and wherein $R^5$ is selected from hydrido, $C_1$–$C_{10}$-alkyl, $C_1$–$C_6$-alkoxy, $C_1$–$C_{10}$-alkoxyalkyl, phenyl, aryl-$C_1$–$C_{10}$-alkyl, carboxy-$C_1$–$C_{10}$-alkyl, $C_1$–$C_6$ alkoxycarbonylalkyl, $C_1$–$C_6$-alkoxycarbonyl, amino-$C_1$–$C_{10}$-alkyl, $C_1$–$C_6$ alkoxycarbonylaminoalkyl, and $C_1$–$C_{10}$ alkylcarbonylaminoalkyl;

further provided A is not thienyl when $R^4$ is 4-fluorophenyl and when $R^5$ is methyl;

or a pharmaceutically acceptable salt thereof;

the method comprising reacting an unsubstituted sulfonamide with an acylating agent in the presence of base and a solvent.

15. The method of claim 14 herein the acylating agent is selected from anhydrides, acid chlorides, acyl, imidazoles and active esters.

16. The method of claim 15, wherein the acylating agent is selected from acetic anhydride, propionic anhydride and butyric anhydride.

17. The method of claim 14 wherein the solvent is tetrahydrofuran.

18. A method of preparing a compound of Formula III

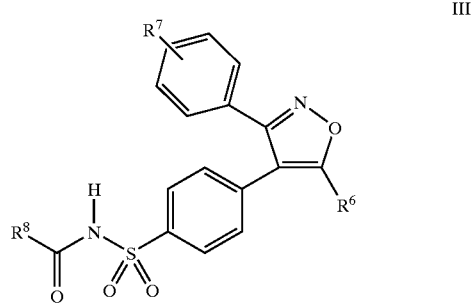

wherein $R^6$ is selected from hydroxyl, $C_1$–$C_{10}$ alkyl, carboxyl, halo, carboxy$C_1$–$C_{10}$-alkyl, $C_1$–$C_6$-alkoxycarbonylalkyl, aryl-$C_1$–$C_{10}$-alkyl, $C_1$–$C_{10}$-alkoxyalkyl, $C_1$–$C_{10}$-alkoxyalkoxyalkyl, aryl-$C_1$–$C_{10}$-alkoxyalkyl, halo-$C_1$–$C_{10}$ alkyl, $C_1$–$C_6$-hydroxyalkyl, aryl-$C_1$–$C_6$-(hydroxyalkyl), $C_1$–$C_6$-haloalkylsulfonyloxy, carboxy-$C_1$–$C_{10}$ alkoxyalkyl, $C_3$–$C_8$-cycloalkylalkyl and $C_3$–$C_8$-cycloalkyl;

wherein $R^7$ is one or more radicals selected from hydrido, $C_1$–$C_{10}$ alkyl, $C_1$–$C_6$ haloalkyl, cyano, carboxyl, $C_1$–$C_6$ alkoxycarbonyl, hydroxyl, $C_1$–$C_6$-hydroxyalkyl, $C_1$–$C_6$-haloalkoxy, amino, $C_1$–$C_6$ alkylamino, phenylamino, nitro, $C_1$–$C_{10}$ alkoxyalkyl, $C_1$–$C_6$ alkylsulfinyl, halo, $C_1$–$C_6$ alkoxy and $C_1$–$C_6$ alkylthio; and wherein $R^8$ is selected from hydrido, $C_1$–$C_{10}$-alkyl, $C_1$–$C_6$-alkoxy, $C_1$–$C_{10}$-alkoxyalkyl, phenyl, carboxy- $C_1$–$C_{10}$-alkyl, $C_1$–$C_6$ alkoxycarbonylalkyl, $C_1$–$C_6$-alkoxycarbonyl, amino-$C_1$–$C_{10}$-alkyl, $C_1$–$C_6$ alkoxycarbonylaminoalkyl, and $C_1$–$C_{10}$ alkylcarbonylaminoalkyl;

or a pharmaceutically acceptable salt thereof;

the method comprising reacting an unsubstituted isoxazolyl benzenesulfonamide with an acylating agent in the presence of base and a solvent.

19. A method of preparing a compound of Formula II

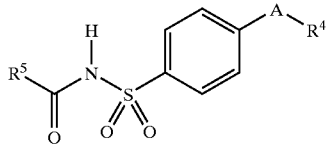

II wherein A is a ring substituent selected from partially unsaturated heterocyclyl, 5- or 6-membered heteroaryl, $C_3$–$C_8$-cycloalkenyl and phenyl; wherein A is unsubstituted or substituted with one or more radicals selected from acyl, halo, hydroxy, $C_1$–$C_{10}$ alkyl, $C_1$–$C_6$ haloalkyl, oxo, cyano, nitro, carboxyl, $C_1$–$C_6$-alkoxy, aminocarbonyl, $C_1$–$C_6$ alkoxycarbonyl, carboxy-$C_1$–$C_{10}$-alkyl, $C_1$–$C_{10}$-cyanoalkyl, $C_1$–$C_6$-hydroxyalkyl, $C_1$–$C_{10}$-alkylcarbonyloxyalkyl, and phenyl;

wherein $R^4$ is selected from heterocyclyl, cycloalkyl, cyanoalkyl, and phenyl, wherein $R^4$ is unsubstituted or substituted with one or more radicals selected from $C_1$–$C_{10}$ alkyl, $C_1$–$C_6$ haloalkyl, cyano, carboxyl, $C_1$–$C_6$ alkoxycarbonyl, hydroxyl, $C_1$–$C_{10}$-hydroxyalkyl, $C_1$–$C_6$-haloalkoxy, amino, $C_1$–$C_6$ alkylamino, phenylamino, nitro, $C_1$–$C_{10}$ alkoxyalkyl, $C_1$–$C_6$ alkylsulfinyl, halo, $C_1$–$C_6$ alkoxy and $C_1$–$C_6$ alkylthio; and wherein $R^5$ is selected from hydrido, $C_1$–$C_{10}$-alkyl, $C_1$–$C_6$-alkoxy, $C_1$–$C_{10}$-alkoxyalkyl, phenyl, aryl-$C_1$–$C_{10}$-alkyl, carboxy-$C_1$–$C_{10}$-alkyl, $C_1$–$C_6$ alkoxycarbonylalkyl, $C_1$–$C_6$-alkoxycarbonyl, amino-$C_1$–$C_{10}$-alkyl, $C_1$–$C_6$ alkoxycarbonylaminoalkyl, and $C_1$–$C_{10}$ alkylcarbonylaminoalkyl;

the method comprising forming a bis(N-acylated) sulfonamide by reacting an unsubstituted sulfonamide with an excess of an anhydride, acid chloride or carbamyl chloride, in the presence of a tertiary amine base, and reacting said bis(N-acylated)-sulfonamide with about two equivalents of a strong base to provide the salt.

20. A method of preparing a compound of Formula II

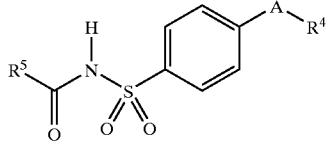

II wherein A is a ring substituent selected from partially unsaturated heterocyclyl, 5- or 6-membered heteroaryl, $C_4$–$C_8$-cycloalkenyl and phenyl; wherein A is unsubstituted or substituted with one or more radicals selected from acyl, halo, hydroxy, $C_1$–$C_{10}$ alkyl, $C_1$–$C_6$ haloalkyl, oxo, cyano, nitro, carboxyl, $C_1$–$C_6$-alkoxy, aminocarbonyl, $C_1$–$C_6$ alkoxycarbonyl, carboxy-$C_1$–$C_{10}$-alkyl, $C_1$–$C_{10}$-cyanoalkyl, $C_1$–$C_6$-hydroxyalkyl, $C_1$–$C_{10}$-alkylcarbonyloxyalkyl, and phenyl;

wherein $R^4$ is selected from heterocyclyl, cycloalkyl, cyanoalkyl, and phenyl, wherein $R^4$ is unsubstituted or substituted with one or more radicals selected from $C_1$–$C_1$ alkyl, $C_1$–$C_6$ haloalkyl, cyano, carboxyl, $C_1$–$C_6$ alkoxycarbonyl, hydroxyl, $C_1$–$C_{10}$-hydroxyalkyl, $C_1$–$C_6$-haloalkoxy, amino, $C_1$–$C_6$ alkylamino, phenylamino, nitro, $C_1$–$C_{10}$ alkoxyalkyl, $C_1$–$C_6$ alkylsulfinyl, halo, $C_1$–$C_6$ alkoxy and $C_1$–$C_6$ alkylthio; and wherein $R^5$ is selected from hydrido, $C_1$–$C_{10}$-alkyl, $C_1$–$C_6$-alkoxy, $C_1$–$C_{10}$-alkoxyalkyl, phenyl, aryl-$C_1$–$C_{10}$-alkyl, carboxy-$C_1$–$C_{10}$-alkyl, $C_1$–$C_6$-alkoxycarbonylalkyl, $C_1$–$C_6$-alkoxycarbonyl, amino-$C_1$–$C_{10}$-alkyl, $C_1$–$C_6$-alkoxycarbonylaminoalkyl, and $C_1$–$C_{10}$-alkylcarbonylaminoalkyl;

further provided A is not thienyl when $R^4$ is 4-fluorophenyl and when $R^5$ is methyl;

or a pharmaceutically acceptable salt thereof, the method comprising reacting an unsubstituted sulfonamide with an acylating agent in the presence of acid.

21. The method of claim 20 wherein the acylating agent is selected from anhydrides and acid chlorides.

22. The method of claim 21 wherein the acylating agent is selected from acetyl chloride, acetic anhydride, propionic anhydride and butyric anhydride.

23. The method of claim 20 herein A is selected from oxazolyl, furyl, thiazolyl, imidazolyl, benzofuryl, indenyl, benzothienyl, isoxazolyl, pyrazoiyl, cyclopentenyl, cyclopentadienyl, benzindazolyl, benzopyranopyrazolyl, phenyl, and pyridyl.

24. The method of claim 23 wherein A is selected from imidazolyl, isoxazolyl, and pyrazolyl.

25. A method for the treatment or prevention of inflammation or an inflammation mediated disorder in a subject in need of such treatment comprising administering to the subject an effective amount of a compound according to any of claims 1–12 or a pharmaceutically acceptable salt.

26. A method according to claim 25 wherein the condition to be treated is inflammation.

27. A method according to claim 25 wherein the condition to be treated is an inflammation-associated disorder.

28. A method according to claim 27 wherein the inflammation-associated disorder is pain.

29. A method according to claim 28 wherein the pain is associated with cancer.

30. A method according to claim 28 wherein the pain is dental pain.

31. A method according to claim 28 wherein the compound is administered intravenously.

32. A method according to claim 28 wherein the compound is administered intramuscularly.

* * * * *

UNITED STATES PATENT AND TRADEMARK OFFICE
CERTIFICATE OF CORRECTION

PATENT NO. : 6,436,967 B1
DATED : August 20, 2002
INVENTOR(S) : John J. Talley et al.

It is certified that error appears in the above-identified patent and that said Letters Patent is hereby corrected as shown below:

Column 78,
Line 13, "N-phenylarnino" should read -- N-phenylamino --.
Line 35, "pharnaceutically" should read -- pharmaceutically --.
Line 47, "phenylnethyl" should read -- phenylmethyl --.

Column 79,
Line 15, "N-[[$^4$-" should read -- N-[[4- --.
Line 37, "N-[[4-5" should read -- N-[[4-(5 --.

Column 81,
Line 28, "alkysulfumyl" should read -- alkylsulfinyl --.

Column 82,
Line 35, "imdazol" should read -- imidazol --.
Line 55, "N-[[$^4$-" should read -- N-[[4- --.

Column 86,
Line 28, "herein" should read -- wherein --.

Column 88,
Line 10, "$C_1$-$C_1$" should read -- $C_1$-$C_{10}$ --.
Line 32, "herein" should read -- wherein --.
Line 34, "pyrazoiyl" should read -- pyrazolyl --.

Signed and Sealed this

Thirteenth Day of April, 2004

JON W. DUDAS
*Acting Director of the United States Patent and Trademark Office*